(12) United States Patent
Wu et al.

(10) Patent No.: US 10,233,277 B2
(45) Date of Patent: Mar. 19, 2019

(54) POLYMERIC NANOPARTICLES USEFUL IN THERANOSTICS

(71) Applicant: The Governing Council of the University of Toronto, Toronto (CA)

(72) Inventors: Xiao Yu Wu, Toronto (CA); Alireza Shalviri, Toronto (CA); Ping Cai, Toronto (CA)

(73) Assignee: The Governing Council of the University of Toronto, ON (CA)

( * ) Notice: Subject to any disclaimer, the term of this patent is extended or adjusted under 35 U.S.C. 154(b) by 767 days.

(21) Appl. No.: 14/382,495

(22) PCT Filed: Mar. 4, 2013

(86) PCT No.: PCT/CA2013/000203
§ 371 (c)(1),
(2) Date: Sep. 2, 2014

(87) PCT Pub. No.: WO2013/127004
PCT Pub. Date: Sep. 6, 2013

(65) Prior Publication Data
US 2015/0132384 A1 May 14, 2015

Related U.S. Application Data

(60) Provisional application No. 61/605,995, filed on Mar. 2, 2012.

(51) Int. Cl.
| | | |
|---|---|---|
| C08F 251/00 | (2006.01) | |
| A61K 9/14 | (2006.01) | |
| A61K 31/197 | (2006.01) | |
| A61K 47/36 | (2006.01) | |
| A61K 38/08 | (2006.01) | |
| A61K 31/704 | (2006.01) | |
| A61K 47/32 | (2006.01) | |
| C08J 3/14 | (2006.01) | |
| C08F 8/00 | (2006.01) | |
| A61K 9/51 | (2006.01) | |
| A61K 49/00 | (2006.01) | |
| A61K 49/18 | (2006.01) | |
| B82Y 40/00 | (2011.01) | |

(52) U.S. Cl.
CPC .............. *C08F 251/00* (2013.01); *A61K 9/14* (2013.01); *A61K 9/5161* (2013.01); *A61K 9/5192* (2013.01); *A61K 31/197* (2013.01); *A61K 31/704* (2013.01); *A61K 38/08* (2013.01); *A61K 47/32* (2013.01); *A61K 47/36* (2013.01); *A61K 49/0093* (2013.01); *A61K 49/1818* (2013.01); *A61K 49/1881* (2013.01); *C08F 8/00* (2013.01); *C08J 3/14* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 4,690,996 A | 9/1987 | Shih et al. | |
| 5,583,193 A | 12/1996 | Aravindakshan et al. | |
| 2010/0297007 A1* | 11/2010 | Lanza | A61K 9/1075 424/1.65 |
| 2011/0110868 A1* | 5/2011 | Akhtari | A61K 47/48092 424/9.322 |
| 2012/0277158 A1* | 11/2012 | Castaigne | C07K 7/083 514/17.5 |

FOREIGN PATENT DOCUMENTS

| | | |
|---|---|---|
| CN | 1388169 A | 1/2013 |
| EP | 1711479 B1 | 2/2008 |
| JP | 62-53366 A | 3/1987 |

(Continued)

OTHER PUBLICATIONS

Sajeesh et al., "Novel pH Responsive Polymethacrylic Acid-Chitosan-Polyethylene Glycol Nanoparticles for Oral Peptide Delivery", Division of Biosurface Technology, Biomedical Technology Wing, Sree Chitra Tirunal Institute for Medical Sciences and Technology, Trivandrum, Kerala, India, Published online Aug. 29, 2005 in Wiley InterScience <www.interscience.wiley.com>, 8 pages.

Search Report and Written Opinion received for Singapore Patent Application No. 11201405407W, completed on Oct. 1, 2015, 9 pages.

Romaskevic et al., "Synthesis of Chitosan-Graft-Poly(Ethylene Glycol) Methyl Ether Methacrylate Copolymer and its Application for Immobilization of Maltogenase", Chemija, vol. 18, No. 2, 2007, pp. 33-38.

Alyautdin et al., "Delivery of Loperamide Across the Blood-Brain Barrier with Polysorbate 80-Coated Polybutylcyanoacrylate Nanoparticles", Pharmaceutical Research, vol. 14, No. 3, 1997, pp. 325-328.

(Continued)

*Primary Examiner* — Robert A Wax
*Assistant Examiner* — Randeep Singh
(74) *Attorney, Agent, or Firm* — Fiala & Weaver P.L.L.C.

(57) ABSTRACT

Synthesis and characterization of starch based pH-responsive nanoparticles for controlled drug delivery are described. Polymethacrylic acid grafted starch (PMAA-g-St) nanoparticles with various molar ratio of starch to MAA were synthesized by a new one-pot method that enabled simultaneous grafting of PMAA and nanoparticle formation in an aqueous medium. NMR data showed that polysorbate 80 was polymerized into the graft polymer. Nanoparticles were relatively spherical with narrow size distribution and porous surface morphology and exhibited pH-dependent swelling in physiological pH range. The particle size and magnitude of volume phase transition were dependent on PMAA content and formulation parameters such as surfactant levels, crosslinker amount, and total monomer concentration. The results showed that the new pH-responsive nanoparticles possessed useful properties for controlled drug delivery.

16 Claims, 64 Drawing Sheets

(56) References Cited

FOREIGN PATENT DOCUMENTS

| WO | 0050050 A1 | 8/2000 |
|---|---|---|
| WO | 2010/015715 A2 | 2/2010 |

OTHER PUBLICATIONS

Beliakova et al., "Grafting of Poly (Methacrylic Acid) on Starch and Poly(Vinyl Alcohol)", Starch Stäarke, vol. 56, 2004, pp. 407-412.

Celik et al., "Synthesis and Characterization of Starch-Poly(Methyl Methacrylate) Graft Copolymers", Journal of Applied Polymer Science, vol. 86, 2002, pp. 53-57.

Hebeish et al., "Improved Synthesis of Poly (MAA)-Starch Graft Copolymers", Journal of Applied Polymer Science, vol. 68, 1998, pp. 1709-1715.

Kreuter et al., "Covalent Attachment of Apolipoprotein A-I and Apolipoprotein B-100 to Albumin Nanoparticles Enables Drug Transport into the Brain", Journal of Controlled Release, vol. 118, 2007, pp. 54-58.

Kurakhmaeva et al., "Brain Targeting of Nerve Growth Factor Using Poly (Butyl Cyanoacrylate) Nanoparticles", Journal of Drug Targeting, vol. 17, No. 8, 2009, pp. 564-574.

Liu et al., "Graft Copolymerization of Methyl Acrylate onto Potato Starch Initiated by Ceric Ammonium Nitrate", Journal of Polymer Science: Part A Polymer Chemistry, vol. 31, 1993, pp. 3181-3186.

Michaelis et al., "Covalent Linkage of Apolipoprotein E to Albumin Nanoparticles Strongly Enhances Drug Transport into the Brain", Journal of Pharmacology and Experimental Therapeutics, vol. 317, No. 3, 2006, pp. 1246-1253.

Saboktakin et al., "pH-Sensitive Starch Hydrogels via Free Radical Graft Copolymerization, Synthesis and Properties", Carbohydrate Polymers, vol. 77, 2009, pp. 634-638.

Sangramsingh et al., "Graft Copolymerization of Methyl Methacrylate onto Starch Using a Ce (IV)—Glucose Initiator System", Journal of Applied Polymer Science, vol. 91, 2004, pp. 981-990.

Shalviri et al., "Design of pH-Responsive Nanoparticles of Terpolymer of Poly(Methacrylic Acid), Polysorbate 80 and Starch for Delivery of Doxorubicin", Colloids and Surfaces B: Biointerfaces, vol. 101, 2013, pp. 405-413.

Shalviri et al., "Novel Modified Starch-Xanthan Gum Hydrogels for Controlled Drug Delivery: Synthesis and Characterization", Carbohydrate Polymers, vol. 79, 2010, pp. 898-907.

Tosi et al., "Targeting the Central Nervous System: In Vivo Experiments with Peptide-Derivatized Nanoparticles Loaded with Loperamide and Rhodamine-123," Journal of Controlled Release, vol. 122, 2007, pp. 1-9.

Wohlfart et al., "Transport of Drugs Across the Blood-Brain Barrier by Nanoparticles", Journal of Controlled Release, vol. 161, 2012, pp. 264-273.

Zensi et al., "Albumin Nanoparticles Targeted with Apo E enter the CNS by Transcytosis and are Delivered to Neurones", Journal of Controlled Release, vol. 137, 2009, pp. 78-86.

Zhang et al., "Grafting of 2-(Dimethylamino)Ethyl Methacrylate onto Potato Starch Using Potassium Permanganate/Sulfuric Acid Initiation System," Starch Stärke, vol. 53, 2001, pp. 311-316.

International Search Report and Written Opinion received for PCT Patent Application No. PCT/CA2013/000203 dated Jul. 18, 2013, 7 pages.

Office Action issued in Japanese Application No. 2014-559046, dated Jan. 31, 2017, 2 pages of English Translation and 3 pages of Japanese Office Action.

* cited by examiner

| Sample code | Feed composition | | Polymer composition* (molar ratio) MAA/PS 80/St | Grafting yield (GY %) |
|---|---|---|---|---|
| | St (mmol) | MAA (mmol) | | |
| PMAA | 0 | 28.0 | 1 / 0.0021 / 0 | N/A |
| PMAA-g-St-1 | 4.9 | 23.1 | 1 / 0.0029 / 0.28 | 67 |
| PMAA-g-St-2 | 9.6 | 18.4 | 1 / 0.0041 / 0.66 | 60 |
| PMAA-g-St-3 | 12.0 | 16.0 | 1 / 0.0045 / 0.90 | 55 |
| PMAA-g-St-4 | 18.0 | 10.0 | 1 / 0.011 / 2.12 | 52 |

Figure 45

| Sample code | Feed composition | | Polymer composition* (molar ratio) | MAA content** (mmol/g) | Reaction yield (RY %) |
|---|---|---|---|---|---|
| | MAA (mmol) | St (mmol) | MAA/PS 80/St | | |
| PMAA-PS 80 | 28.0 | 0 | 1 / 0.0075 / 0 | 8.34 | 50 |
| PMAA-PS 80-g-St-1 | 23.1 | 4.9 | 1 / 0.015 / 0.24 | 6.23 | 67 |
| PMAA-PS 80-g-St-2 | 18.4 | 9.6 | 1 / 0.019 / 0.66 | 4.58 | 60 |
| PMAA-PS 80-g-St-3 | 16.0 | 12.0 | 1 / 0.024 / 0.86 | 3.36 | 55 |
| PMAA-PS 80-g-St-4 | 10.0 | 18.0 | 1 / 0.039 / 2.16 | 2.01 | 52 |

KPS = 0.45 mmol, STS = 1.36 mmol, PS 80 = 0.57 mmol, SDS = 0.69 mmol, MBA = 3.2 mmol, water = 200 ml, Temp = 65 °C.
\* calculated using 1H NMR
\*\* calculated using titration

Figure 46

| Sample code | MAA:St molar ratio (feed) | Size (nm) pH=4 | pH=5 | pH=6 | pH=7.4 | $V_{7.4}/V_4$* | PdI |
|---|---|---|---|---|---|---|---|
| MAA | N/A | 70.5 ± 0.4 | 88.2 ± 0.8 | 138.0 ± 1.0 | 152.2 ± 1.1 | 10.1 | 0.26 |
| MAA-g-St-1 | 4.7 | 110.4 ± 0.4 | 116.5 ± 1.4 | 180.9 ± 0.4 | 200.4 ± 0.9 | 6.0 | 0.14 |
| MAA-g-St-2 | 1.9 | 201.2 ± 0.5 | 223.8 ± 1.2 | 290.2 ± 21.5 | 298.4 ± 2.6 | 3.3 | 0.09 |
| MAA-g-St-3 | 1.3 | 229.0 ± 5.2 | 240.2 ± 1.9 | 297.1 ± 1.4 | 310.0 ± 3.1 | 2.48 | 0.11 |
| MAA-g-St-4 | 0.6 | 235.1 ± 3.4 | 237.7 ± 2.1 | 264.3 ± 4.0 | 271.7 ± 3.3 | 1.5 | 0.12 |

* ratio of particle diameter at pH = 7.4 to pH = 4 to the power of 3.

Figure 47

| Sample code | Feed MAA content (mmol/g) | Equivalent point (ml) | Product MAA content (mmol/g) | Zeta potential (mV) | |
|---|---|---|---|---|---|
| | | | | pH=7.4 | pH=4 |
| PMAA | 9.25 | 4.2 | 8.34 | -41.7 ± 0.6 | -31.5 ± 1.3 |
| PMAA-g-St-1 | 6.92 | 3.1 | 6.23 | -34.3 ± 0.9 | -24.3 ± 0.8 |
| PMAA-g-St-2 | 5.0 | 2.39 | 4.58 | -33.0 ± 0.8 | -19.5 ± 0.4 |
| PMAA-g-St-3 | 4.10 | 1.7 | 3.36 | -31.9 ± 0.7 | -19.1 ± 0.2 |
| PMAA-g-St-4 | 2.57 | 1.0 | 2.01 | -15.6 ± 1.4 | -2.7 ± 0.7 |

Figure 48

| Formulation | Gd content (wt%) | $r_1$ (mM$^{-1}$s$^{-1}$) | | Size (nm) | Zeta potential (mV) |
|---|---|---|---|---|---|
| | | 3T | 7T | | |
| Omniscan | 26.7 | 4.04 | 3.9 | N/A | N/A |
| St-DTPA-g-pMAA-LP | 9.3 | 21.8 | 16.7 | soluble | N/A |
| St-DTPA-g-pMAA-NP | 17.2 | 29.2 | 23.1 | 205 ± 9 | -28.5 ± 0.7 |

Figure 49A

| Formulation | Gd content (wt%) | Dox loading content (wt%) | $r_1$ (mM⁻¹s⁻¹) 3 T | $r_1$ (mM⁻¹s⁻¹) 7 T | Molecular weight (kDa) | Particle size (nm) | Zeta potential (mV) |
|---|---|---|---|---|---|---|---|
| Omniscan® | 26.7 ± 1.0 | N/A | 4.0 ± 0.1 | 3.9 ± 0.1 | 0.57 | soluble | N/A |
| PolyGd | 9.3 ± 0.7 | N/A | 21.8 ± 0.2 | 16.7 ± 0.3 | 47 ± 5 | soluble | N/A |
| PolyGd-Dox | 8.2 ± 0.5 | 10.1 ± 0.9 | 19.2 ± 0.7 | 13.3 ± 0.4 | N/A | 67 ± 10 | -28 ± 5 |

Figure 49B

| Pharmacokinetic parameters | SA-NPs | PF-NPs |
|---|---|---|
| $t_{1/2}$ (hr) | 92.5 ± 11.9 | 277.2 ± 33.3 |
| $K_d$ (hr$^{-1}$) | 0.0075 ± 0.0006 | 0.0025 ± 0.0003 |
| AUC (p/sec/cm²/sr)/(μw/cm²)hr × 10$^{10}$ | 8.03 ± 1.60 | 2.24 ± 0.50 |

Figure 50

| Sample Code | Feed Composition (mol/l) | | | Grafting Yield |
|---|---|---|---|---|
| | Starch | DEAEM | EGDM | % |
| PDEAEM | 0 | 0.43 | 0.0026 | N/A |
| PDEAEM-g-St-1 | 0.11 | 0.32 | 0.0026 | 25 |
| PDEAEM-g-St-2 | 0.25 | 0.18 | 0.02 | 22 |
| PDEAEM-g-St-3 | 0.36 | 0.07 | 0.02 | 16 |

Figure 51

POLYMERIC NANOPARTICLES USEFUL IN THERANOSTICS

FIELD OF THE INVENTION

The present invention relates to polymeric nanoparticles useful for delivery of therapeutic and/or diagnostic agents.

BACKGROUND OF THE INVENTION

Many natural polysaccharides, such as starch and alginate, are found in food or used as food ingredients. Starch is one of the most abundant polysaccharides occurring in nature. This biopolymer has a molecular formula of $(C_6H_{10}O_5)_n$, with n ranging from 300 to 1000 [1]. Starch is composed of a mixture of two polymers called amylose and amylopectin [1, 2]. Amylose molecules consists of α-D-glucopyranose units joined by α-1,4 acetal linkages. Amylopectin molecules are much larger and highly branched. The molecule contains α-1,4 linear bounds, and is branched through α-1,6 linkages [1, 2]. Most starches used in industry usually contain between 20 and 30% amylose with the remainder being amylopectin (70-80%) and minor components (less than 1%) such as lipids and protein [3].

Starch offers distinct advantages. Starch is relatively safe, having biocompatibility and biodegradability profiles well suited for in vivo applications. In the context of colloidal systems, starch has stabilizing properties making it a useful candidate for biomolecular development. Starch contains an abundance of hydroxyl groups capable of undergoing various chemical reactions characteristic of alcohols. This makes it possible for a variety of drugs, targeting moieties, metal chelators, fluorescence probes, etc. to be conjugated to starch-based materials. Starch-based materials can also be quite cost effective. Despite these advantages, starch has had limited use as a biomaterial and in drug delivery applications. Native starch has limited use due to its poor mechanical and chemical properties; however, various modifications can be made to improve the properties of starch and broaden its applications. The most common chemical modifications are grafting, oxidation, esterification, etherification, and hydrolysis. The grafting of starch with acrylic-based monomers can produce materials with potential drug delivery and biomedical applications due to the combination of biodegradable and stabilizing properties of starch with pH-responsive characteristics of acrylic polymer.

Starch-xanthan gum hydrogels have been synthesized for controlled drug delivery by cross-linking starch and xanthan gum by sodium trimethaphosphate [4]. Starch has been modified by grafting polymerization of various vinyl monomers [5] using radiation, photolysis, or catalysts and initiators such as metallic ions, peroxides, or persulfate [5-12]. Grafting of vinyl monomers onto starch is generally achieved by free radical initiation. Starch graft copolymers have been used as hydrogels, flocculants, ion exchangers, superabsorbents, and so on [13-18].

Hydrophilic acrylic monomers can form hydrogels with adjustable swelling kinetics and have been utilized for drug delivery and other biomedical applications such as improvement of osteoblast adhesion [19-21]. Combination of biodegradable properties of starch with pH responsive characteristics of acrylic based polymers may lead to interesting hydrogels with potentials in biomedical and drug delivery. Previously published work has shown that potassium persulfate is able to initiate grafting of methacrylic acid onto starch; however, substantial amount of homopolymer is formed [22]. By using potassium persulfate/sodium thiosulfate redox initiation system, Hebeish et al. were able to efficiently graft polymethacrylic acid onto starch while minimizing homopolymer formation [6, 7].

In many applications, fast phase transition in response to environmental stimuli, such as pH, is desirable. However, bulk hydrogels of large dimensions normally undergo slow dimensional change because conformational changes in polymeric networks and diffusion of solute and water through the network take time. Since the response time is proportional to the square of diffusion distance, the phase transition rate can be controlled by adjusting hydrogel dimensions [23]. Generally, nano-sized polymers undergo swelling equilibrium, and phase transition in order of microseconds. Hence, stimulus responsive nanoparticles can be potentially useful in stimulus-responsive drug delivery, and can serve as sensors or microswitches because of their extremely fast response to stimuli.

Despite numerous publications on grafting polymerization of vinyl monomers, the published data on development and characterization of nano-sized starch based pH sensitive particles is very limited. Saboktakin et al. have recently described the grafting of the polymethacrylic acid onto carboxymethyl starch to produce bulk polymer [24]. The authors have subsequently used a freeze drying method to produce nanopowders; however, their method does not produce stable colloidal dispersion of nanoparticles in aqueous medium. Saboktakin et al. have also described the grafting of the polymethacrylic acid onto chitosan nanoparticles as delivery systems for paclitaxel [24(a)]. Hirosue et al. have described in international patent publication WO 2010/084060 a polymer having a starch backbone onto which methylacrylate monomer was grafted by atom transfer radical polymerization (ATRP) subsequent to modification of backbone hydroxyl groups by a linker such as 2-bromo isobutyryl bromide. Nanoparticles were formulated with the starch polymer by an emulsion diffusion method.

DESCRIPTION OF THE INVENTION

The invention described herein includes a method for the synthesis of nanoparticles.

Nanoparticles of the invention include a polymer backbone having grafted thereto polymeric chains containing carboxyl groups or amino groups. Covalently linked as part of the nanoparticle are polyethoxylate moieties that present on the exterior surface of the nanoparticles.

Nanoparticles of the invention are especially useful as carriers for e.g., therapeutics and/or signal molecules.

Preferably, nanoparticles of the invention are formed in aqueous solution in a "one-pot" synthetic procedure in which a monomer graft polymerizes onto a backbone polymer and polyethoxylate moieties participate in the polymerization to become covalently incorporated as part of the nanoparticle.

In disclosed embodiments, the polymer backbone is provided by starch, the monomer is methacrylic acid (MAA), diethylaminoethyl methacrylate (DEAEM), and the polyethoxylated moieties are provided by polysorbate 80 (Tween® 80).

Nanoparticles of the invention are particularly useful as a carrier nanoparticle. The cargo or payload of the carrier can be a therapeutic agent such as a drug, a signal molecule such as a fluorophore e.g., fluoresceinamine, gadolinium, etc.

A therapeutic can be loaded to the nanoparticle after its formation. Alternatively, and especially where the particle cargo includes a signal or other molecule that is not intended to be dislodged from the carrier particle while present in a patient, the polymer can be functionalized with the molecule by covalent attachment thereto before nanoparticle production. In disclosed examples, an organic chelator, diethylenetriaminepentaacetic dianhydride (DTPA bisanhydride), was covalently linked to nanoparticles. In one example, DTPA was covalently attached to a polysaccharide polymer backbone prior to production of the nanoparticle; in another example, DTPA was linked to the already formed nanoparticle. $Gd^{+3}$ was loaded into the chelator preinstalled as part of the nanoparticle.

In another example, the drug doxorubicin hydrochloride, known to be water soluble, was loaded into nanoparticles of the invention and in vivo behaviour characterized.

It is possible to obtain nanoparticles of the invention having a relative low polydispersity index (PDI). An example of a monodispersion i.e., a composition in which the nanoparticles have a PDI of less than 0.12 is provided.

Nanoparticles of the invention, in which multiple carboxyl groups or amino groups are present, are pH-sensitive, and examples illustrating phase transition in the order of milliseconds are provided. In one aspect, the size of the exemplified particles as dependent upon various processing parameters and pH, has been examined. Nanoparticle compositions in which the average diameter varies from 100 nm to over 300 nm are exemplified herein.

In the case of the anticancer drug doxorubicin, one example shows drug-loaded nanoparticles providing an decrease in IC50 in drug-resistant cell lines, up to 19-fold decrease being observed. A potential use of the carrier nanoparticles is thus in controlled delivery of doxorubicin for the treatment of drug resistant breast cancer.

$Gd^{+3}$-loaded nanoparticles can be used in magnetic resonance imaging (MRI) contrast agents, and this use is exemplified herein.

Use of nanoparticles having an organic fluorescent probe covalently linked to the particles is also exemplified with fluoresceinamine isomer I.

Nanoparticles of the invention have in vitro and in vivo applications. In vitro studies described herein, for example, indicate cellular uptake of the particles by cancer cells and minimal cytotoxicity towards hepatocytes, suggesting useful for drug delivery and diagnosis applications.

NMR studies of exemplified particles indicate that polysorbate 80 (PS80) is polymerized into the polymethacrylic acid grafted starch nanoparticles and present on the particle surface. Having the polethoxylated polysorbate, which has been known to exhibit surfactant properties, covalently bound to the nanoparticles provides stability to the carrier in biological systems. Moreover, PS80 is known to bind low density lipoprotein (LDL) in the blood facilitating nanoparticle crossing the blood-brain barrier via LDL receptor-mediated transcytosis. The covalently bound PS80 may impart such particles with advantageous brain targeting potential. Imaging data, in addition to our ex vivo studies described herein, provide evidence for the ability of the nanoparticles to cross blood brain barrier.

An embodiment of the invention is thus a method of producing a nanoparticle, the method comprising the steps of:
  (a) solubilising a polymer in a liquid solution;
  (b) providing a polymerizable monomer comprising a carboxylic acid side group;
  (c) graft polymerizing the monomer to form polymeric chains on the solubilised polymer,
  (d) providing ethoxylated molecules having a functional group reactive with the forming chains, wherein:

step (c) is conducted in the presence of the ethoxylated molecules to covalently link the ethoxylated molecules to the polymeric chains.

The liquid solution can include a hydroxylic solvent such as water, one or more alcohols, particularly ethanol or a mixture of water and alcohol(s), particularly water and ethanol.

The polymer can be a polyhydroxyl polymer having a degree of substitution between 0.05 and 3 per unit of the polymer, (or between 0.5 and 3, or between 1 and 3, or between 2 and 3), the monomer can include an alkenyl group, and the graft polymerizing step can be conducted in the presence of a cross-linking agent.

According to an embodiment, the monomer of step (c) is present in an amount between 1 and 20 times the amount of the cross-linking agent (mol/mol).

The step of polymerizing can be a free radical graft polymerizing process conducted in the presence of a free radical initiator. The initiator can be substantially free of transition metals. A particular initiator is persulfate or functional equivalent thereof.

The ethoxylate groups of the ethoxylated molecules can terminate in free hydroxyl groups. The ethoxylated molecules can include an alkenyl group which chemically reacts to covalently link the surfactant molecules to the polymeric chains. In a particular embodiment, ethoxylated molecules are a polyethoxylated sorbitan having a R(C9-C31)-C(O)O- group wherein the sorbitan is linked to the second polymer through a C—C covalent bond of the R(C9-C31)-C(O)O- group during the step of polymerizing. The R(C9-C31)-C (O)O-group can contain at least one C—C unsaturation which reacts to form the C—C covalent bond in the step of polymerizing.

The amount of polymer and the amount of monomer of step (c) can be selected to produce a nanoparticle in which the molar ratio of monomeric units in the polymeric chains to monomeric units of the polymer is between 0.1 and 10.

The polymerizing step can be conducted in the presence of a surfactant, often an anionic surfactant.

Embodiments include producing a nanoparticle for delivery of a biological agent in which the agent is covalently linked to the polymer of step (a). The polymer can be a polyhydroxylated polymer in which the agent is covalently linked to the polymer by substitution of a hydroxyl hydrogen atom thereof. The agent can be an organic moiety capable of complexing a metal, and the method can include forming the metal-organic moiety complex. The metal(s) can be selected to provide a signal in magnetic resonance imaging e.g., can be $Gd^{+3}$.

The amount of monomer of step (c) can be selected to be sufficiently high such that the absolute value of the zeta potential, measured at pH 7.4 and an ionic strength of 10 mM, of an aqueous solution of the nanoparticles produced is at least 15 mV.

Nanoparticles for delivery of a biological agent can be produced by dispersing the agent and nanoparticles obtained by a method of the invention in a liquid medium to incorporate the agent into the nanoparticles.

Nanoparticles for delivery of a biological agent can be produced by covalently linking to nanoparticles produced by a method of the invention and the agent to carboxylic acid groups of the polymeric chains of the nanoparticles.

According to an embodiment, the invention is a method of producing a carrier nanoparticle comprising the steps of:
  (i) solubilising a polymer in an aqueous solution;
  (ii) providing a polymerizable monomer comprising a carboxylic acid side group;

(iii) graft polymerizing the monomer to form polymeric chains on the solubilised polymer,
(iv) providing polyethoxylated molecules having a functional group reactive with the forming chains, wherein: polymerizing step (iii) is conducted in the presence of the polyethoxylated molecules to covalently link the polyethoxylated molecules to the forming chains and the polymerized product forms into the nanoparticle with polyethoxylated moieties on the exterior of the nanoparticle.

The invention includes a nanoparticle comprising: (a) a first polymer; (b) a second polymer grafted to the first polymer; and (c) a polyethoxylated moiety covalently bound to the second polymer.

In an embodiment, the second polymer of the nanoparticle can include polymerized vinyl groups having about one carboxyl group per two carbons of the backbone of the second polymer. The second polymer can be a polyalkenyl polymer. The polyalkenyl polymer can be a polyacrylic acid. According to a particular embodiment, the polyacrylic acid is poly(methacrylic acid).

The polyethoxylated moiety can be a sorbitan having a R(C9-C31)-C(O)O-group wherein the sorbitan is linked to the second polymer through a C—C covalent bond of the R-group.

The first polymer of the nanoparticle can include a polyhydroxyl polymer.

The second polymer can be crosslinked.

Embodiments include a composition containing a plurality of nanoparticles, composition can include a pharmaceutically active agent. Such an agent can be e.g., adsorbed to the nanoparticles.

A composition can include nanoparticles and a signal molecule. The signal molecule can be a metal chelated by an organic moiety, wherein the moiety is covalently bound to the nanoparticles. An organic moiety can be covalently bound to the first polymer.

The signal molecule can be covalently bound to the nanoparticles, preferably covalently linked to a carboxylic acid side group. An example of a signal molecule is a fluorophore.

A composition containing nanoparticles can further include a pharmaceutically active agent.

An embodiment includes a nanoparticle containing (I) a first polymer comprising a polysaccharide; (II) a second crosslinked polymer comprising poly(methacrylic acid) grafted to the first polymer; and (III) a polysorbate comprising a (C9-C31)R—C(O)O— group covalently bound to the second polymer by a C—C bond between the carbon backbone of the second polymer and the R group.

The (C9-C31)R—C(O)O-group of a nanoparticle can be —(C17)R—C(O)O— in which R is straight chain alkyl. The polysorbate can include the groups —O(CH$_2$CH$_2$O)$_w$—C(O)(C17)R, HO(CH$_2$CH$_2$O)$_x$—, —HO(CH$_2$CH$_2$O)$_y$—, and —HO(CH$_2$CH$_2$O)$_z$—, wherein w+x+y+z=20. The molecular weight of the polysaccharide can be between about 2,600 and about 4,500 Da.

The molar ratio of the monomeric unit of the polysaccharide to the monomeric methacrylate units of the poly(methacrylic acid) can be between 0.2 and 8.0.

The molar ratio of the polysorbate and the monomeric methacrylate units of the poly(methacrylic acid) can be between 0.002 and 0.03.

An embodiment of the invention is method of producing a nanoparticle that includes steps of:
(a) solubilising a polymer in a liquid solution;
(b) providing a polymerizable monomer comprising an alkylaminoalkyl ester side group;
(c) providing a crosslinker; and
(d) graft polymerizing the monomer to form polymeric chains on the solubilised polymer to form the nanoparticle.

The polymer can be a polyhydroxyl polymer having a degree of substitution between 0.05 and 3 per unit of the polymer, the monomer can include an alkenyl group, and the graft polymerizing step can be conducted in the presence of a cross-linking agent. The polyhydroxyl polymer can have a degree of substitution between 1 and 3 per unit of the polymer.

The polymerizable monomer can be an alkylaminoalkyl ester of methacrylic acid e.g., diethylaminoethyl methacrylic acid.

The crosslinker can be ethylene glycol dimethacrylate.

The monomer of step (d) can be present in an amount of between 1 and 200 times the amount of the cross-linking agent (mol/mol).

The amount of polymer and the amount of monomer of step (c) can be selected to produce a nanoparticle in which the molar ratio of monomeric units in the polymeric chains to monomeric units of the polymer is between 0.05 and 20 e.g., between 2 and 4.

A polysorbate can be present in step (d).

The polymerizable monomer can be present in an amount of between 5 and 50 times the amount of the polysorbate (mol/mol), or between about 10 and 40, or between about 15 and 35, or between about 20 and 30 (mol/mol).

A non-ionic stabilizer e.g., polyvinylpyrollidone can be present in step (d).

The invention includes a nanoparticle containing (i) a first polymer comprising a polysaccharide; and (ii) a second crosslinked polymer comprising an alkylaminoalkyl ester of methacrylic acid grafted to the first polymer, wherein the second polymer is crosslinked.

The second polymer can be polymerized diethylaminoethyl methacrylic acid.

The second polymer can include polymerized vinyl groups having about one carboxyl group per two carbons of the backbone of the second polymer. The polysaccharide can be a starch. The nanoparticles can be produced to exhibit an increased volume change of between 500 and 1500 fold when the pH of their ambient solution is changed from about 4 to about 7.4, or between about 600 and 1400, or between about 700 and about 1300 or between about 500 and about 1300 or between about 400 and 1100, or between about 700 and 1100, or about 800, or about 900, or about 1000, or about 1100 fold when the pH of their ambient solution is changed from about 4 to about 7.4.

PMAA-PS 80-g-St-DTPA in 0.05M NaOD. Major peaks are assigned as indicated on the molecular schemes.

Figure 4:
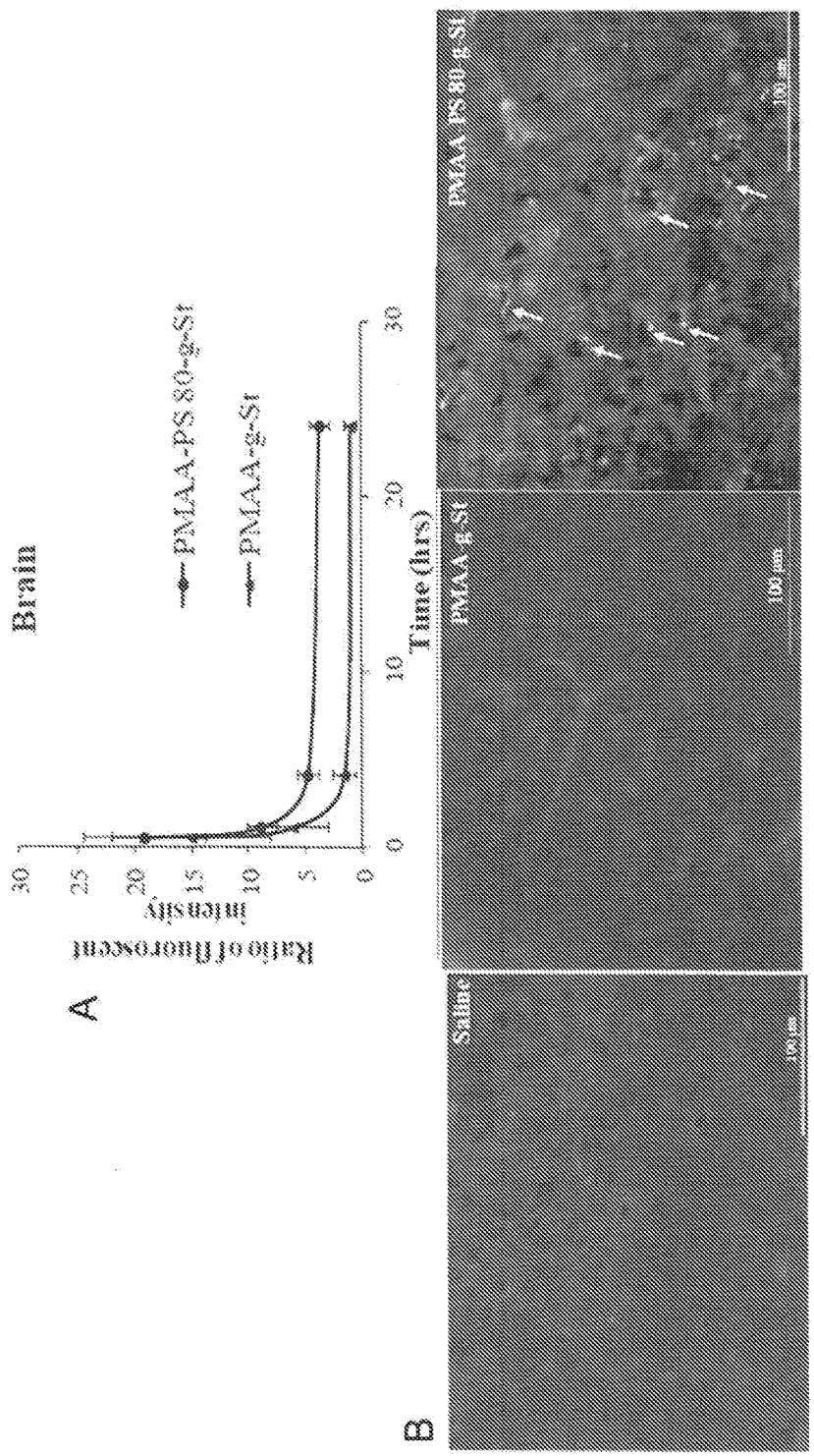

FIG. 4 shows PMAA-g-St-PS80-FITC extravasation from capillary lumen crossing the blood-brain barrier. Qualitative and quantitative results of brain distribution and accumulation for PMAA-PS 80-g-St nanoparticles. Ex vivo near infrared fluorescence images of the whole brain. (A) Ratio of the relative fluorescence intensity in brain as a function of time after intravenous (iv) injection of nanoparticles compared to normal brain not injected with nanoparticles. Data are presented as means±standard deviation (n=4). (B) Fluorescence microscopy images of perfused mouse brains 45 minutes following iv administration of saline (left), PMAA-PS 80-g-St (middle) and PMAA-PS 80-g-St (right). The particles can be detected in the perivascular regions of the brain capillaries for samples treated with PMAA-PS 80-g-St nanoparticles.

Figure 5:
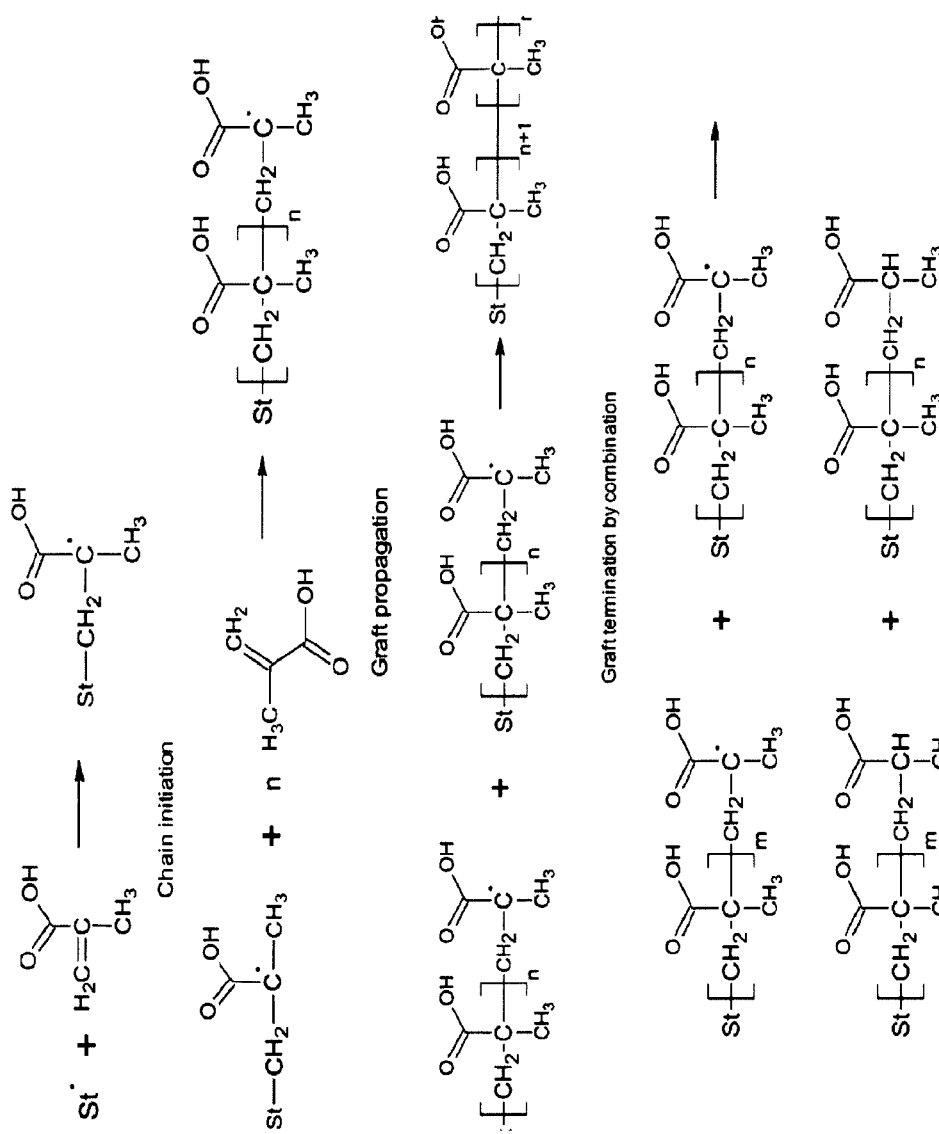

FIG. 5 is a schematic illustrating the various steps in the reaction scheme of terpolymer synthesis.

Figure 6:
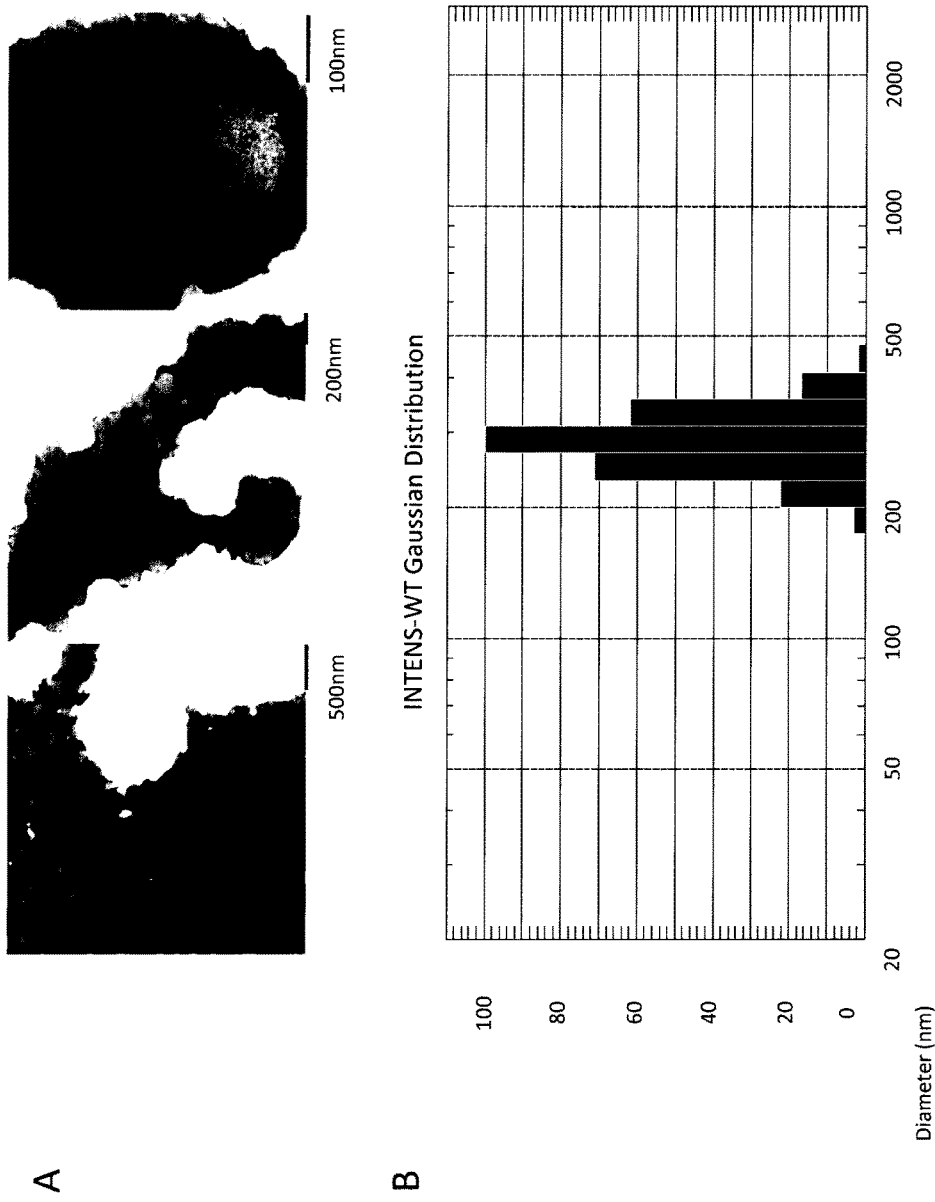

FIG. 6 shows: (A) TEM images of PMAA-g-St-2 in 0.15 M PBS of pH=7.4. The nanoparticles were stained with ammonium molybdate and dried-on carbon-coated grid. (B) Intensity-weighted hydrodynamic diameter of the nanoparticles in 0.15 M pH 7.4 PBS. The particles showed a Gaussian distribution and were relatively monodispersed.

Figure 7:
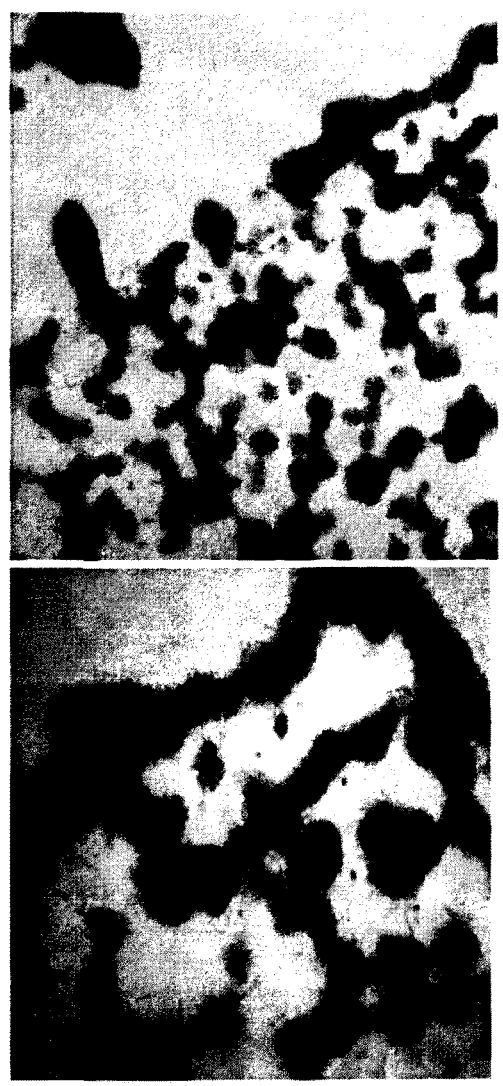

FIG. 7 shows TEM images of PDEAEM-g-St-2 nanoparticles.

Figure 8:
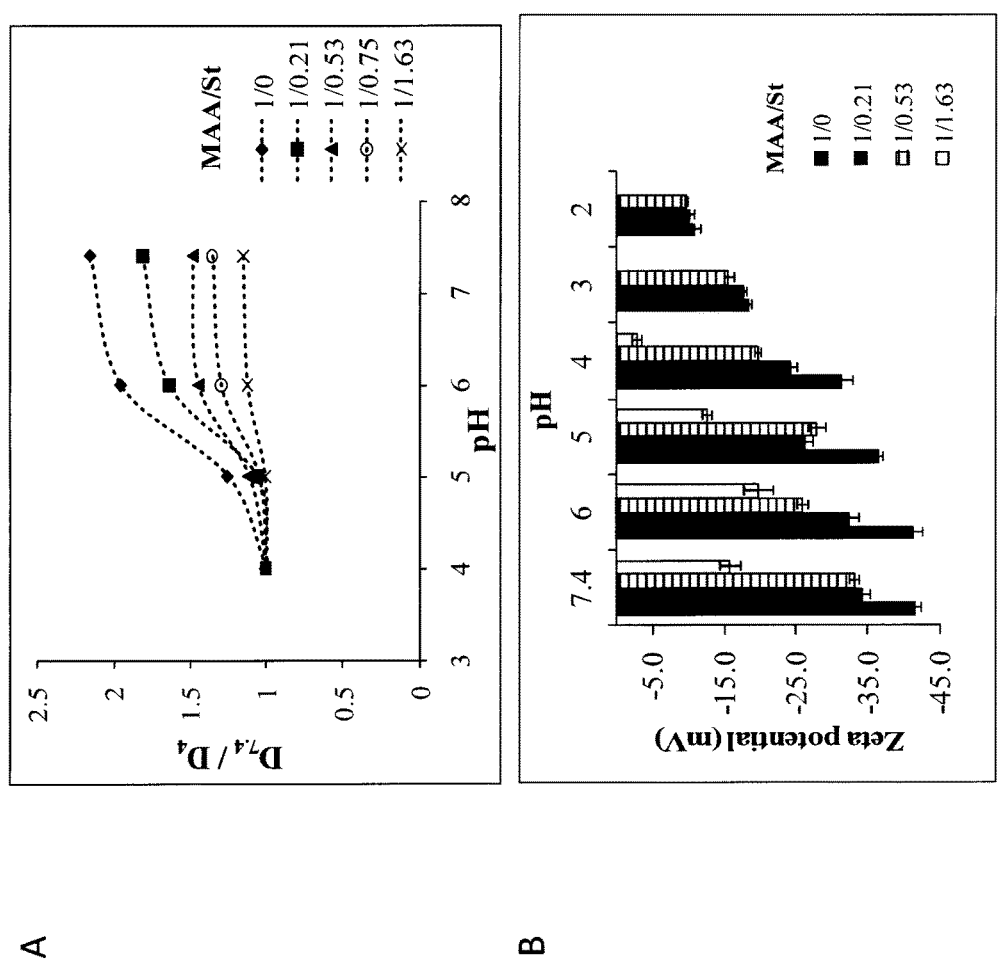

FIG. 8 shows: (A) relative diameter vs. pH for the nanoparticles with different feed molar ratio of MAA/St in 0.15 M PBS. $D_{7.4}$ and $D_4$ are particles diameter at pH 7.4 and 4 respectively. (B) Effect of pH on surface charge for particles of various MAA/St molar ratio. The ionic strength was kept constant at 10 mM using NaCl. Data points represent the mean±standard deviation of three independent measurements.

Figure 9:
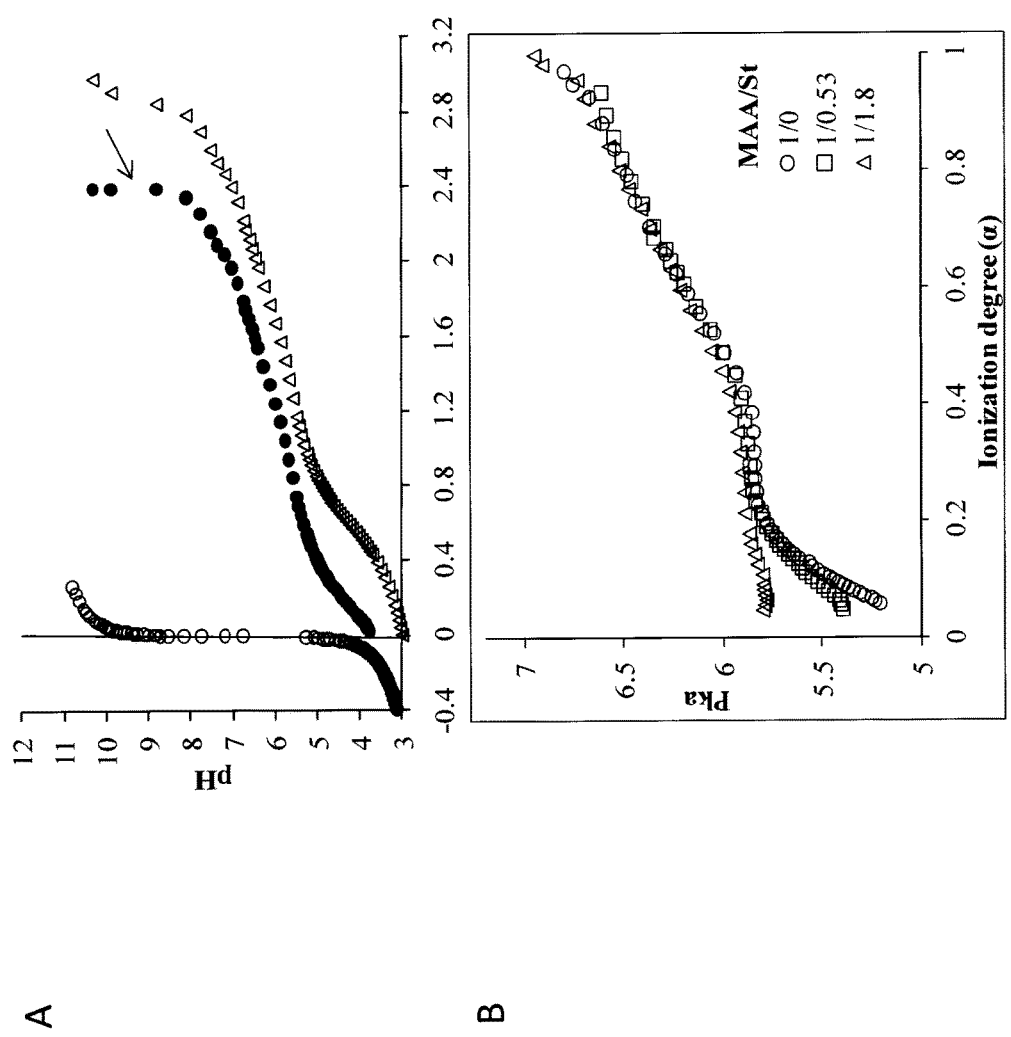

FIG. 9 shows: (A) potentiometric titration curves. Empty triangles represent the uncorrected potentiometric titration curve for PMAA-g-St-2 latex dispersion. Solid content=0.104 wt %, $C_s$=0.05N NaCl, [NaOH]=0.1 N, [HCl]=0.1N. Filled circles represent the titration curve after correction. Empty circles show the blank titration curve. The arrow represents the equivalence point. The equivalence points are used to calculate the MAA contents in various nanoparticle batches. (B) Variation in the apparent dissociation constant ($pK_a$) as a function of the degree of ionization ($\alpha$) for nanoparticles of different starch and MAA contents.

Figure 10:
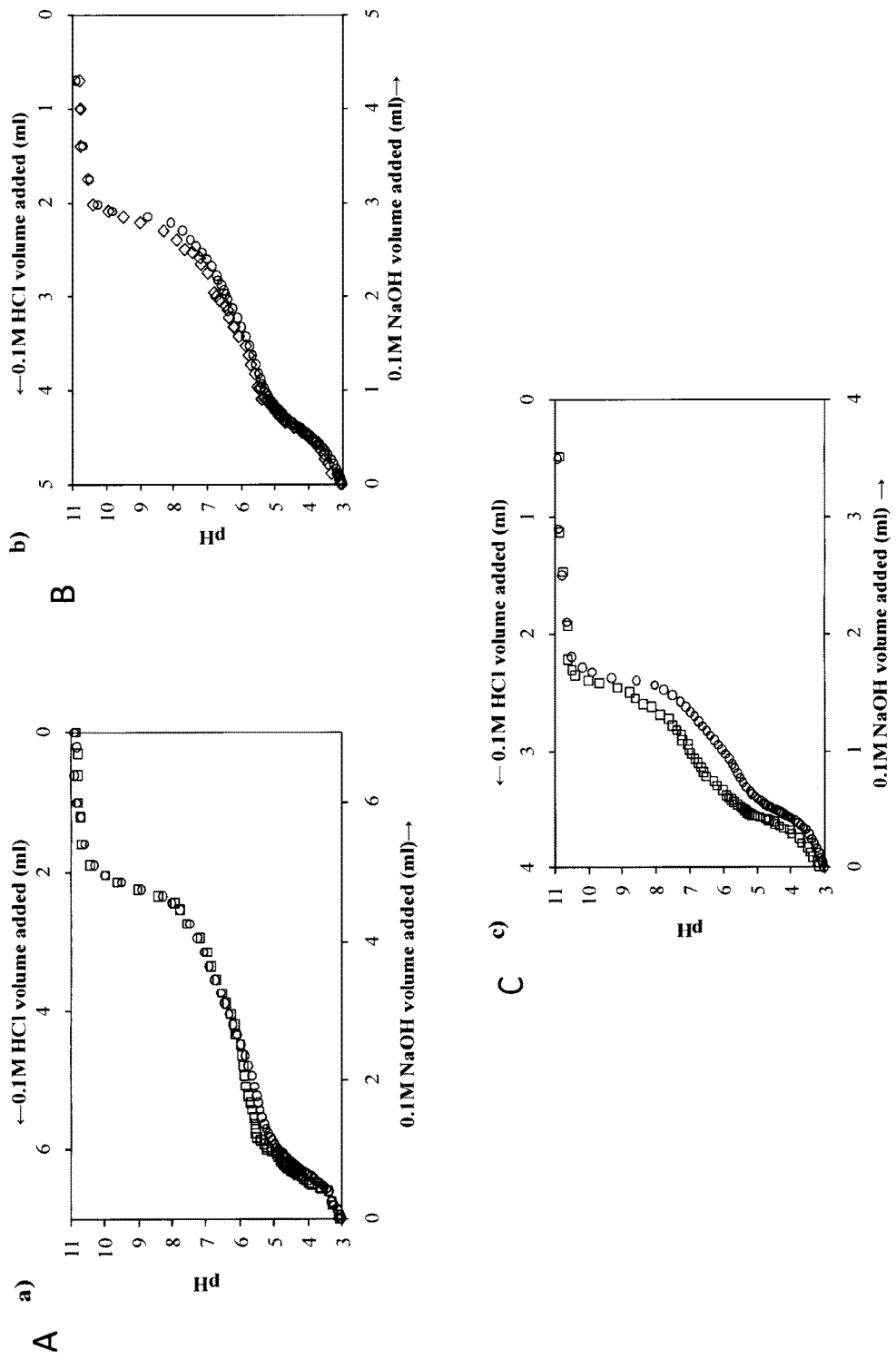

FIG. 10 shows forward and backward potentiometric titrations using stabilization time of 30 s between injections. (A) PMAA, (B) PMAA-g-St-2, (C) PMAA-g-St-4. A lag time between forward and backward titrations was observed only in case of nanoparticles with high starch content.

Figure 11:
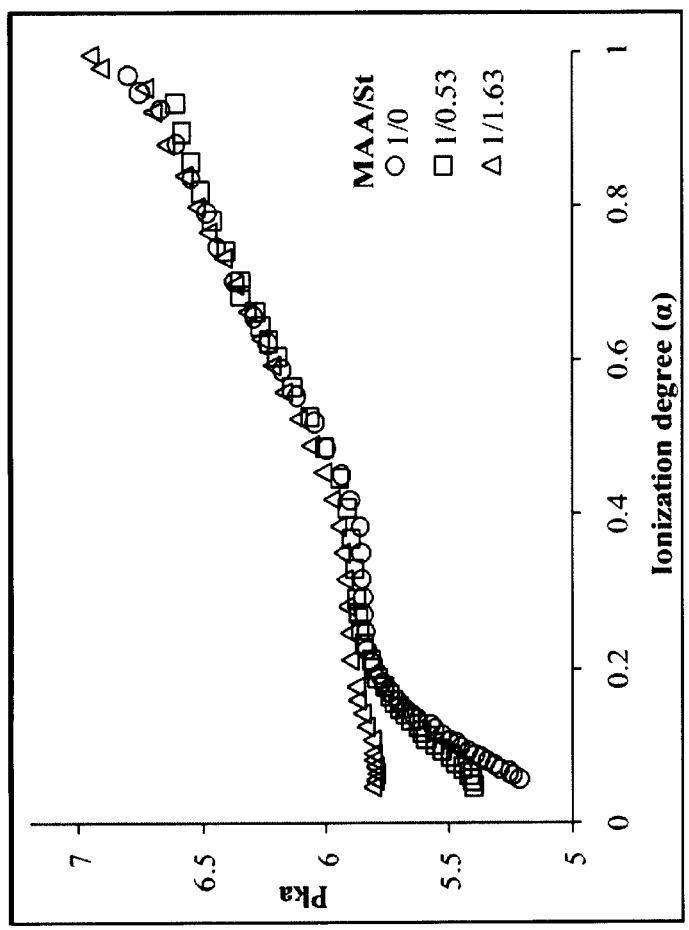

FIG. 11 shows variation in the apparent dissociation constant ($pK_a$) as a function of the degree of ionization ($\alpha$) for nanoparticles of various starch and MAA contents.

Figure 12:
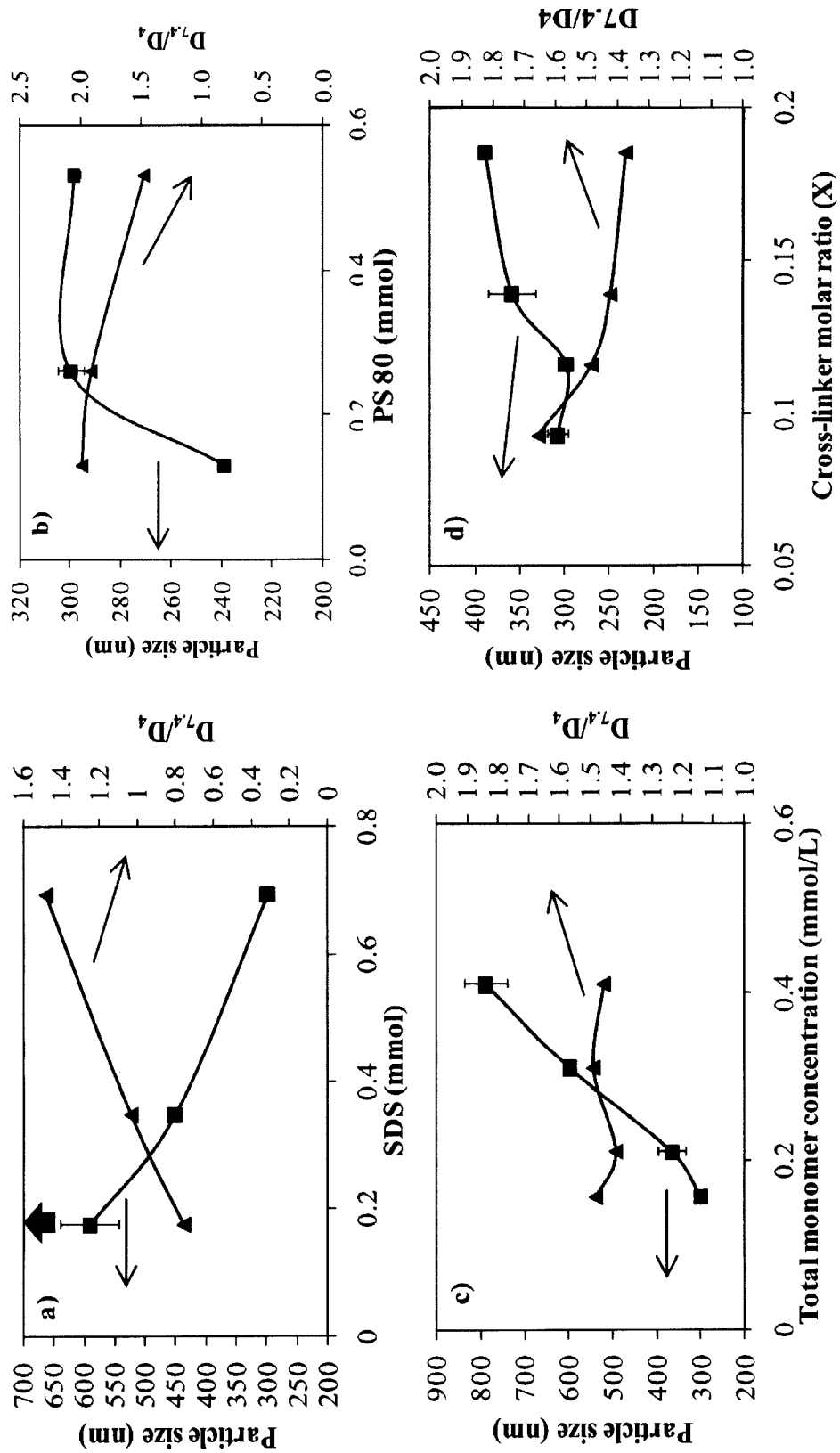

FIG. 12 shows effects of (A) SDS, (B) PS 80, (C) total monomer concentration, and (D) cross-linker molar ratio on particle size and pH sensitivity. Filled squares represent particle size and filled triangles represent relative particles diameter. Data points represent the mean±standard deviation of three independent measurements.

Figure 13:
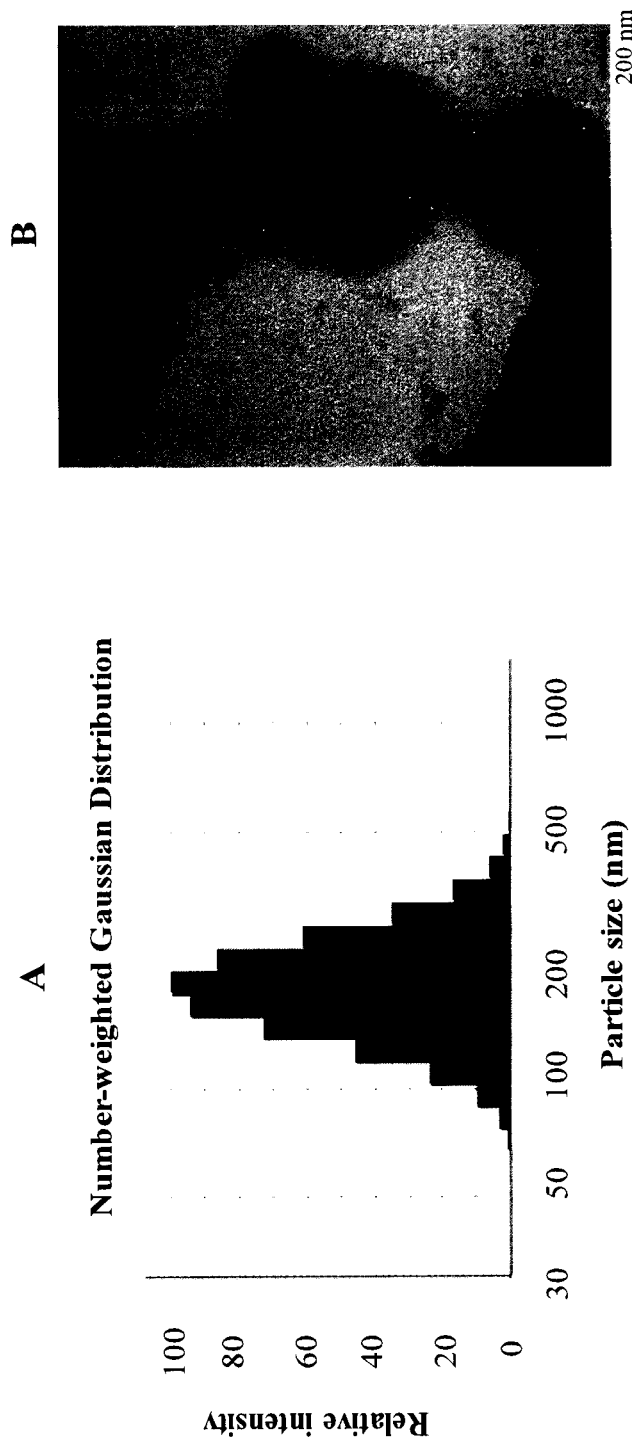

FIG. 13 shows (A) number-weighted Gaussian distribution of PMAA-PS 80-g-St nanoparticles loaded with doxorubicin (LC=33%) in 0.15 M phosphate buffer at pH 7.4, and (B) transmission electron micrograph (TEM) of doxorubicin-loaded nanoparticles (LC=33%).

Figure 14:
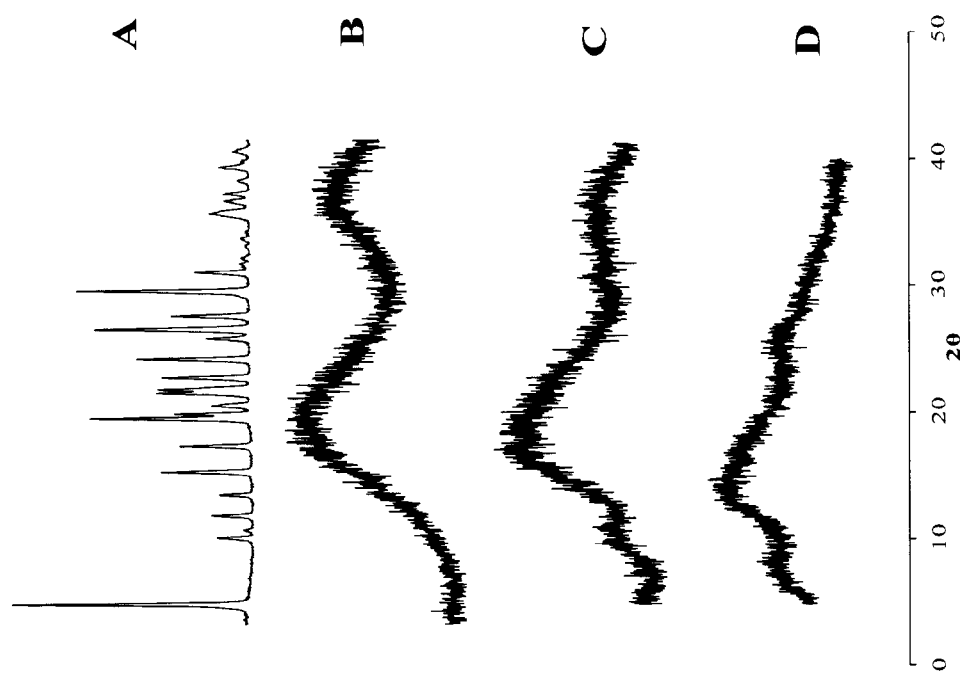

FIG. 14 shows XRD spectrum of (A) doxorubicin in native form, (B) PMAA-PS 80-g-St nanoparticles, (C) doxorubicin-loaded nanoparticles (LC=50%), and (D) doxorubicin-loaded nanoparticles (LC=50%) after 6 months storage at room temperature. For doxorubicin clear peaks are visible in the diffractogram indicating the presence of crystalline phase in the native form whereas nanoparticles show a typical amorphous pattern. Absence of peaks in the diffractograms of doxorubicin-loaded nanoparticles indicates the phase transformation of crystalline doxorubicin to amorphous doxorubicin.

Figure 15:
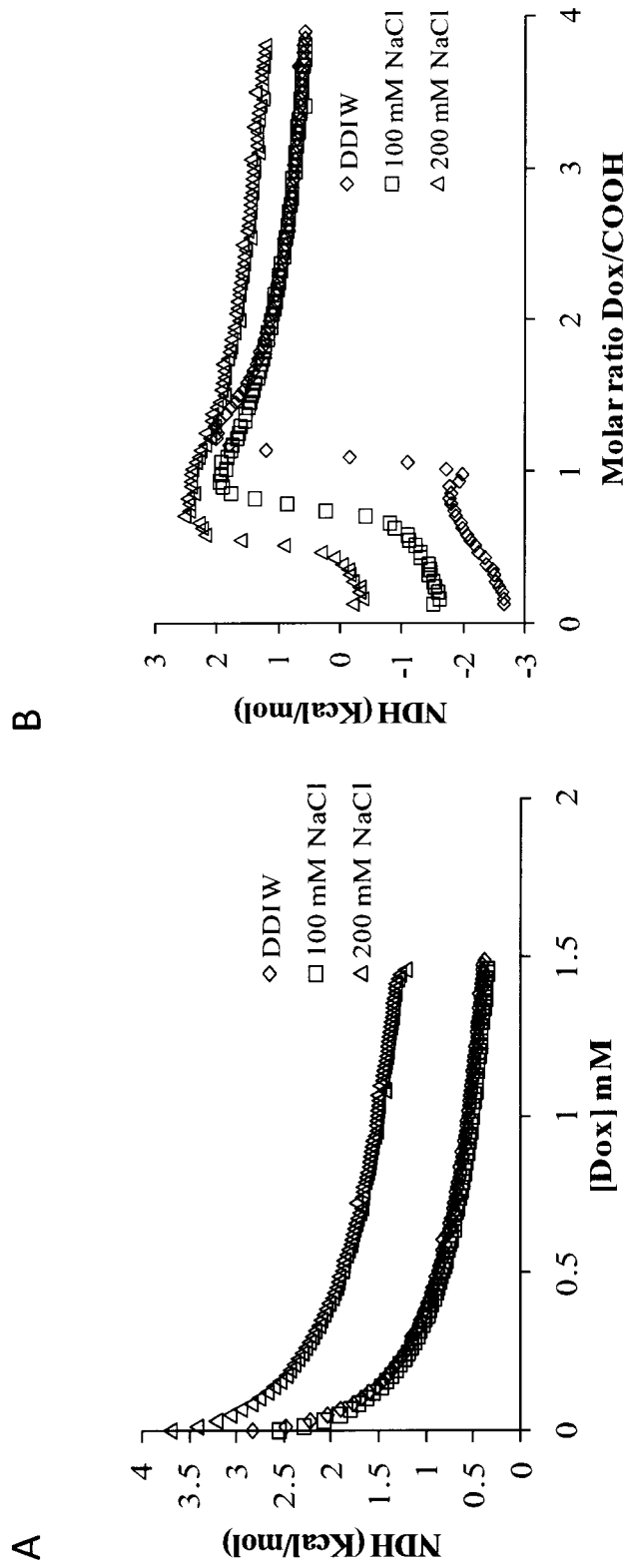

FIG. 15 shows graphical data for the interaction between doxorubicin and carboxylic acid groups of nanoparticles having maximum stoichiometry of 1. (A) The blank differential enthalpy curves of titrating 8.5 mM doxorubicin in DDIW with various NaCl content. (B) Differential enthalpy curves of titrating 8.5 mM doxorubicin into 0.1 mg/ml PMAAg-St-PS80 nanoparticles in DDIW with various NaCl content of various pH.

Figure 16:
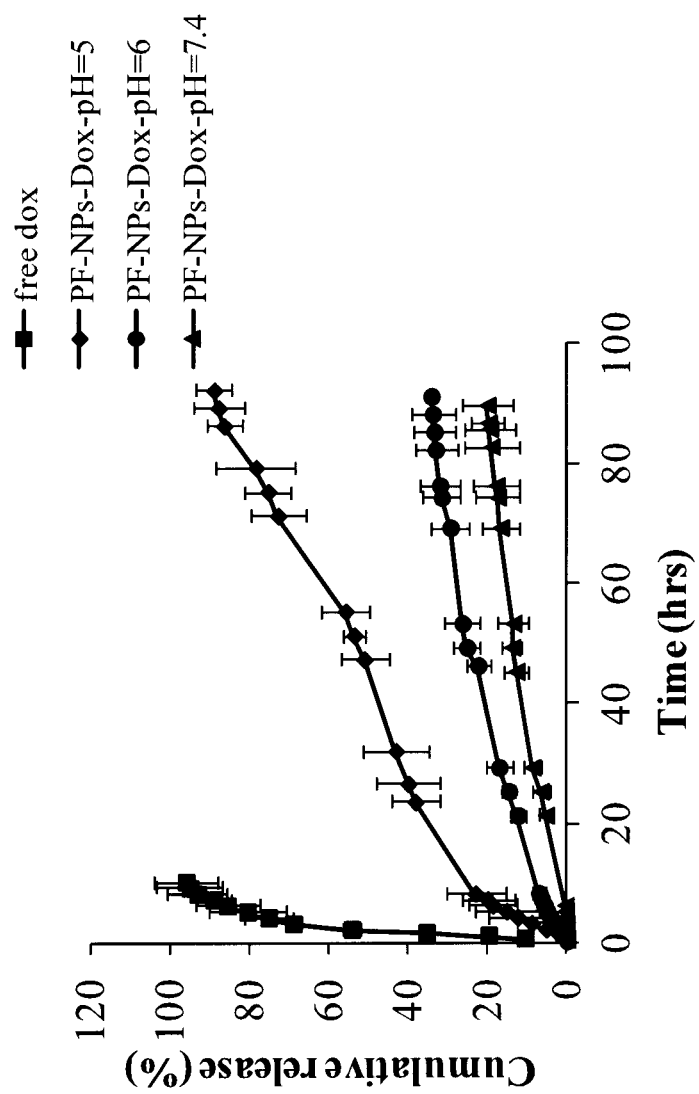

FIG. 16 shows pH-dependent doxorubicin release from the nanoparticles. The effects of pH on kinetics of doxorubicin release from the nanoparticles having a drug loading content of 50% at 37° C. are indicated. The release of free doxorubicin from the dialysis bag was used as control. For each buffer system, the ionic strength was kept constant at 0.15 M by adding NaCl.

Figure 17:
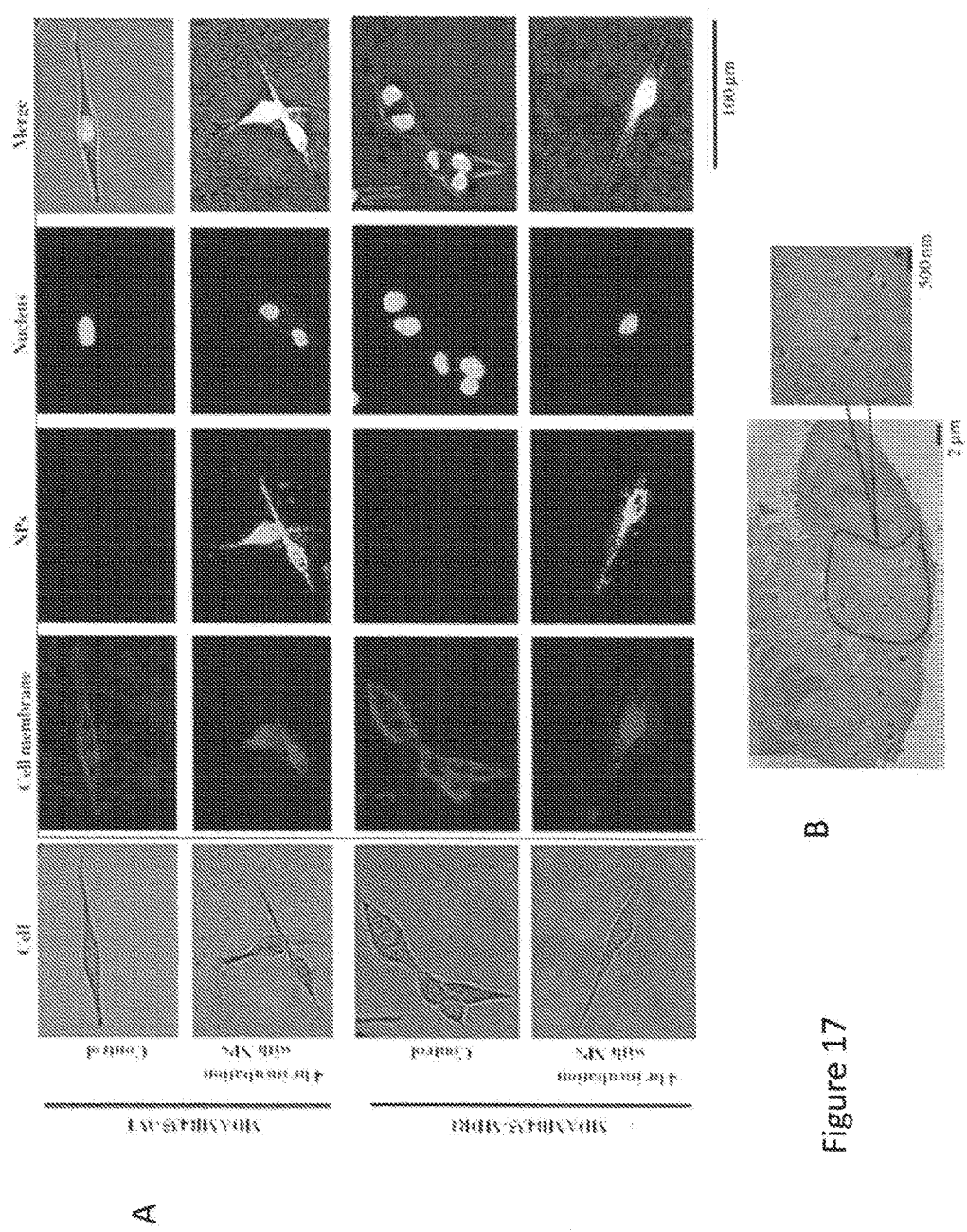

FIG. 17 shows (A) fluorescence microscopy images of MDA-MB435/LCC6 cells (both wild-type (WT) and multidrug resistant (MDR1) with and without (control) 4 hr incubation with fluorescent NPs. Nuclei were stained with Hoescht 33342 and visualized with DAPI filters, cell membranes were stained with Vybrant™DiI and visualized with Cy3 filters, and NPs were labelled with fluoresceinamine isomer I and visualized with FITC filters. Optical slices were taken every 2 μm from the uppermost and lowermost regions of the cell, allowing for selection of an image at approximately the midpoint of the nucleus. (B) TEM micrographs of MDA-MB435/LCC6 cells treated with 0.25 mg/ml PMAA-PS 80-g-St NPs for 4 hrs. The nanoparticles were loaded with gadolinium ions (metal) and appear as electron dense deposits. Area indicated by dotted line in image on the left is magnified in the image on the right.

Figure 18:
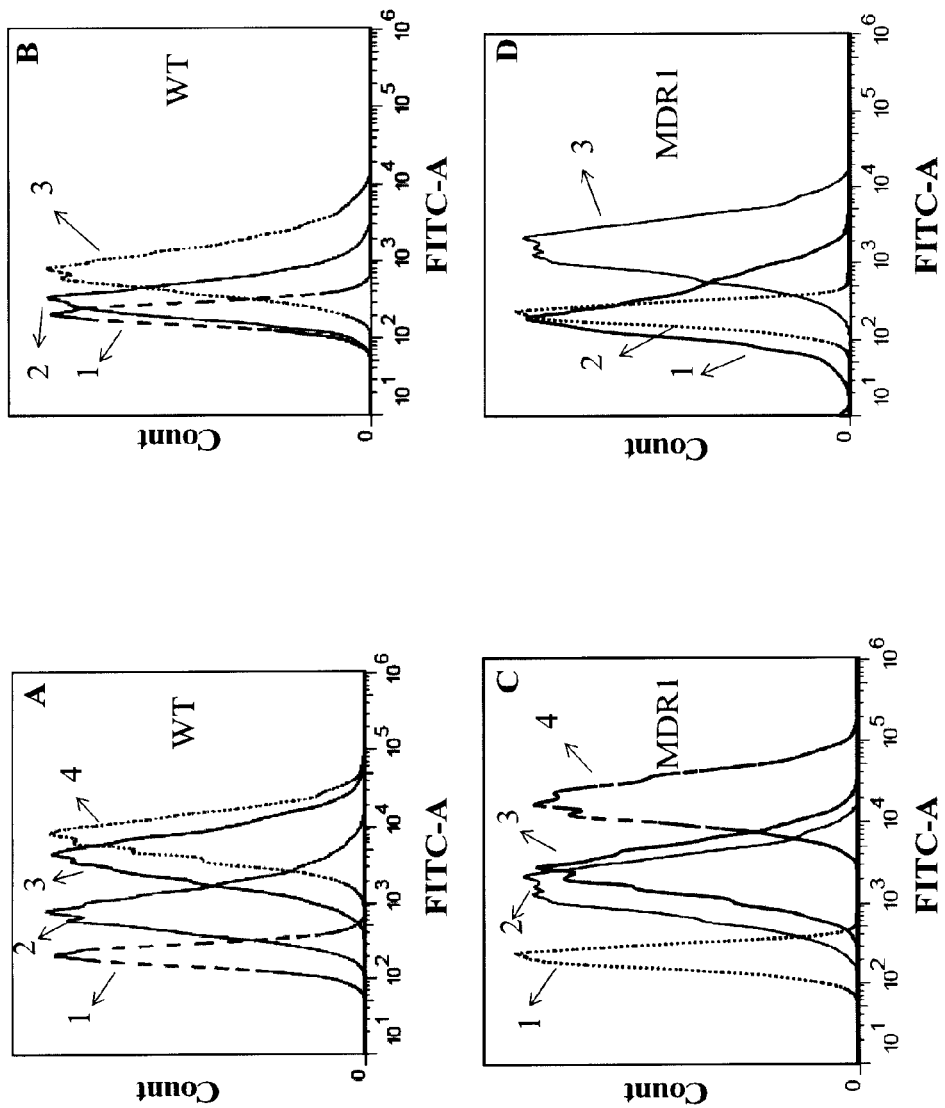

FIG. 18 shows the nanoparticles are effectively endocytosed by wild-type and drug-resistant human breast cancer cells. Flow cytometry histograms for MDA-MB435/LCC6 cells indicate the effect of incubation time and temperature on particle uptake. The cells were incubated with fluorescently labelled nanoparticles at the final nanoparticle concentration of 0.25 mg/ml at 37° C. (A) MDA-MB435/WT (1) background, (2) 1 hr incubation, (3) 4 hrs incubation, (4) 24 hrs incubation. (B) MDA-MB435/WT (1) background, (2) 4° C., (3) 24° C. (C) MDA-MB 435/MDR1 (1) background, (2) 1 hr incubation, (3) 4 hrs incubation, (4) 24 hrs incubation. (D) MDA-MB435/MDR1 (1) background, (2) 4° C., (3) 24° C. Excitation using 488 nm argon ion laser and emission monitored at 530 nm.

Figure 19:
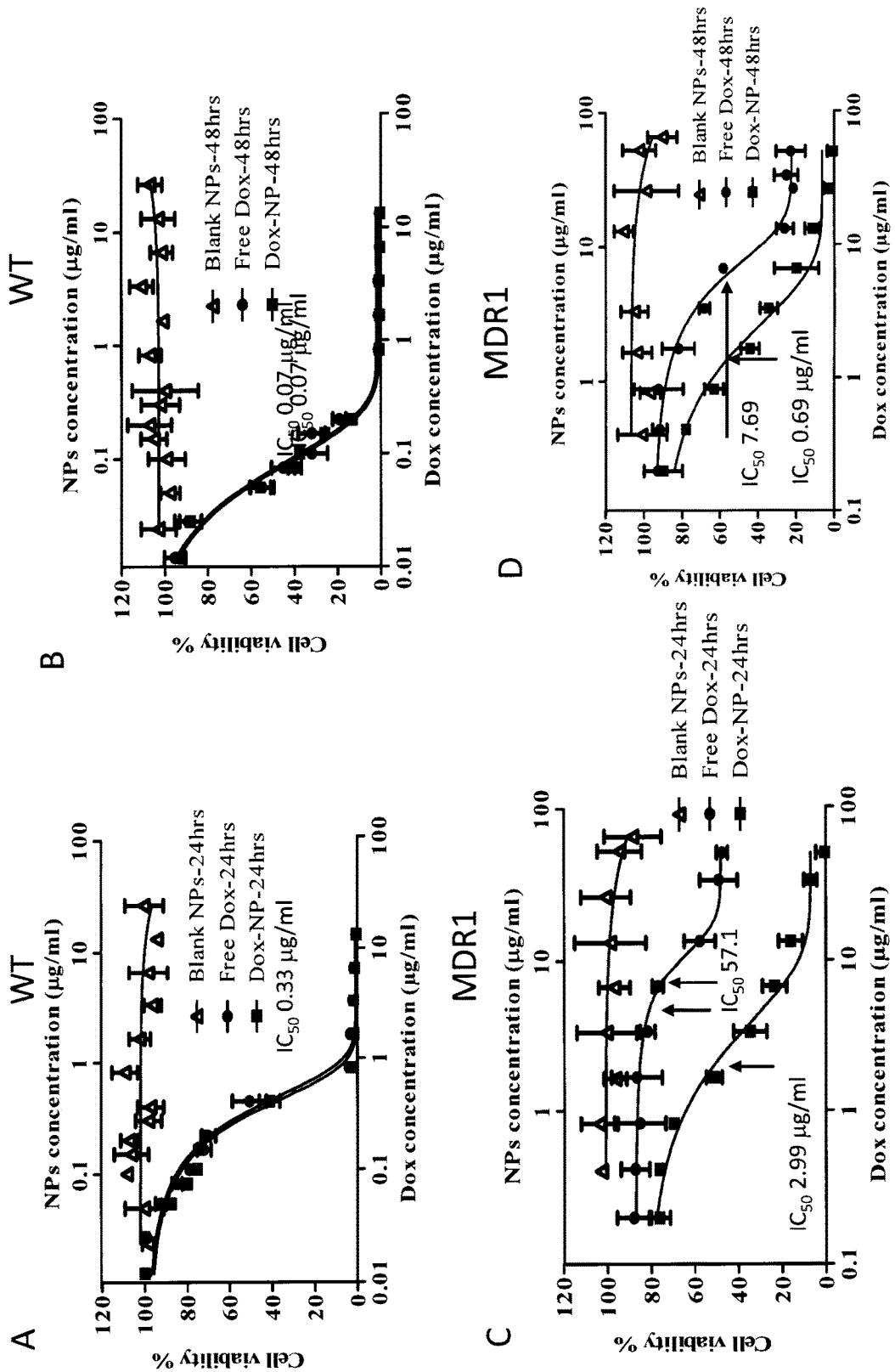

FIG. 19 illustrates doxorubicin-loaded nanoparticles exhibit significantly lower IC50 values in MDR1-expressing human breast cancer cells. The response of MDA-MB435/LCC6 cell types to free doxorubicin and doxorubicin-loaded nanoparticles by MTT assay was determined. (A-B) Cell viability of MDA-MB435/LCC6/WT (n=3) cells after exposure to increasing concentrations of free doxorubicin and doxorubicin loaded nanoparticles for 24 hrs (A) and 48 hours (B). (C-D) Cell viability of MDA435/LCC6/MDR1 (n=3) cells after exposure to increasing concentrations of free doxorubicin and drug loaded nanoparticles for 24 hrs (C) and 48 hrs (D). Cells with no treatment and incubated with blank nanoparticles were used as control for free drug and drug loaded nanoparticle respectively. Cell viability is expressed as the percent of control for each treatment group. Data points represent the mean±standard deviation of the number of trials indicated for each experiment.

Figure 20:
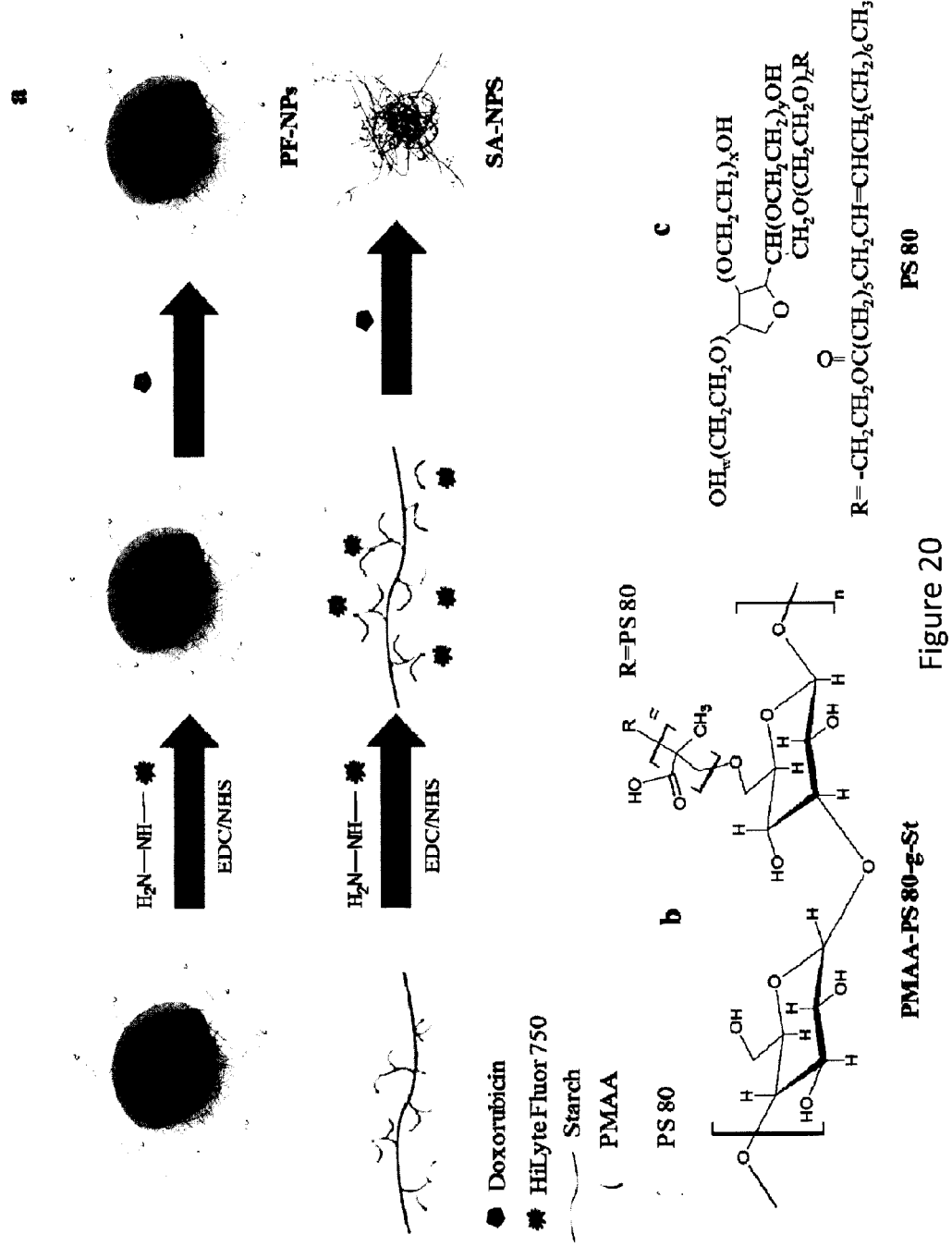

FIG. 20 shows (A) TEM images of SA-NPs and PF-NPs. (B) Dye-conjugated nanoparticles show NIR fluorescence characteristics. (C) Summary of physicochemical properties of SA-NPs and PF-NPs. Particle diameter refers to the number-weighted diameter of readings averaged over 5 minutes. Loading efficiency (LE %) is the fraction of originally added drug that was incorporated into the NPs, whereas drug loading content (LC %) is the percent of drug weight to total weight of the nanoparticles. All values are described as the mean±standard deviation of three independent trials. Total amount of Dox in the loading solution was 1.25 mg.

Figure 21:
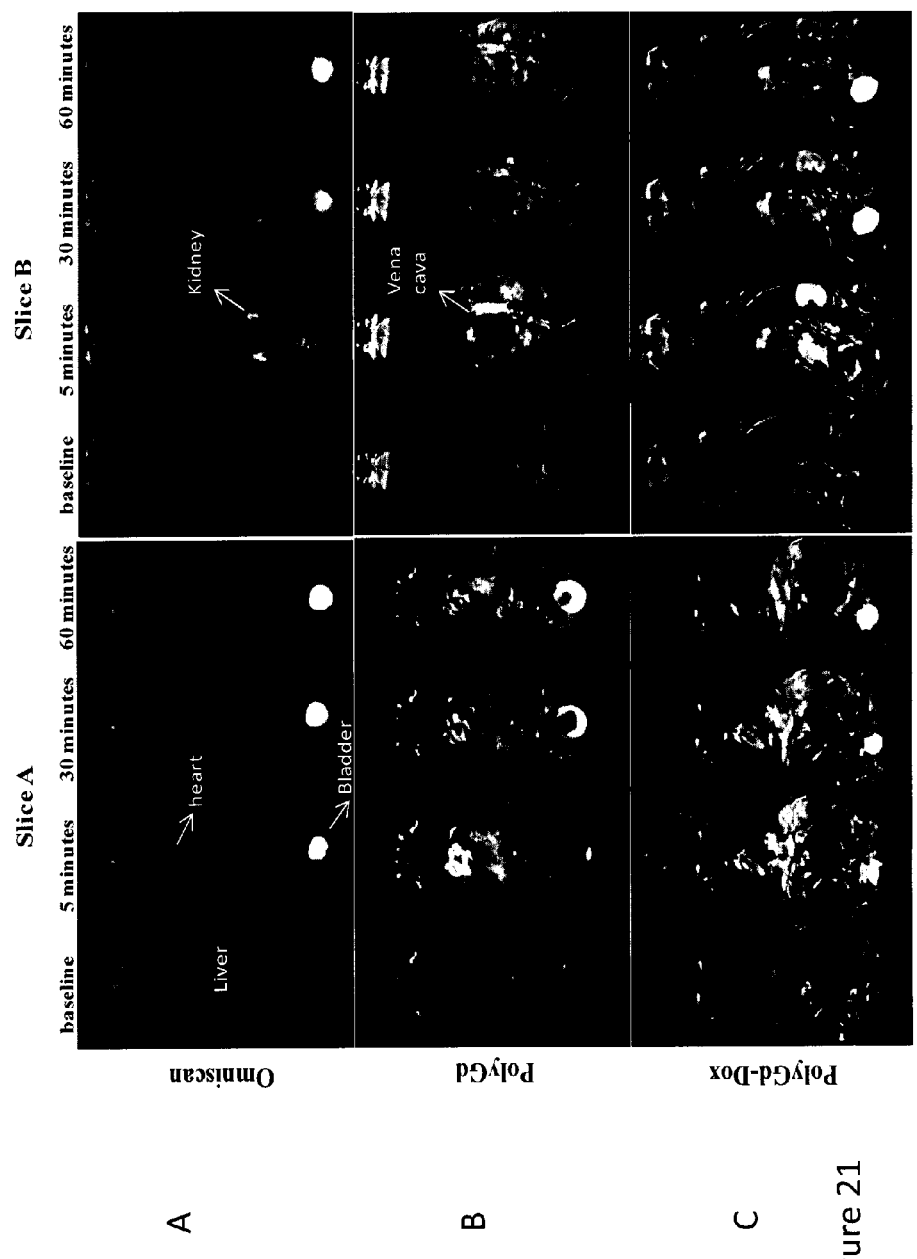

FIG. 21 shows coronal $T_1$-weighted (3D-FLASH, TE/TR 3/25 msec, flip angle 20°) whole body images of Balb/c mice injected with (A) Omniscan® (0.1 mmol/kg $Gd^{3+}$), (B) PolyGd (0.025 mmol/kg $Gd^{3+}$), and (C) PolyGd-Dox (0.025 mmol/Kg $Gd^{3+}$). Heart, liver, bladder are represented in Slice A. Slice B shows kidneys, and vena cava. At one-fourth the dose of Omniscan®, PolyGd and PolyGd-Dox produce much higher contrast over an extended period of time.

Figure 22:
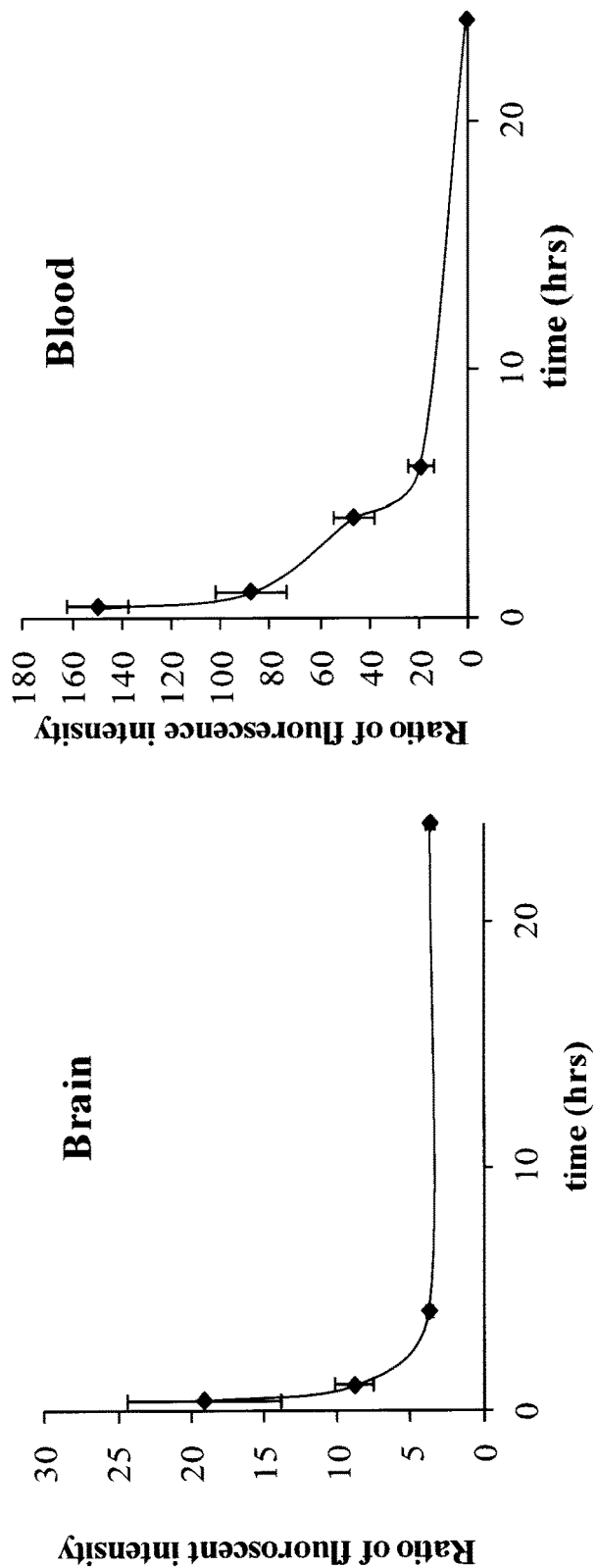

FIG. 22 shows the ratio of fluorescent intensity (normalized against baseline) for brain (left) and blood (right); the data provide evidence for the deposition of the PMAA-g-St-PS80 in the brain.

Figure 23:
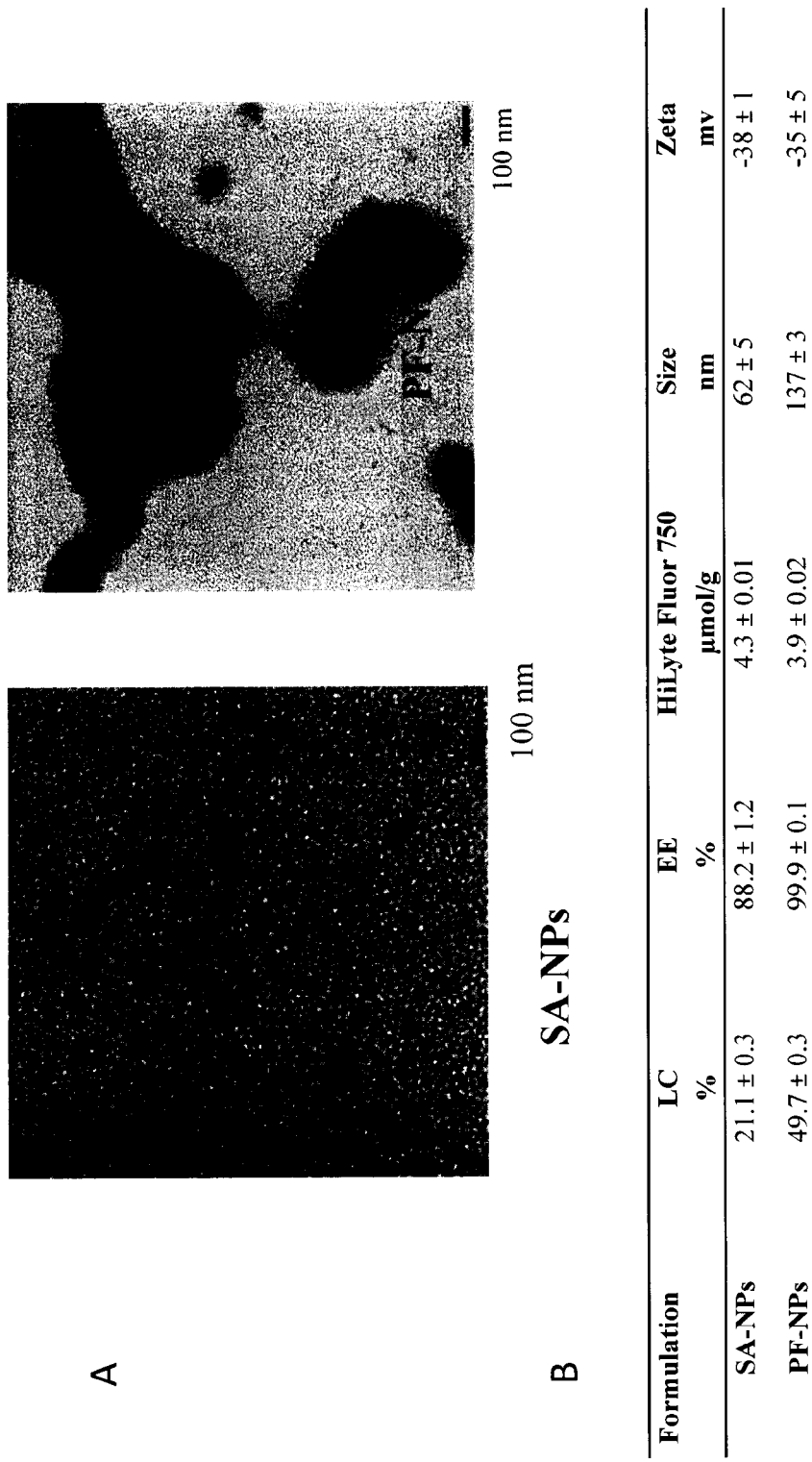

FIG. 23 shows (A) TEM images of SA-NPs and PF-NPs. (B) Summary of physicochemical properties of SA-NPs and PF-NPs. Particle diameter refers to the number-weighted diameter of readings averaged over 5 minutes. Loading efficiency (LE %) is the fraction of originally added drug that was incorporated into the NPs, whereas drug loading content (LC %) is the percent of drug weight to total weight of the nanoparticles. All values are described as the mean±standard deviation of three independent trials. Total amount of Dox in the loading solution was 1.25 mg.

Figure 24:
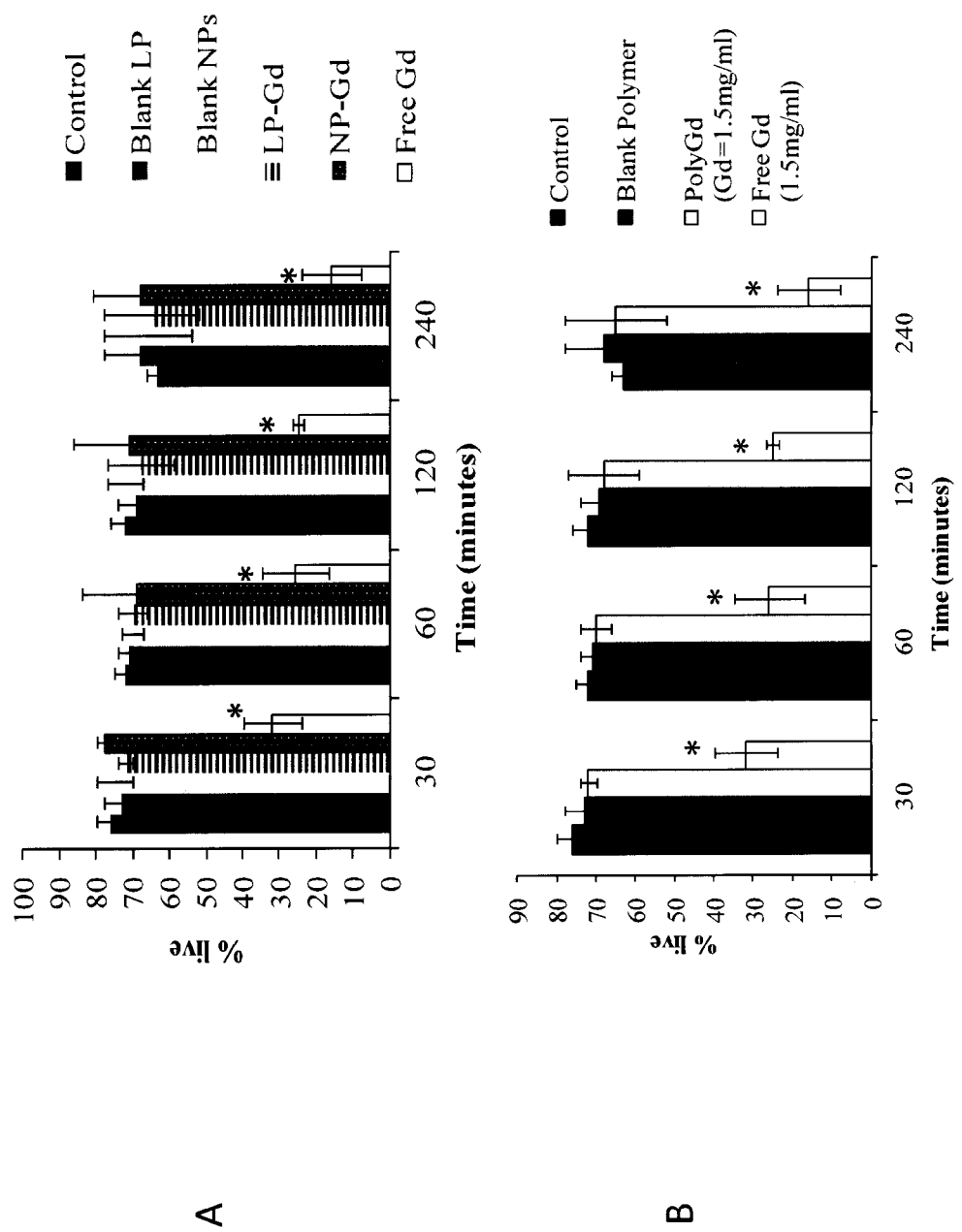

FIG. 24 shows (A) in vitro cytotoxicity of blank linear polymer and nanoparticles, $Gd^{3+}$ loaded polymer and nanoparticles, and free $Gd^{3+}$ in rat hepatocytes using trypan blue exclusion assay. Loading of $Gd^{3+}$ into the linear polymer and nanoparticle significantly reduced the $Gd^{3+}$ toxicity in the cells (* statistically significant compared to control (p<0.05)). (B) The toxicity of saline (black), blank polymer (dark gray), PolyGd (light gray) and free $Gd^{3+}$ (white) to rat hepatocytes in culture exposed for 30 min, 60 min, 120 min, or 240 min. "% live" represents the percent of hepatocytes excluding trypan blue. The means and standard deviations of three trials are shown. An asterisk (*) denotes a significant difference (p<0.05) in survival values compared to the control.

Figure 25:
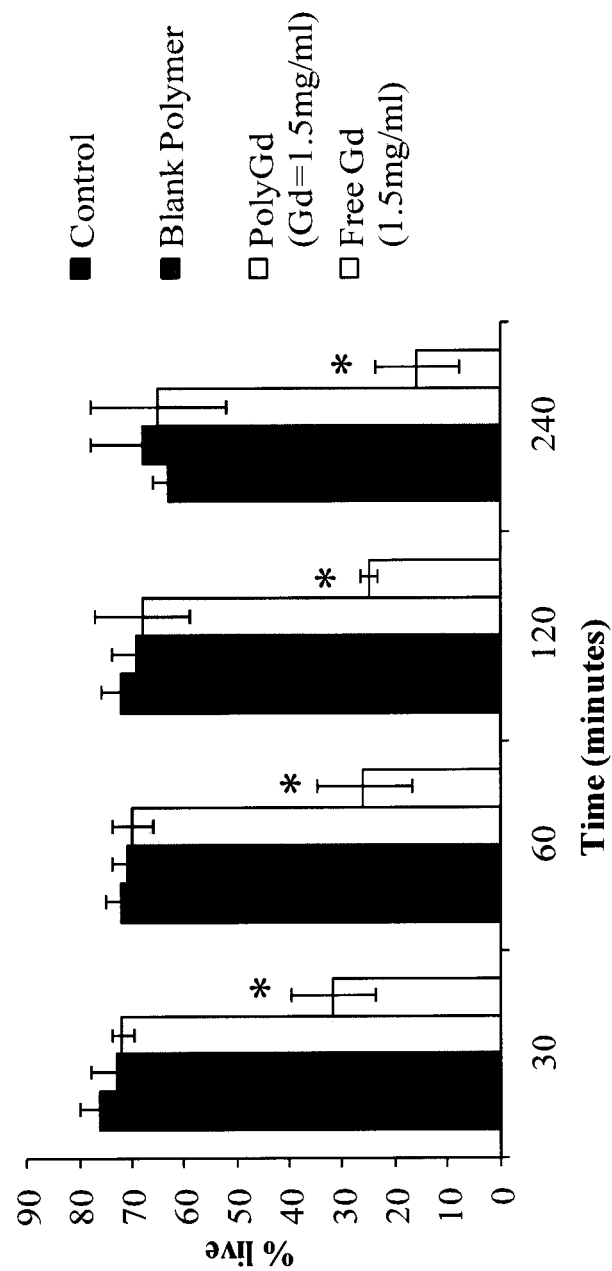

FIG. 25 shows the toxicity of saline (black), blank polymer (dark gray), PolyGd (light gray) and free $Gd^{3+}$ (white) to rat hepatocytes in culture exposed for 30 min, 60 min, 120 min, or 240 min. "% live" represents the percent of hepatocytes excluding trypan blue. The means and standard deviations of three trials are shown. An asterisk (*) denotes a significant difference (p<0.05) in survival values compared to the control.

Figure 26:
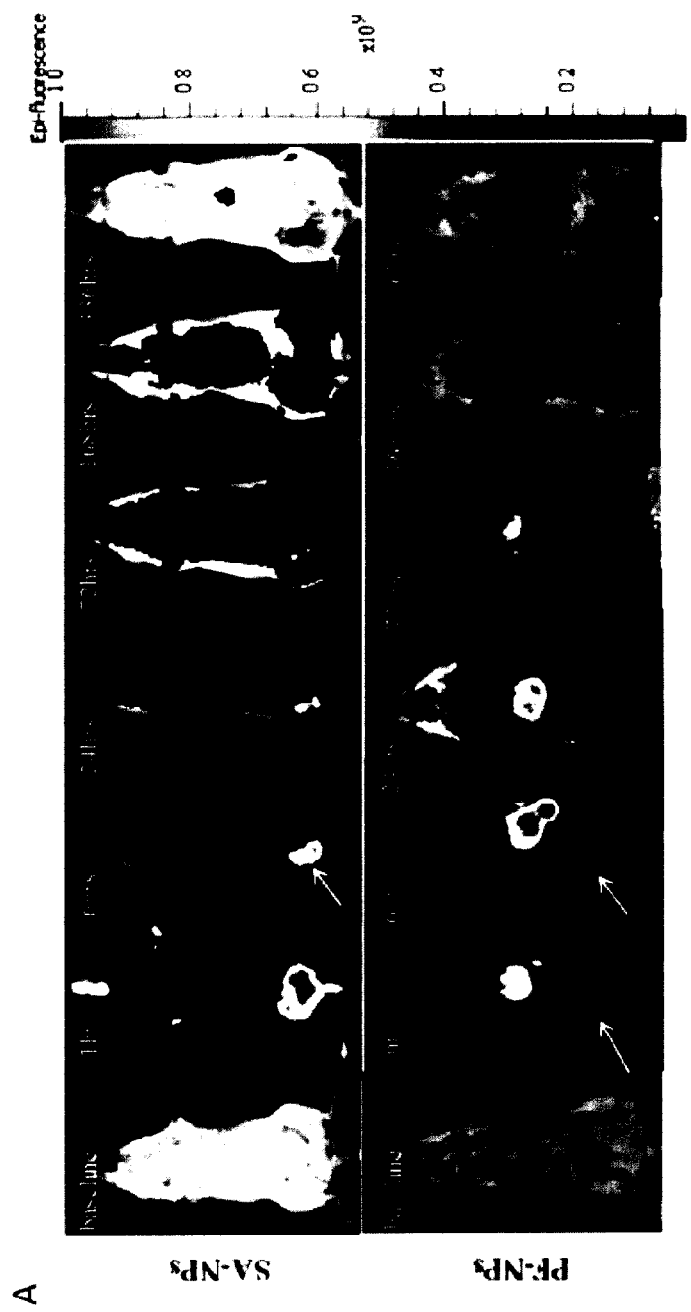
Figure 26:
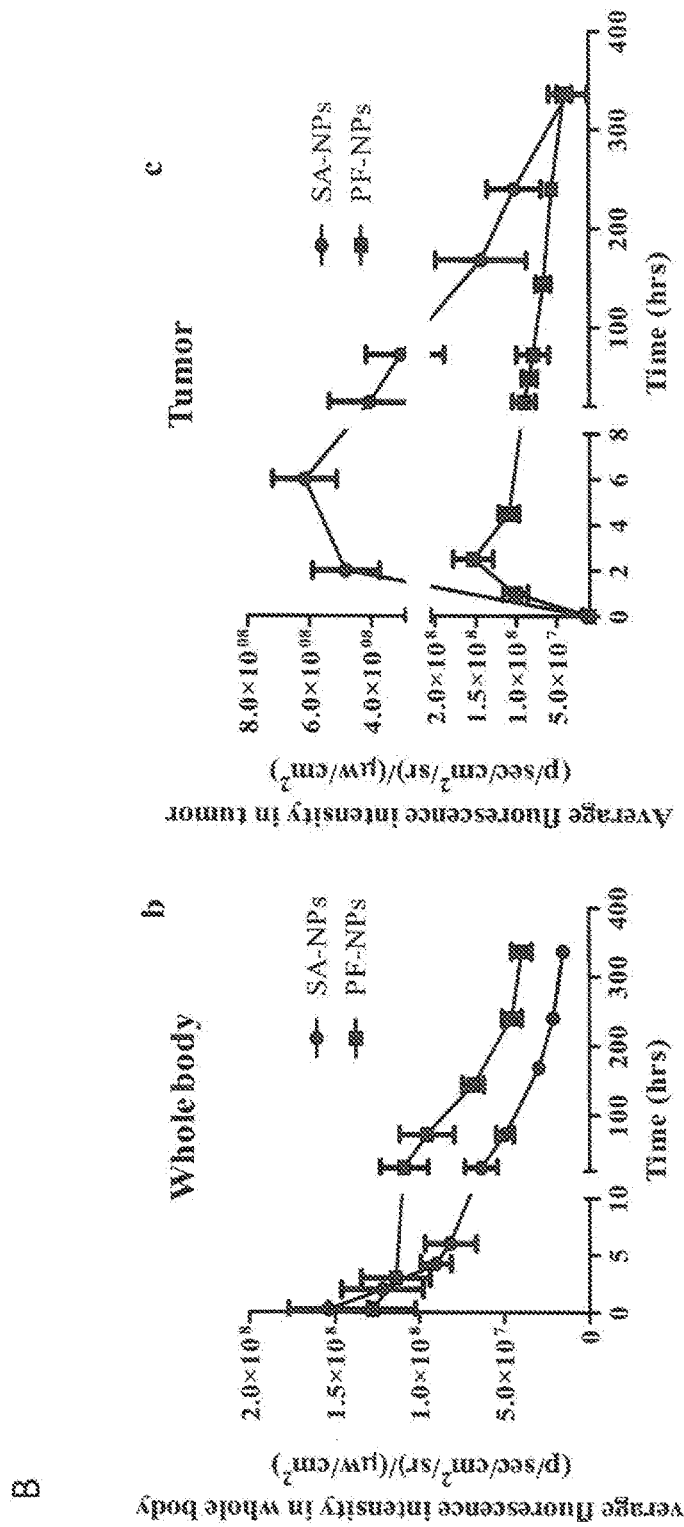

FIG. 26 shows (A) whole animal real time biodistribution and tumor targeting of SA-NPs and PF-NPs in mice bearing an orthotopic breast tumor model. Nanoparticle-associated fluorescence was determined prior to intravenous injection (baseline), and then at various hours following nanoparticles injection up to 14 days. Tumor is indicated with an arrow. (B) Time-dependent excretion profiles of SA-NPs and PF-NPs from the whole body (left) and tumor (right). The fluorescence intensity for the region of interest was recorded as average radiant efficiency. Data are presented as means±standard deviation (n=2×3). C)

Figure 27:
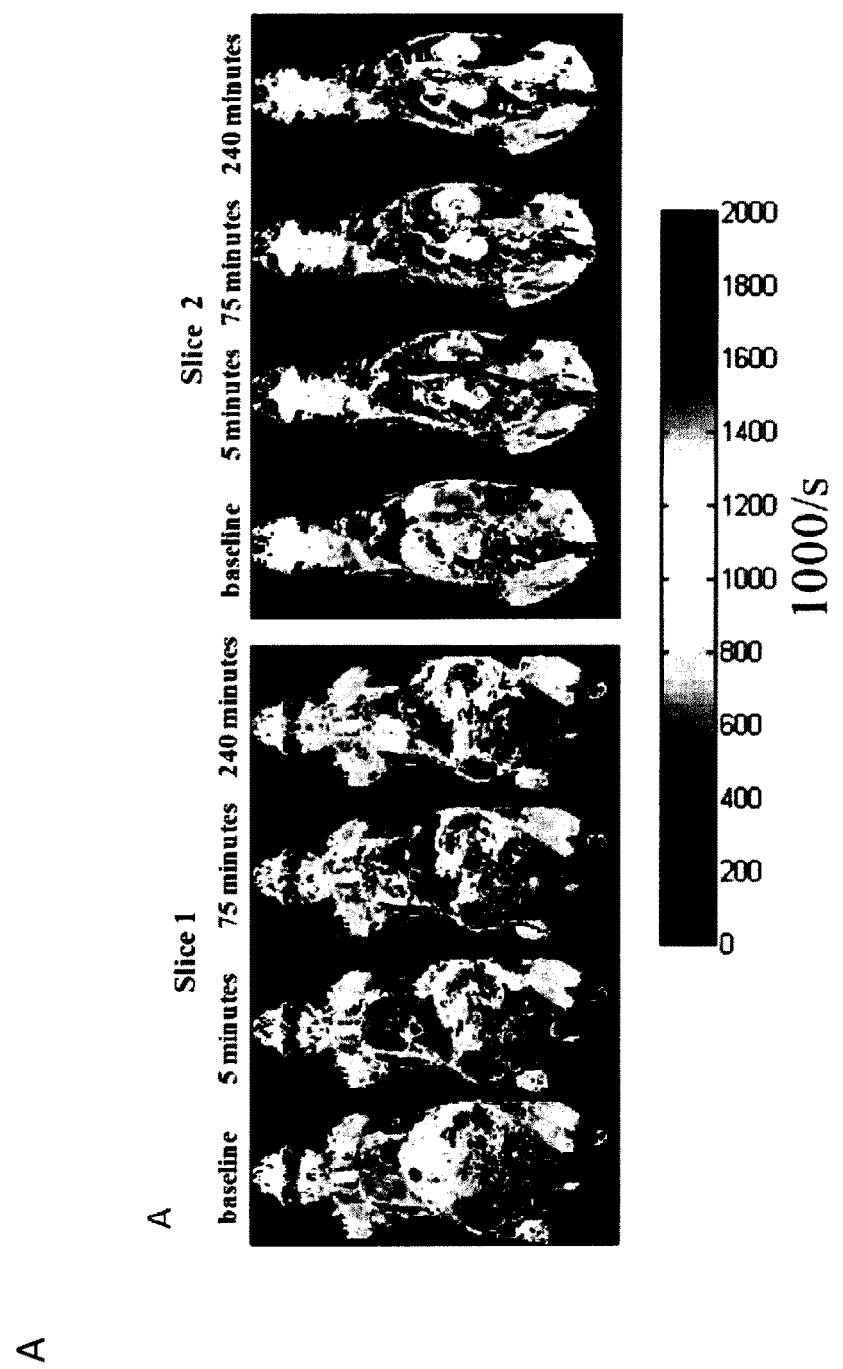
Figure 27:
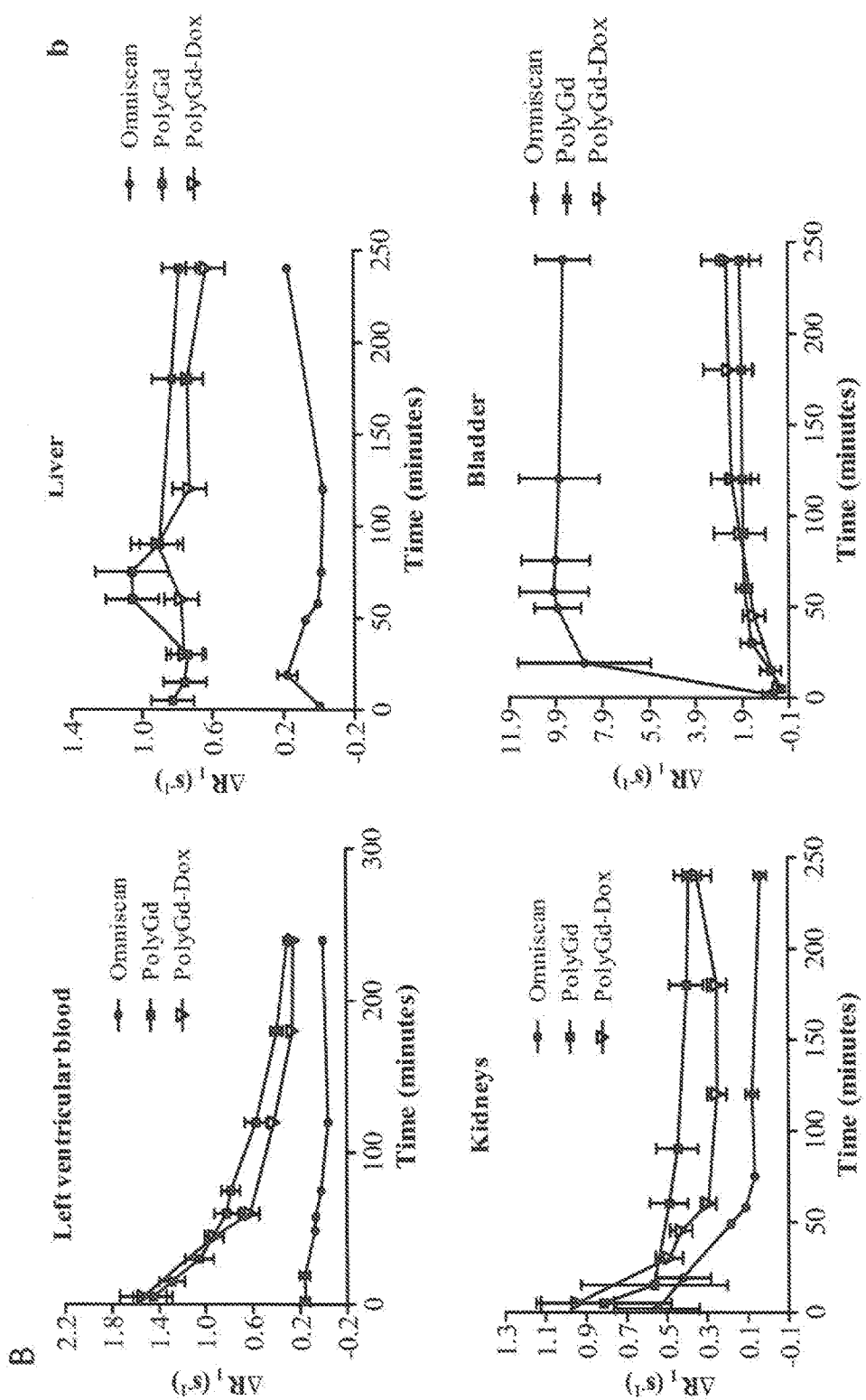
Figure 27:
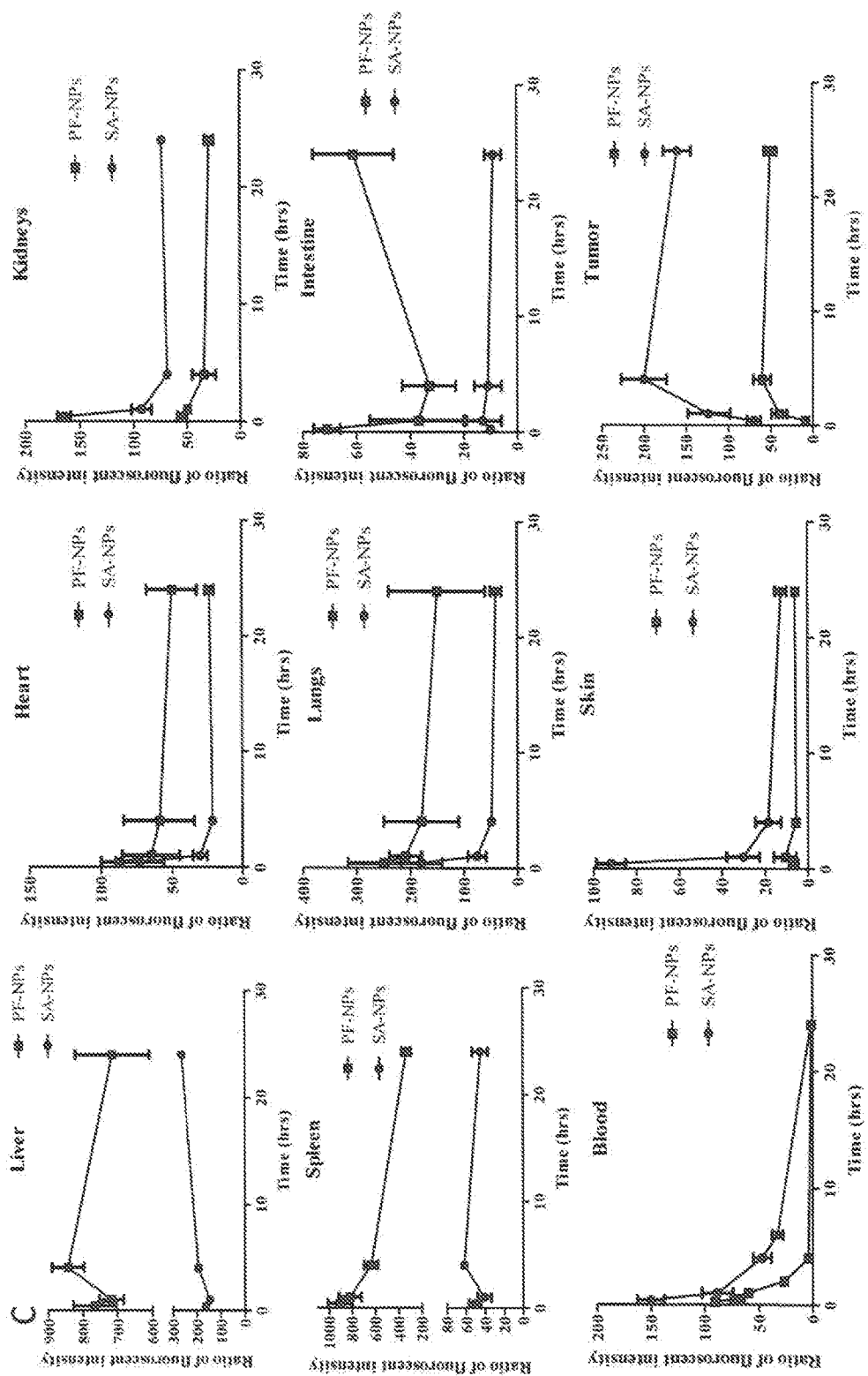

FIG. 27 shows quantitative MRI of whole-body distribution: (A) $R_1$ maps of Balb/c mice injected with $Gd^{3+}$ loaded PMAA-g-St polymer (0.025 mmol/kg $Gd^{+3}$). (B) Change in relaxation rates, $\Delta R_1$, of left ventricular blood, liver, bladder, and kidneys for Omniscan® (0.1 mmol/Kg $Gd^{3+}$), PolyGd (0.025 mmol/Kg $Gd^3$), and PolyGd-Dox (0.025 mmol/Kg $Gd^{3+}$) over time relative to baseline. PolyGd and PolyGd-Dox cause a much higher increase in blood relaxation rate for an extended period of time compared to Omniscan®. The data are presented as mean±standard deviation of three independent runs. (C) Quantitative results of tissue distribution and tumor accumulation for SA-NPs and PF-NPs. Ratio of the relative fluorescence intensity in major organs, tumor, and blood as a function of time after intravenous injection of nanoparticles, compared to normal major organs and tumors not injected with NIR dye conjugated-nanoparticles. Data are presented as means±standard deviation (n=2×3).

Figure 28:
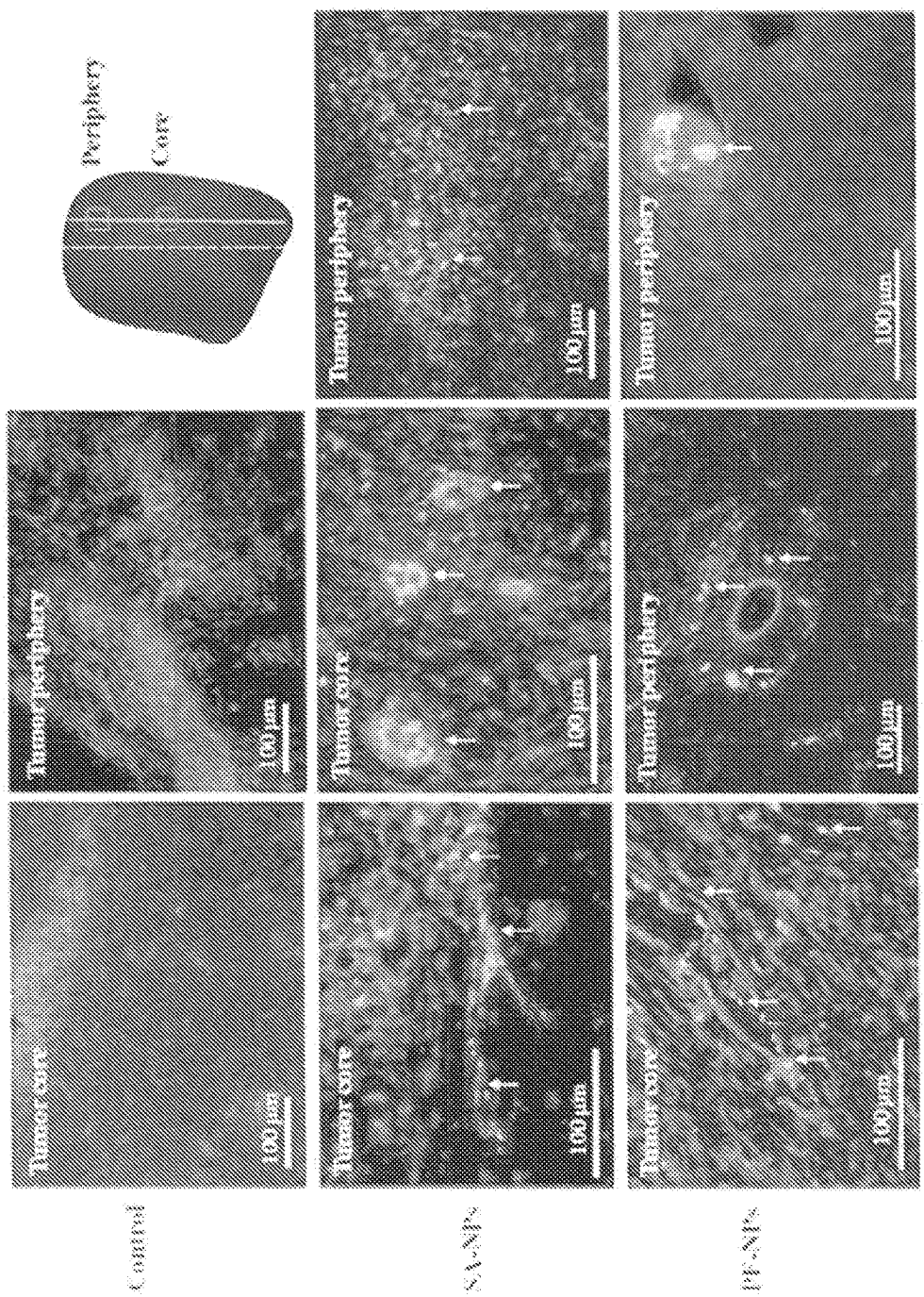

FIG. 28 shows quantitative results of tissue distribution and tumor accumulation for SA-NPs and PF-NPs. Ratio of the relative fluorescence intensity in major organs, tumor, and blood as a function of time after intravenous injection of nanoparticles, compared to normal major organs and tumors not injected with NIR dye conjugated-nanoparticles. Data are presented as means±standard deviation (n=2×3).

Figure 29:
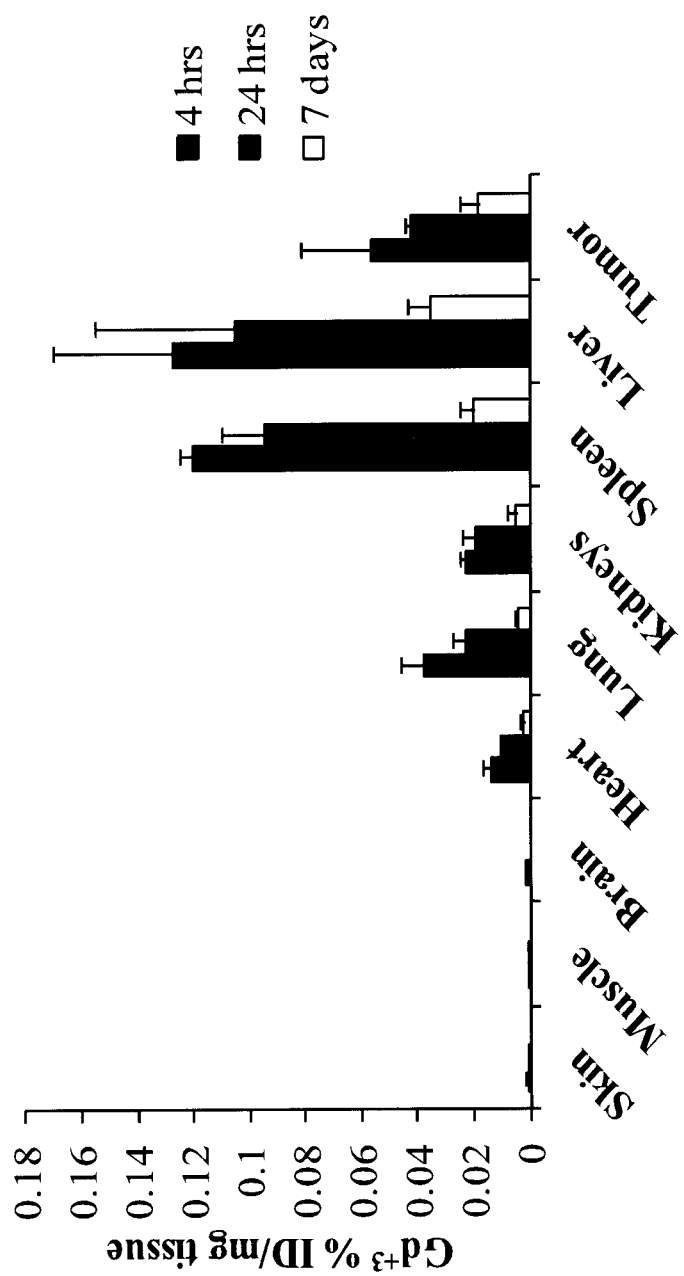

FIG. 29 shows biodistribution, elimination and tumor accumulation of the PolyGd (0.025 mmol/kg $Gd^{3+}$) in tumor-bearing Balb/c mice. The $Gd^{3+}$ content was determined using ICP-AES. The data are presented as means±standard deviations of three independent runs.

Figure 30:
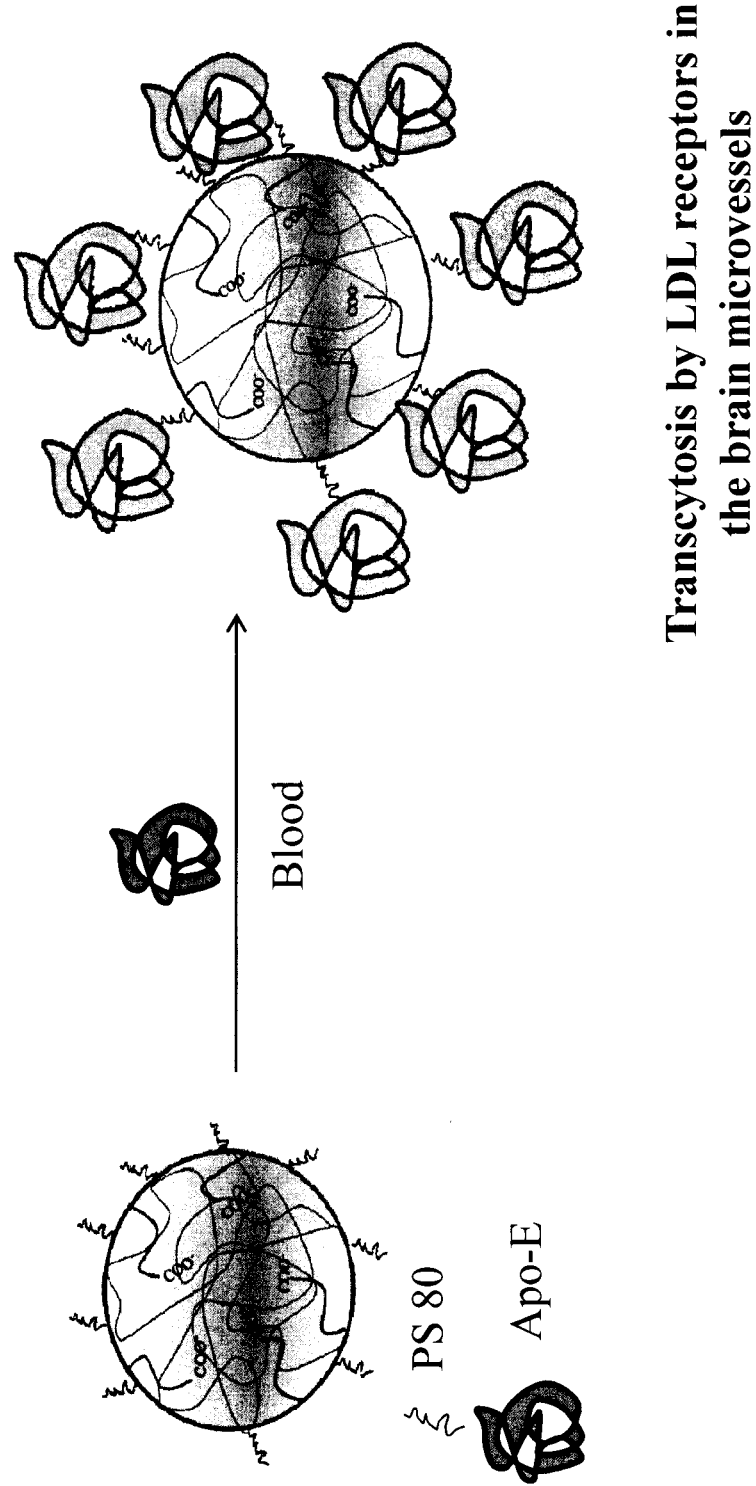

FIG. 30 is a schematic of polysorbate 80 (PS80) incorporated into a nanoparticle. PS80 is capable of binding to Apo-E which in turn binds to LDL receptors in brain microvessels, enabling transcytosis of the nanoparticle. NMR data indicate PS80 polymerization into the St-g-PMAA nanoparticles and linear polymers. Covalently bound PS80 ensures stability in vivo.

Figure 31:
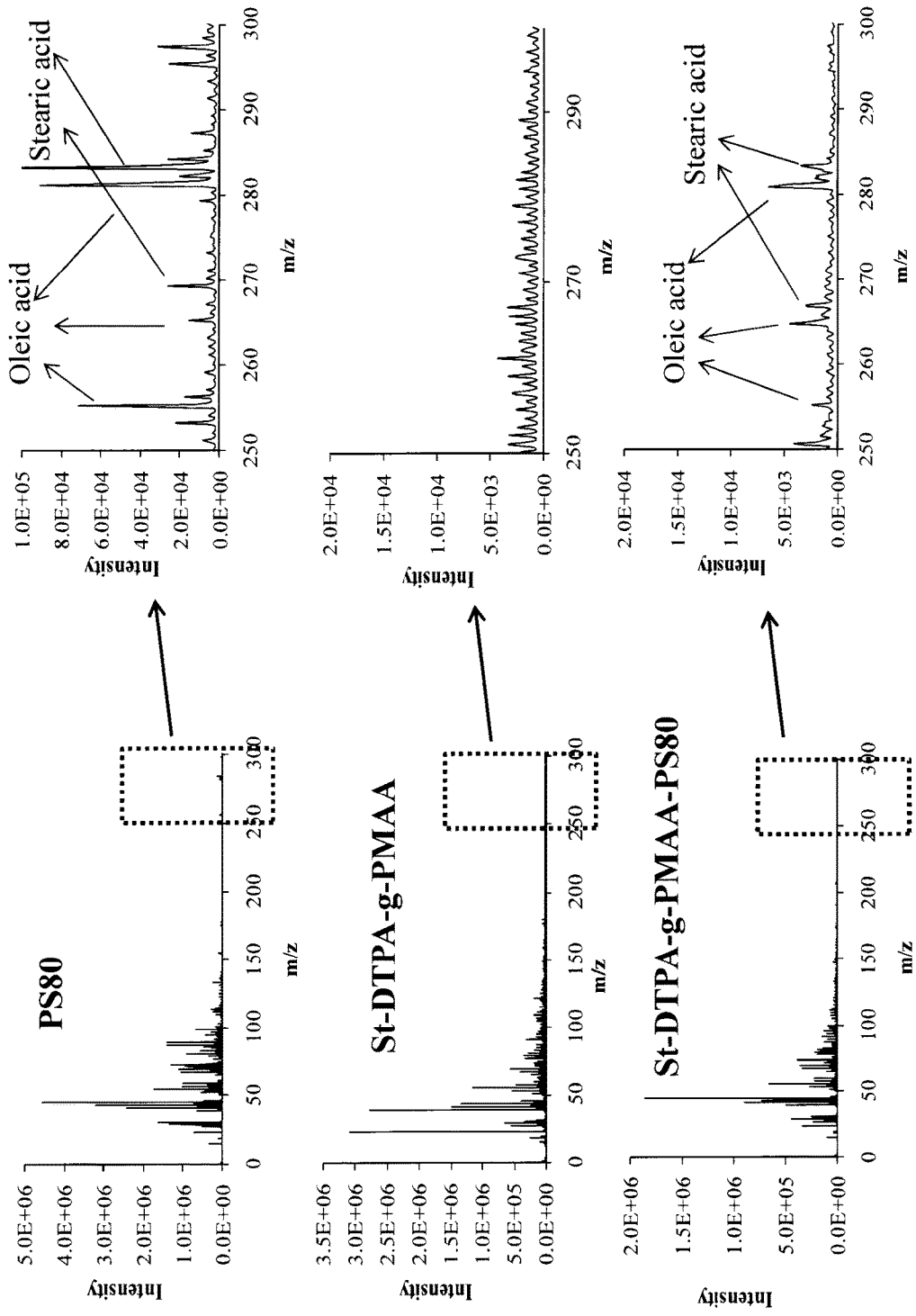

FIG. 31 shows TOF-SIMS data indicating polysorbate 80 expression on the particle surface. TOF-SIMS clearly shows the presence of PS80 by the characteristic peaks at 255, 265, 267, 281 and 283 in the positive ion mode representing the series of oleic, and stearic fatty acids that are side chains of the sorbitan molecule.

Figure 32:
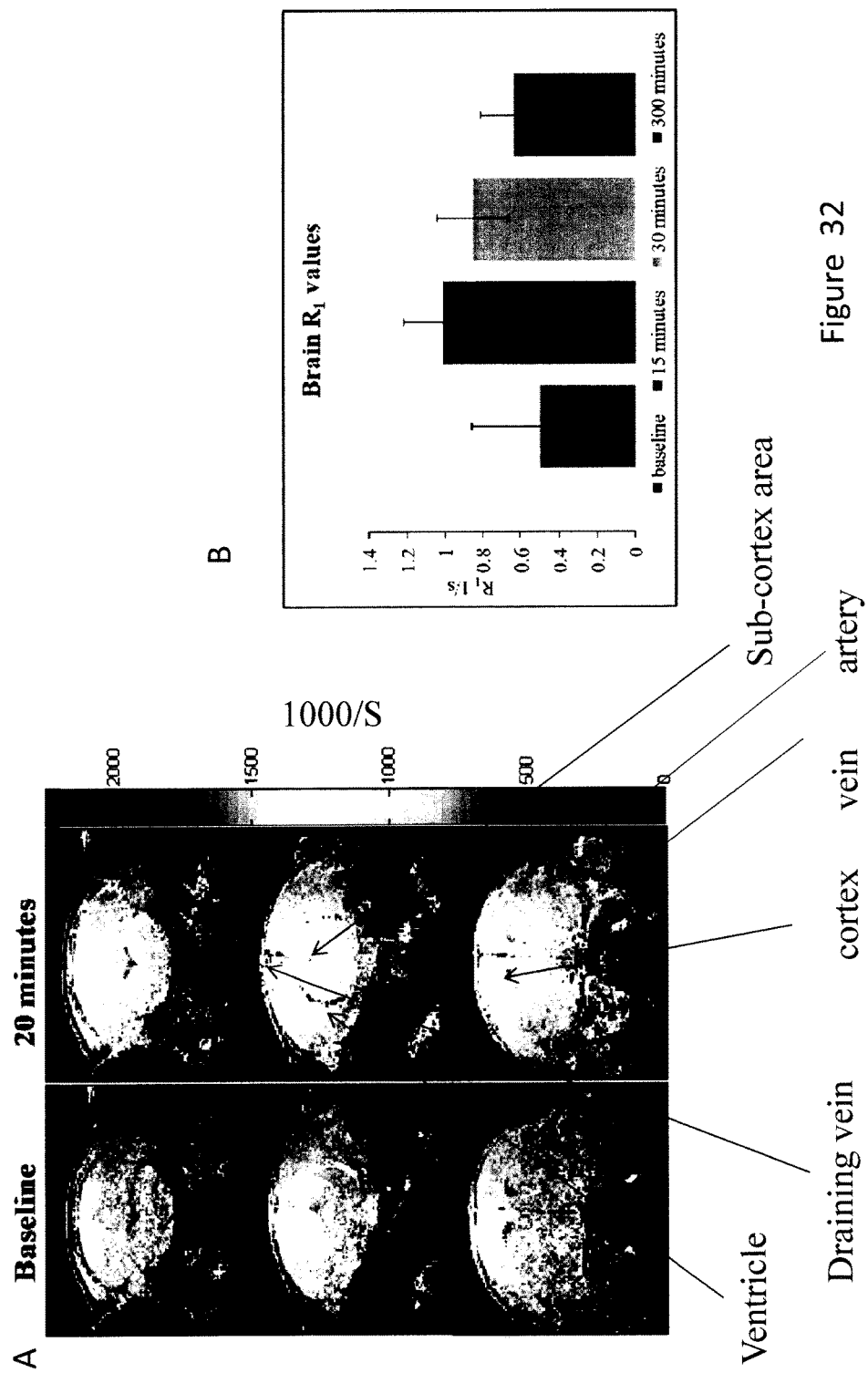
Figure 32:
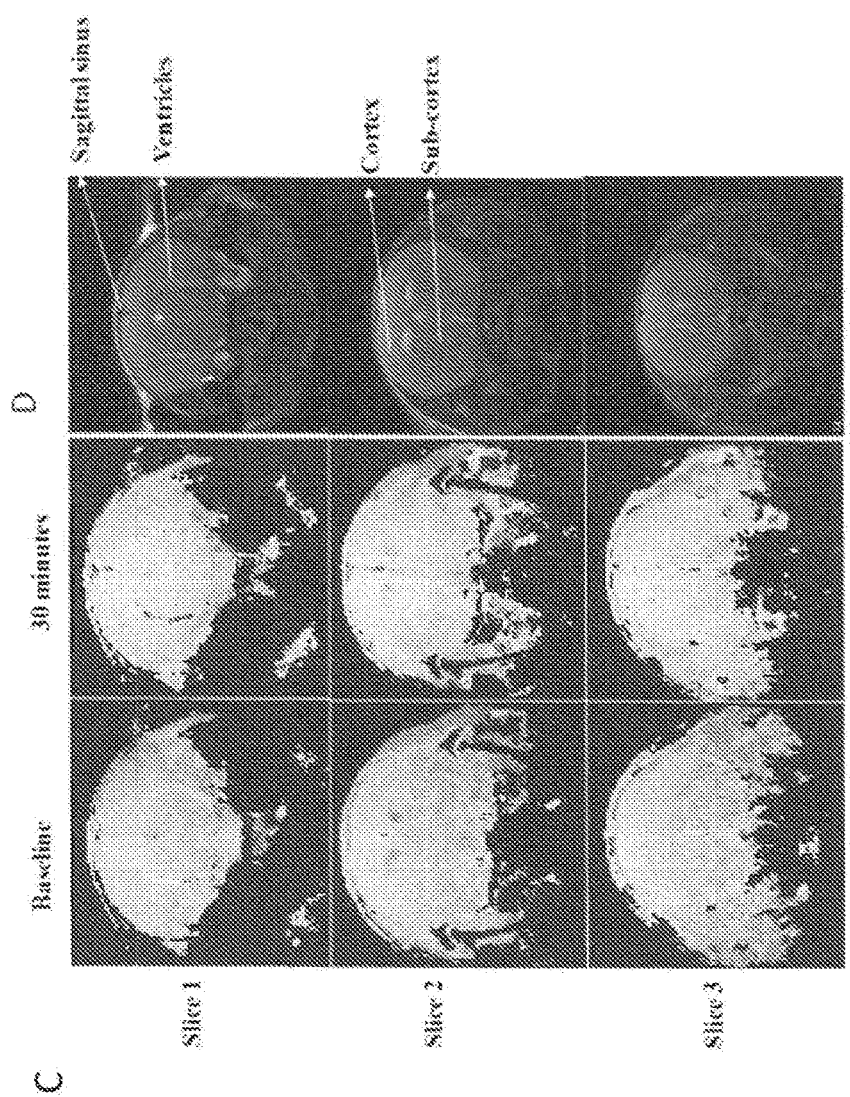
Figure 32:
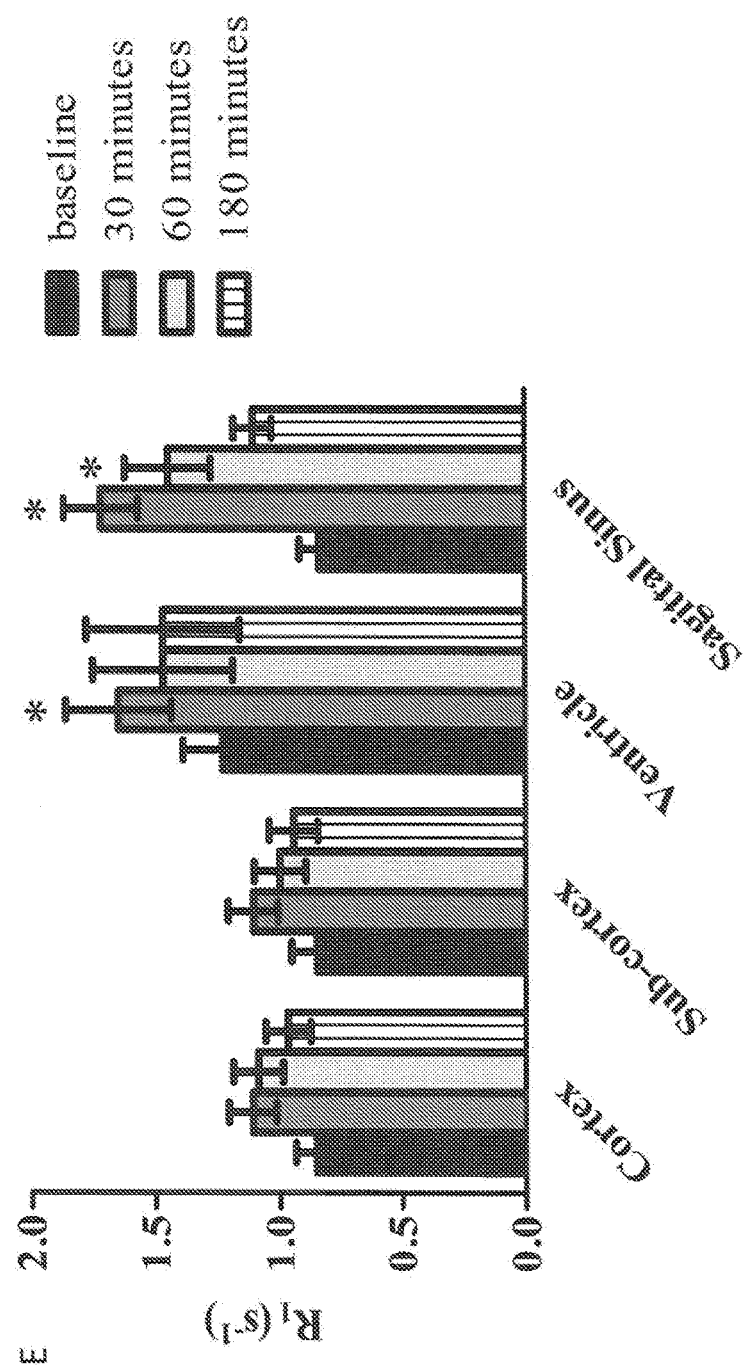

FIG. 32 shows MR imaging of the mouse brain following administration of Gd3+-loaded nanoparticles. (A) $R_1$ maps of the mice coronal brain slices at baseline and 20 minutes after administration of PMAA-g-St-P80. (B) Brain $R_1$ values at various time points. (C) Quantitative MRI of brain distribution: $R_1$ maps of Balb/c mice (n=3) injected with $Gd^{3+}$ loaded PMAA-PS 80-g-St nanoparticles (0.05 mmol/kg $Gd^{+3}$). (D) Longitudinal relaxation rates ($R_1$) of sagittal sinus, ventricles, cortex, and sub-cortex for $Gd^{3+}$ loaded PMAA-PS 80-g-St-DTPA polymer overtime. The asterisk (*) denotes a significant difference (p<0.05) in $R_1$ values compared to baseline. (E) Brain $R_1$ values at various time points.

Figure 33:
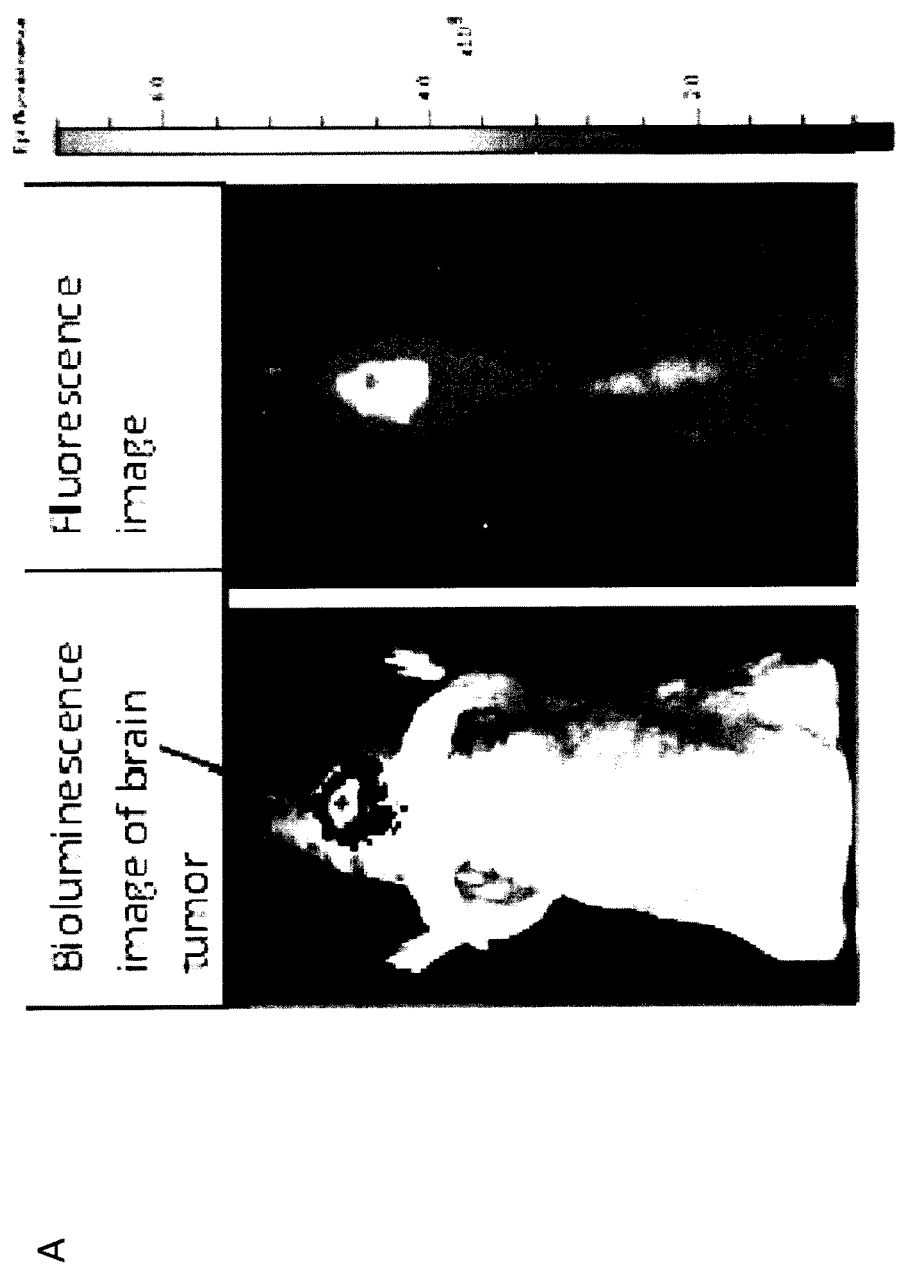
Figure 33:
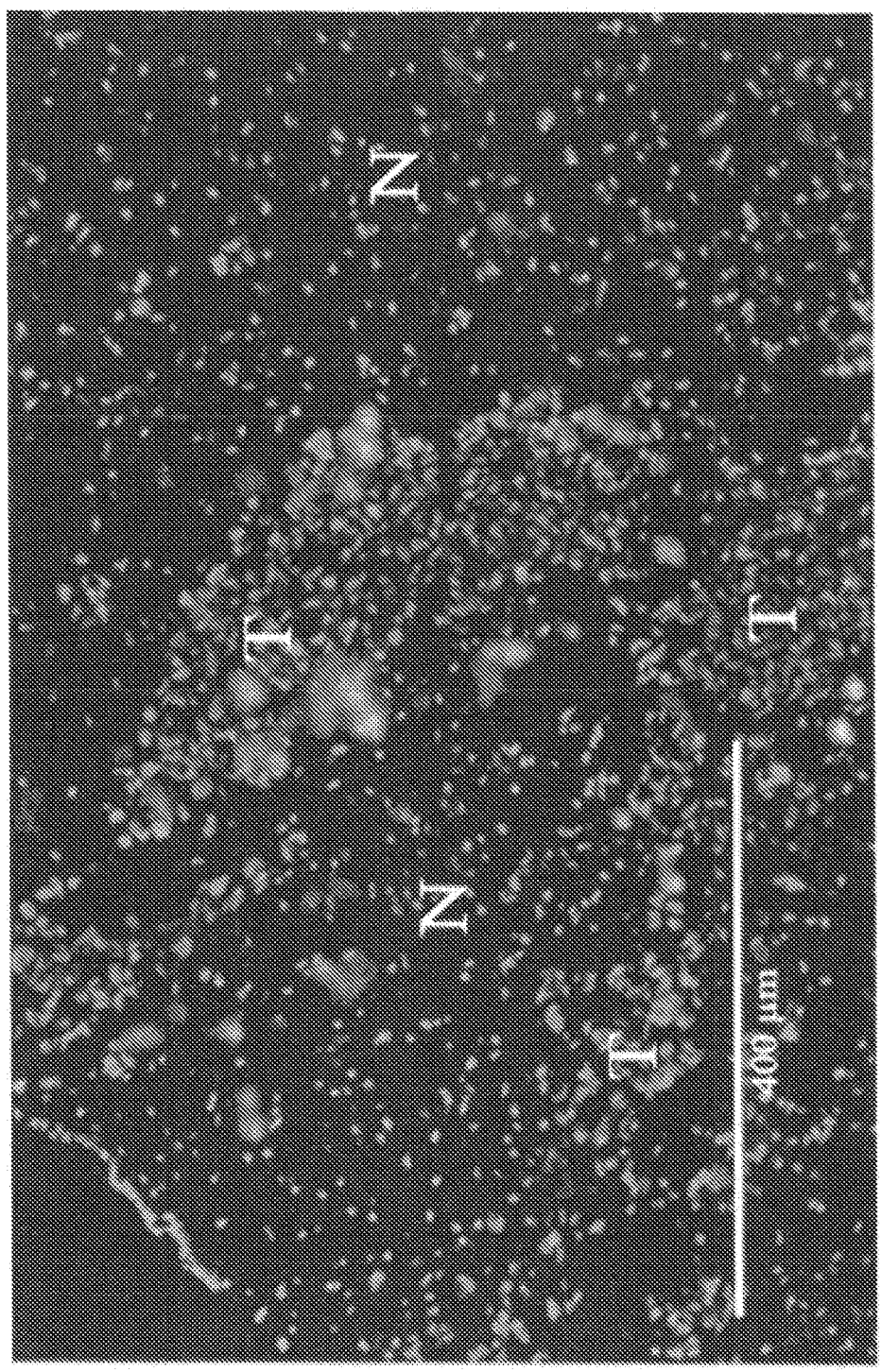

FIG. 33 shows (A) Representative images of brain tumor acquired by bioluminescence imaging (left) and distribution of PMAA-PS 80-g-St nanoparticles labeled with a near infrared dye (Hilyte Fluor 750, fluoresceinamine isomer I) (right). The results strongly suggest the accumulation of the nanoparticles in the brain tumor. The brain metastasis of MDA-MB-231-luc-D3H2LN was established by intracranial injection of the cells. After a week, the brain tumor was imaged 3-5 min following i.p. injection of luciferin solution. The fluorescence image was acquired 6 hours after tail vein injection of the nanoparticles. (B) Fluorescence microscopic image of a brain tumor section acquired using a DAPI and RFP filter set to visualize the Hoescht 33342-stained cell nuclei (blue) and NIR HF 750-labeled nanoparticles. The image shows clearly the nanoparticles (red) and Dox (green) are colocalized suggesting the Dox delivered by the nanoparticle to the tumor tissue and released from the nanoparticles in the brain tumor.

Figure 34:
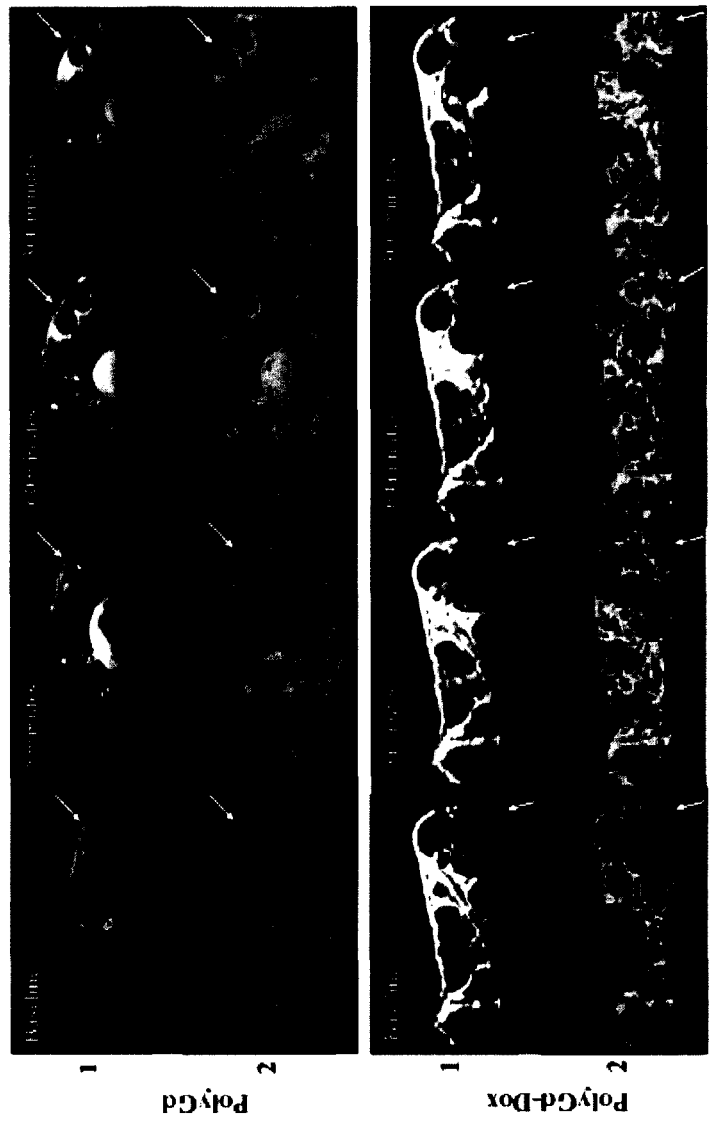
Figure 34:
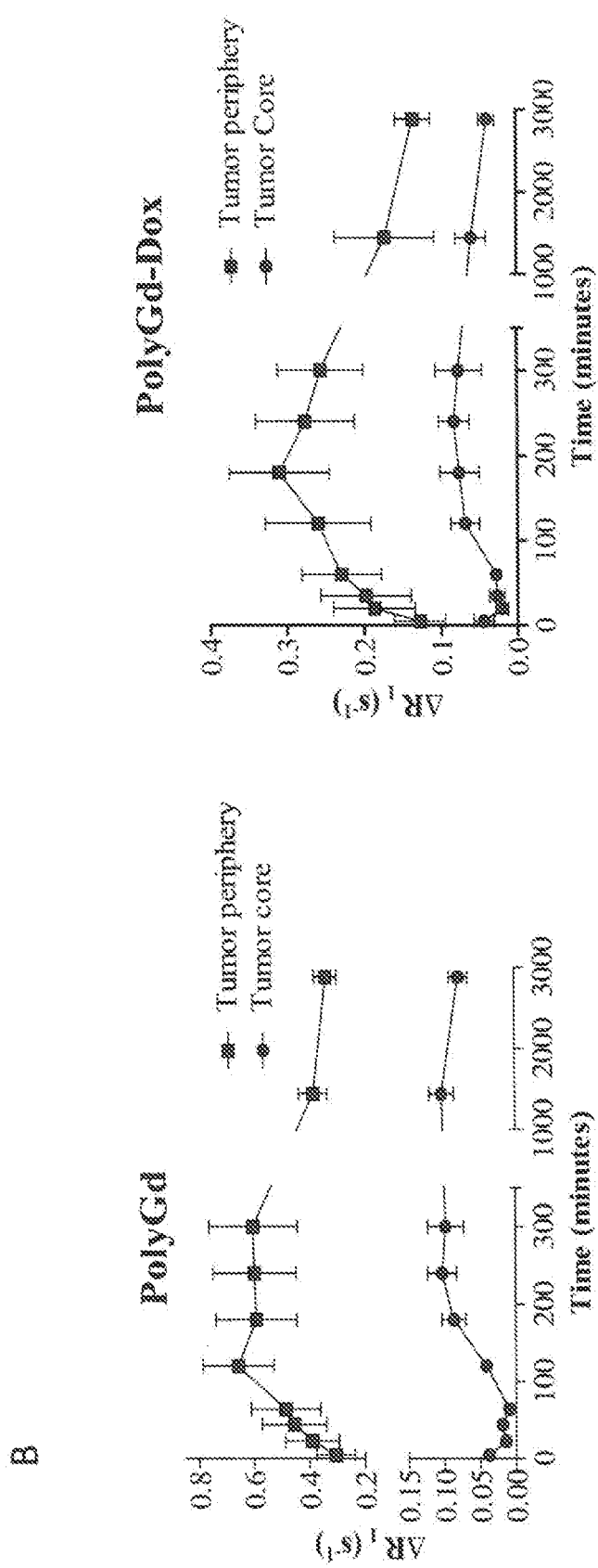

FIG. 34 shows Gd(III)-loaded linear polymers achieve significant MR contrast in a mouse tumor model. (A) Tumor distribution of PolyGd (upper) and PolyGd-Dox (lower) (0.025 mmol/kg $Gd^{3+}$): $T_1$-weighted images (1) and the corresponding $R_1$ maps (2). The arrows indicate the tumor implanted subcutaneously in the right rear flank. (B) Time course of $\Delta R_1$ in tumor periphery and tumor core, displaying elevated tumor $R_1$ even 48 hours after contrast agent injection. The data are presented as mean±standard deviation of three independent runs.

Figure 35:
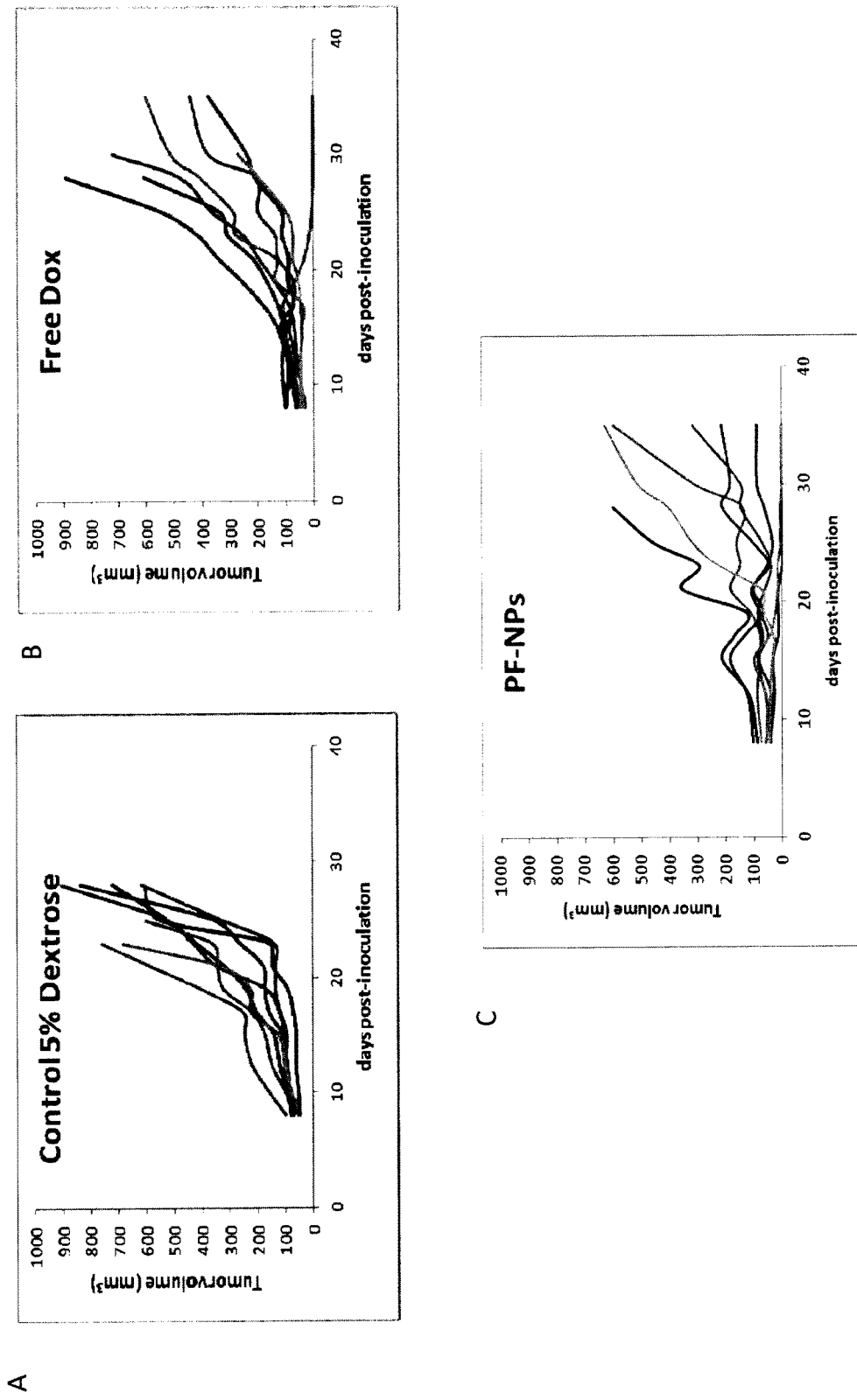
Figure 35:
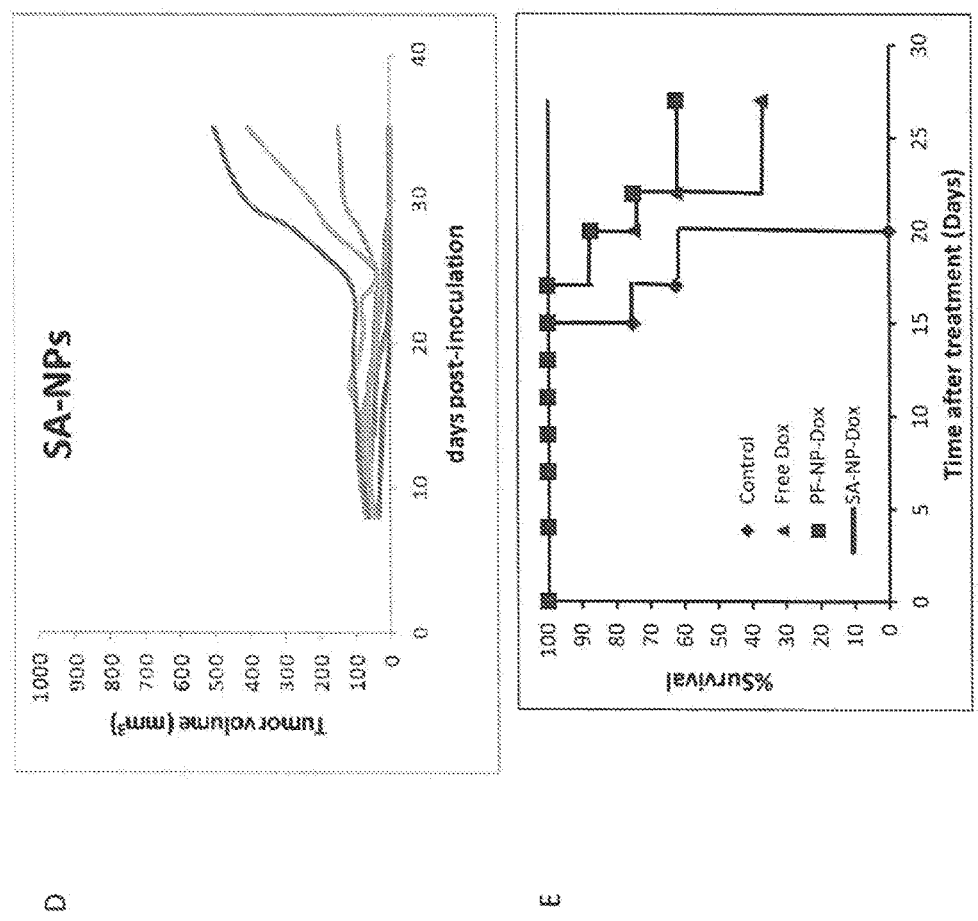
Figure 35:
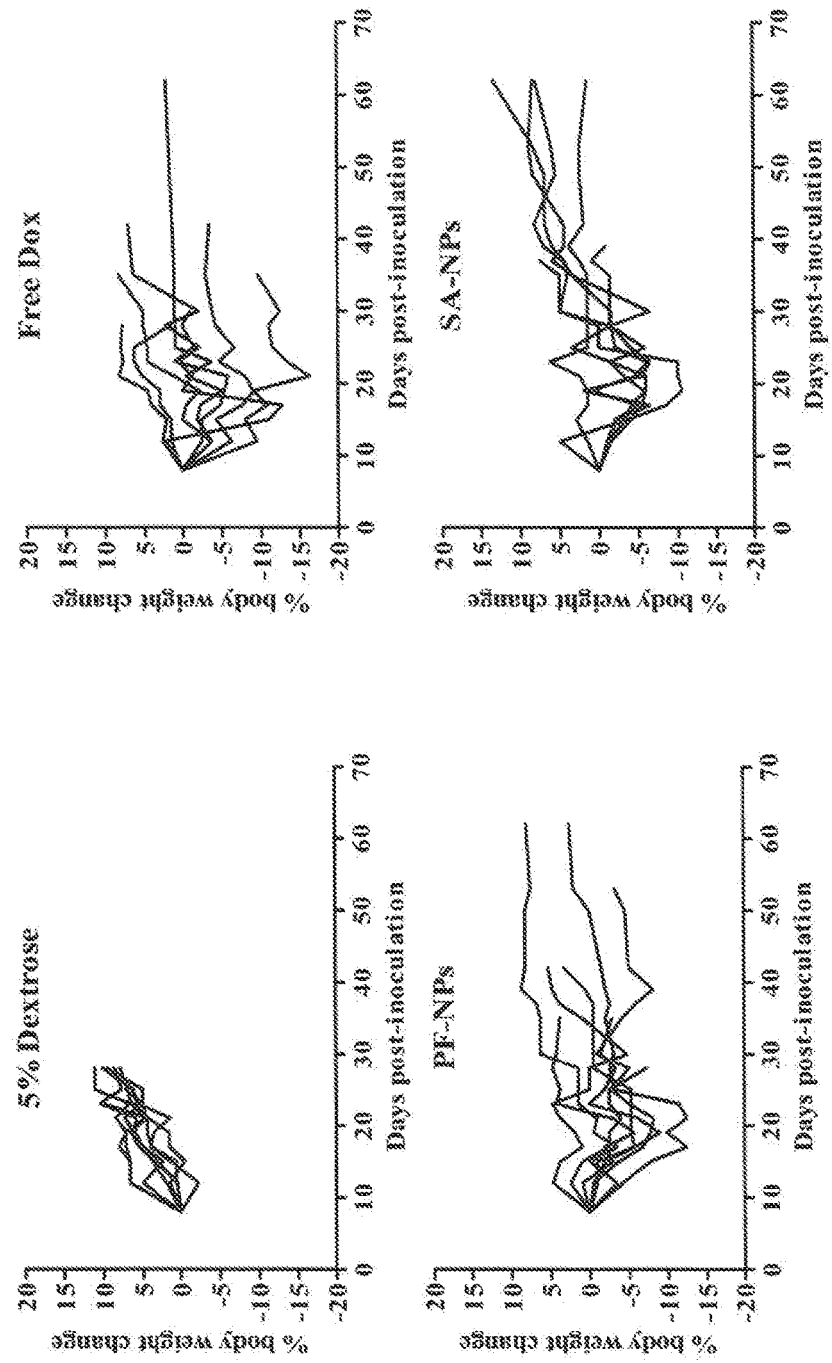
Figure 35:
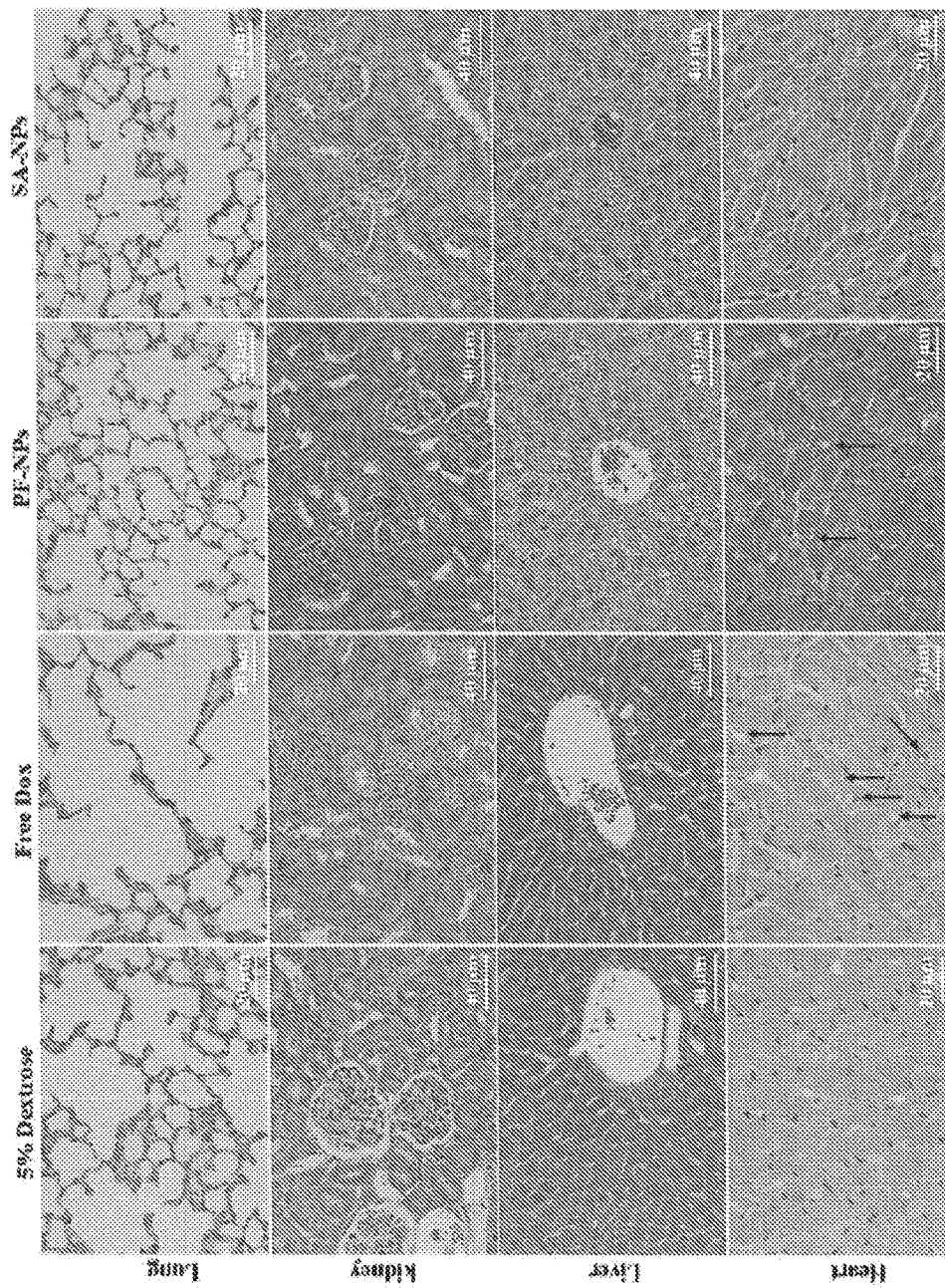

FIG. 35 shows anti-tumor activity of starch-based nanoparticles in EMT6/WT tumor bearing mice. Tumor cells were implanted orthotopically on day zero. Mice were treated with (A) 5% dextrose (n=2×4), (B) free Dox (n=8), PF-NPs (n=2×4), (C) PF-NPs, and (D) SA-NPs (n=2×3) at a dose of 2×10 mg/kg equivalent to Dox on day 8 and 15. Tumor volume up to day 62. Each curve represents one animal. (E) Kaplan Meier survival curves for 5% dextrose, free Dox, PF-NPs, and SA-NPs. The trend in survival curves were significantly different (p=0.0033, Mantel Cox). The mice were treated by intravenous injection of various formulations at day 8 and day 15. (F) Time profiles of body weight of tumor-bearing mice treated with 5% dextrose (n=2×4), free Dox (n=2×4), PF-NPs (n=2×4), and SA-NPs (n=2×3) at a dose of 2×10 mg/kg equivalent to Dox. Balb/c mice were inoculated with EMT6/WT tumor in the mammary fat pad and received treatment on day 8 and 15 post inoculation. Each curve represents one animal. (G) Time profiles of body weight of tumor-bearing mice treated with 5% dextrose (n=2×4), free Dox (n=2×4), PF-NPs (n=2×4), and SA-NPs (n=2×3) at a dose of 2×10 mg/kg equivalent to Dox. Balb/c mice were inoculated with EMT6/WT tumor in the mammary fat pad and received treatment on day 8 and 15 post inoculation. Each curve represents one animal.

Figure 36:
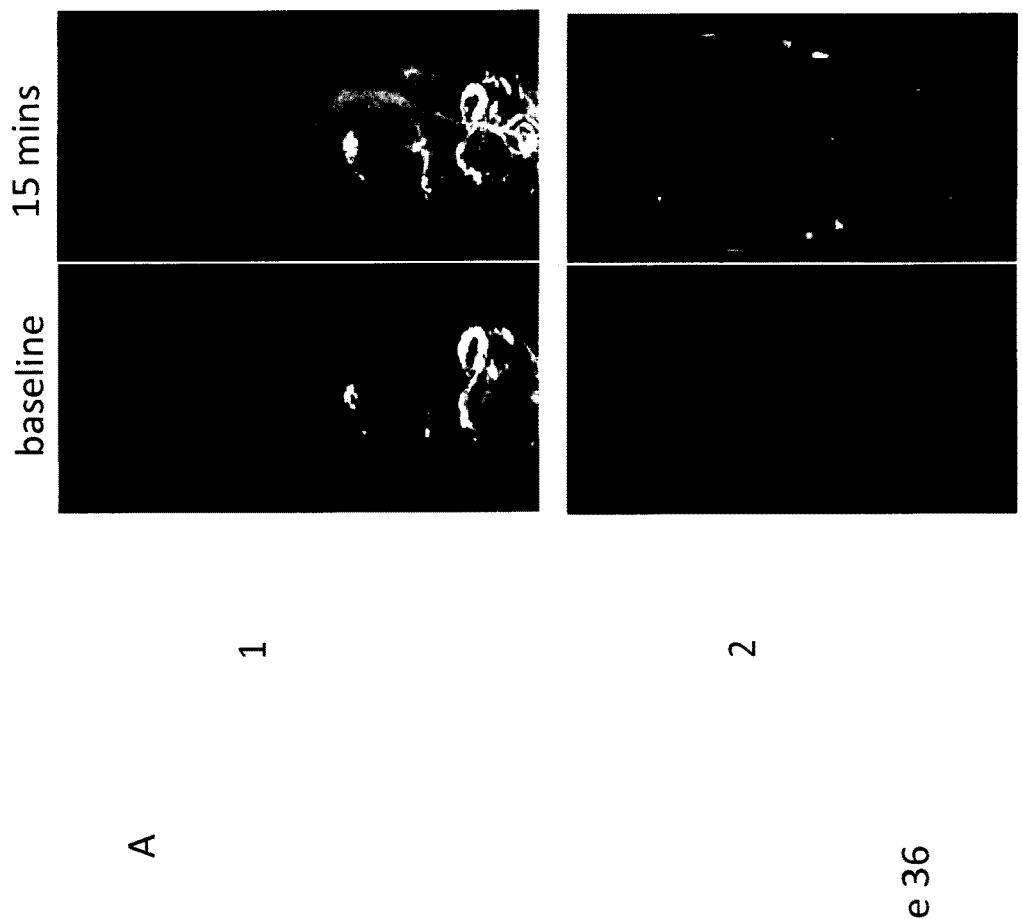
Figure 36:
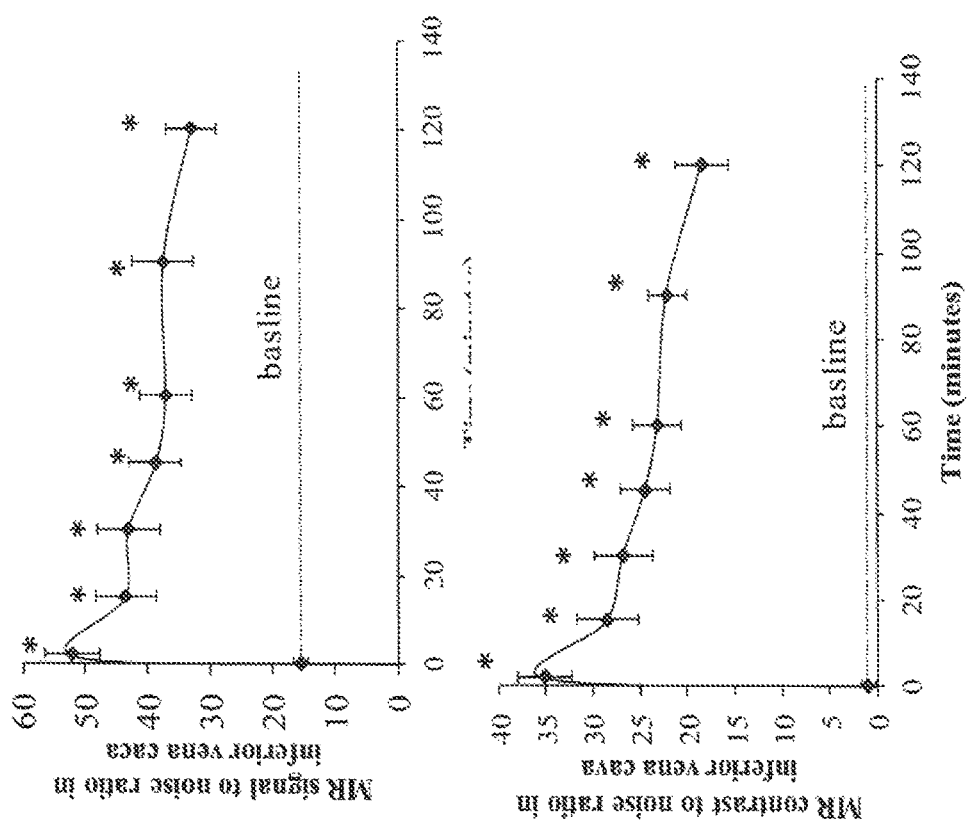

FIG. 36 shows (A) MIP angiogram displaying contrast enhancement of (1) whole body and (2) neck and head regions, obtained prior to (baseline) and at 15 minutes following $Gd^{3+}$ loaded PMAA-g-St-DTPA injection at 0.03 mmol Gd/kg. (B) Kinetics of vascular signal to noise (S/N) ratio and contrast to-noise (C/N) ratio measured from the inferior vena cava in whole-body angiograms. * denotes a significant difference compared to baseline (p<0.05). The data are presented as mean and standard deviation of three independent runs.

Figure 37:
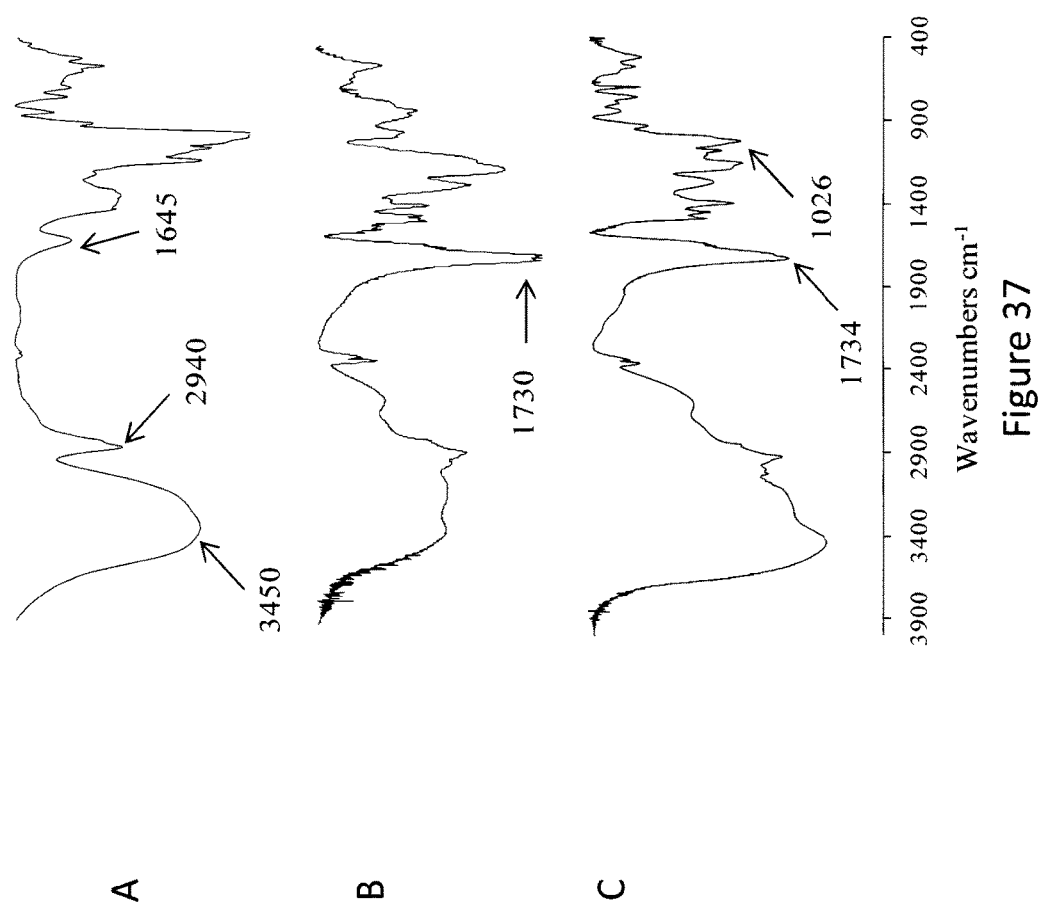

FIG. 37 shows FTIR spectra of (A) pure starch, (B) PDEAEM, and (C) PDEAEM-g-St.

Figure 38:
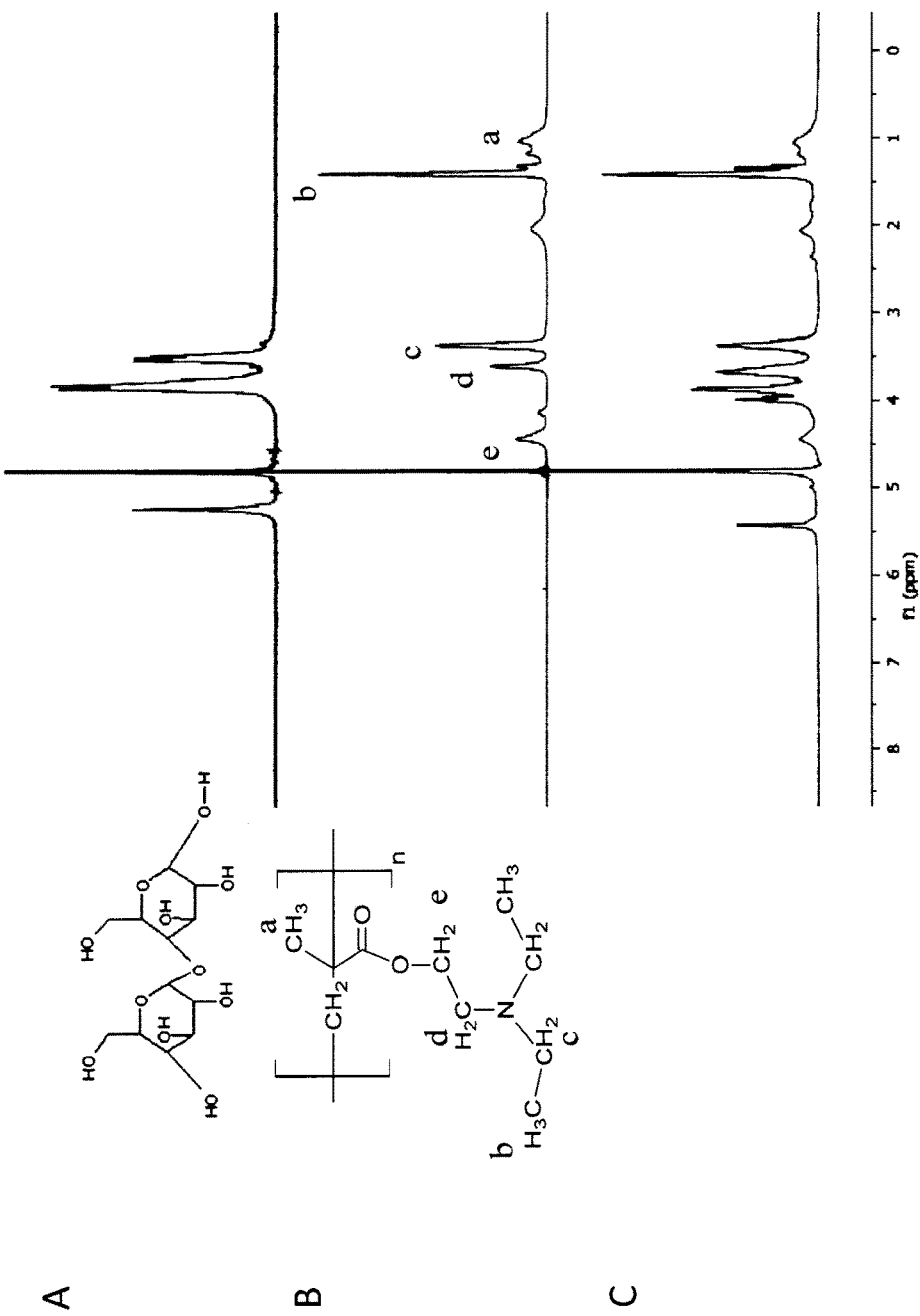

FIG. 38 shows H NMR spectra of (A) starch, (B) PDEAEM, and (C) PDEAEM-g-St.

Figure 39:
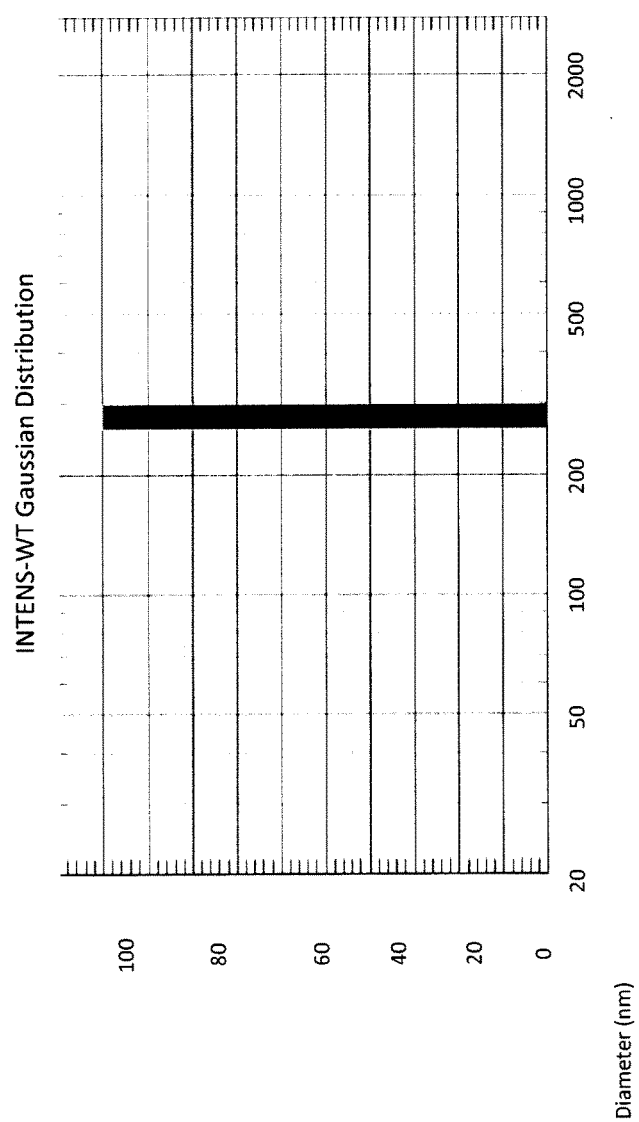

FIG. 39 shows intensity-weight distribution of PDEAEM-g-St-1 nanoparticles in 0.15M PBS pH=4.

Figure 40:
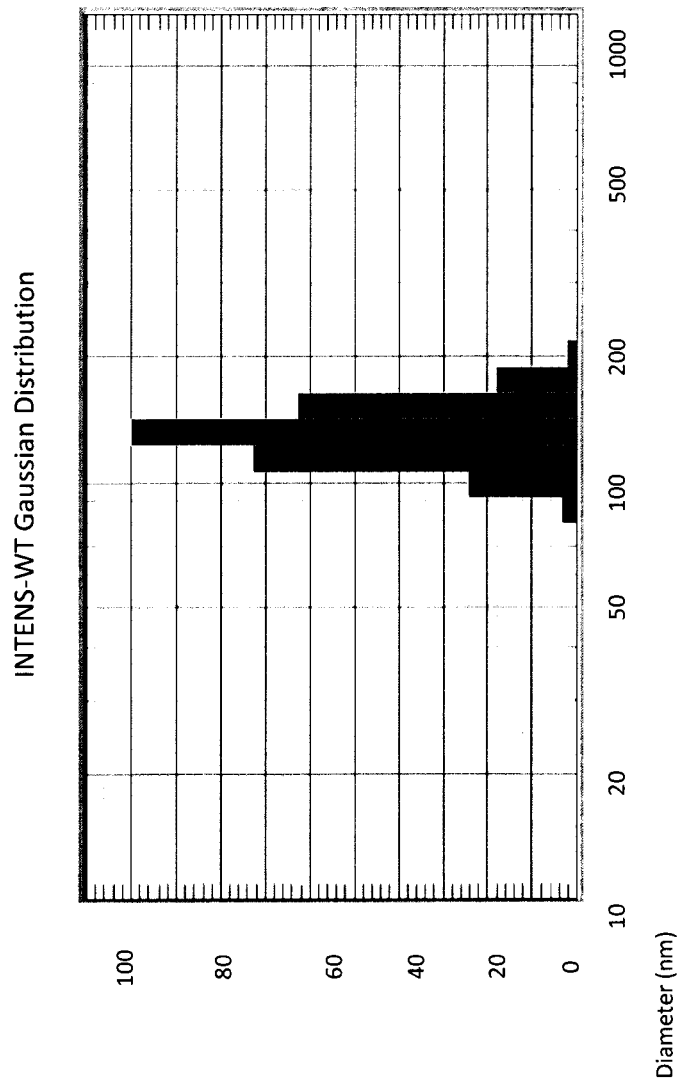

FIG. 40 shows intensity-weight distribution of PDEAEM-g-St-1 in 0.15 M PBS pH=7.4.

Figure 41:
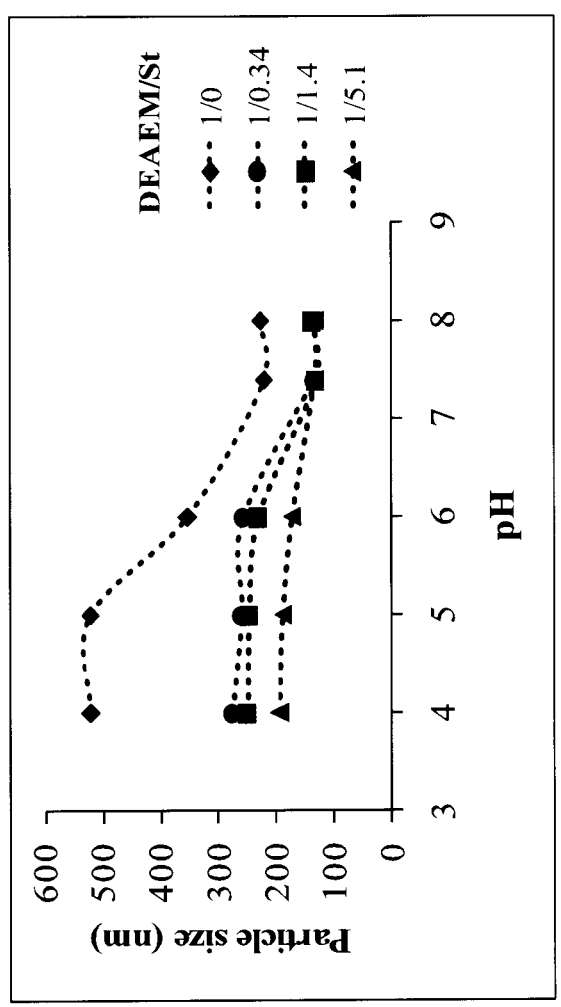

FIG. 41 shows diameter of the PDEAEM-g-St particles of various starch composition at 25° C. as a function of pH of the medium.

Figure 42:
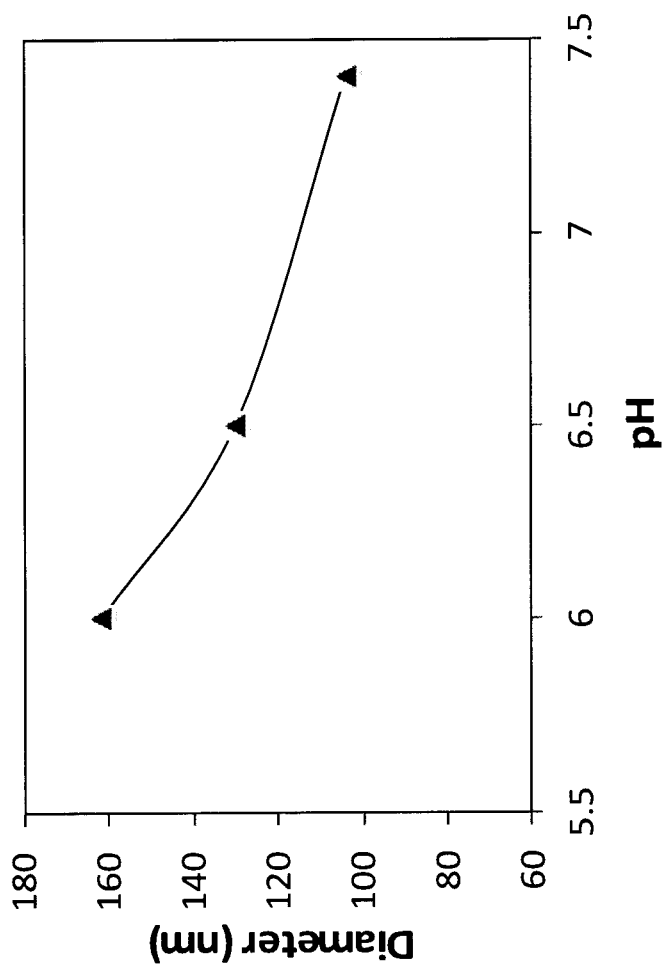

FIG. 42 shows diameter of Gd-conjugated PDEAEM-g-St-DTPA nanoparticles at different pH.

Figure 43:
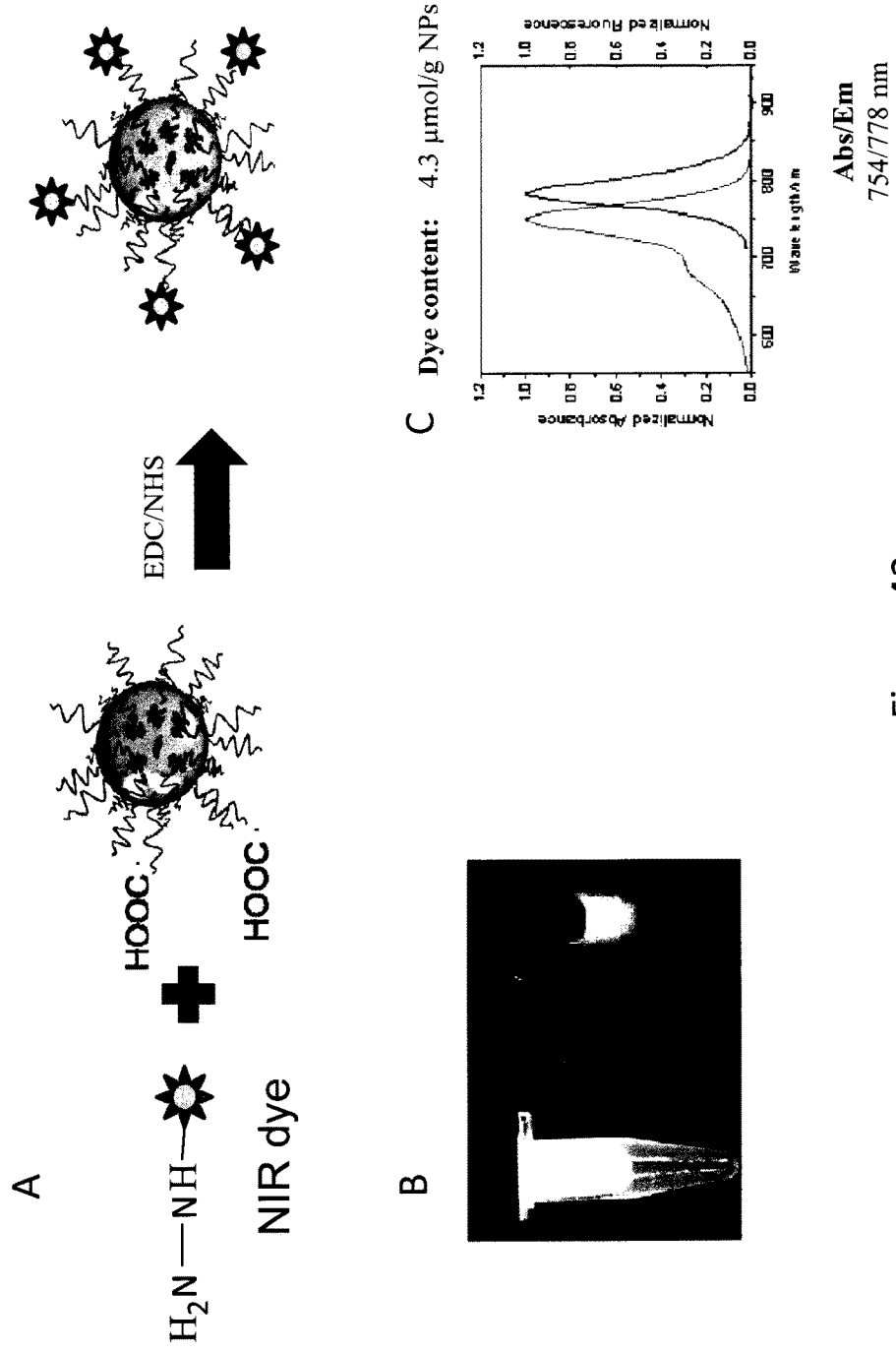

FIG. 43 shows near infrared dye conjugation in the nanoparticles. A) A schematic of the conjugation reaction. (B) The PMAA-g-St-PS80 labelled with a NIR dye compared to blank. C) Nanoparticles show fluorescence emission at 820 nm with dye content of 4.3 μmol/g.

Figure 44:
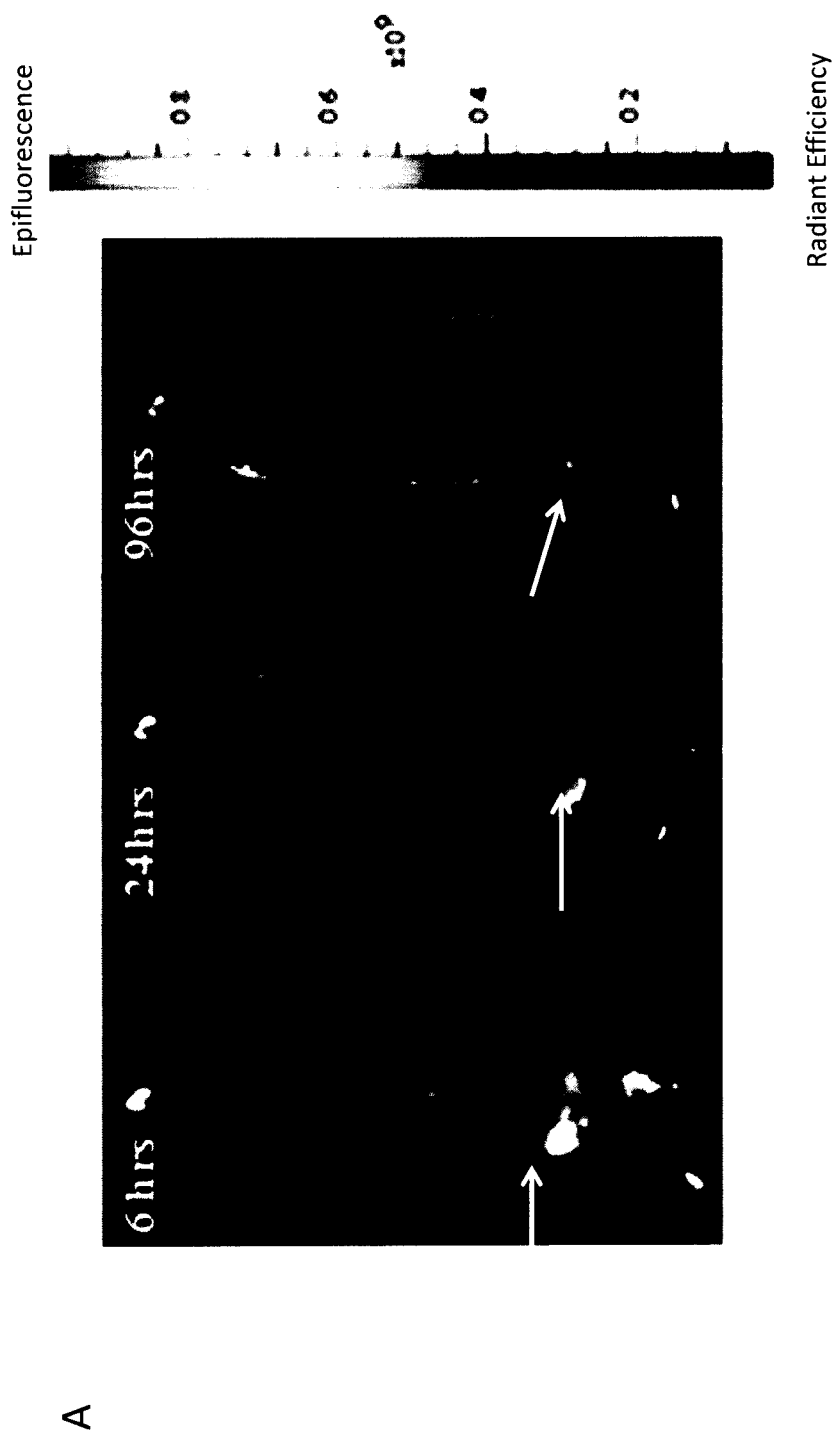

FIG. 44 shows (A) tumor accumulation of the PMAA-g-St-P80 polymer in murine breast cancer tumor model. The animal was imaged at different time points after tail vein injection of 0.2 ml of PMAA-g-St-PS80 (4.5 mg/ml). The tumor is indicated with arrow.

FIG. 45 shows nanoparticle preparation recipes and polymer composition. Reaction yield was defined as the ratio of purified terpolymer to the total weight of MAA, PS 80, and starch in the feed.

FIG. 46 shows characterization of the drug-loaded nanoparticles. The effect of drug loading on the particle size and surface charge is shown. Particle diameter refers to the number-weighted diameter of readings averaged over 5 minutes. Loading efficiency is the fraction of originally added drug that was incorporated into the NPs, whereas drug loading content is the percent of drug weight to total weight of the nanoparticles. All values are reported as the mean±standard deviation of three independent trials.

FIG. 47 shows intensity-weighted hydrodynamic diameter of nanoparticles with different feed molar ratio of MAA/St in 0.15 M PBS of various pH. The ionic strength was kept constant using NaCl. All values are described as the mean±standard deviation of three independent trials.

FIG. 48 shows feed and product MAA contents calculated from titration data along with zeta potential values in buffers of pH 4 and pH 7.4 and ionic strength of 10 mM. All values are described as the mean±standard deviation of three independent trials.

FIG. 49A shows $Gd^{+3}$ content and in vitro relaxivity of St-DTPA-g-PMAA-P80; the relaxivity was measured in 0.9% NaCl at 3T and 7T. Omniscan has been included for comparison.

FIG. 49B shows $Gd^{3+}$ content, Dox content, molecular weight, particle size, and $r_1$ for Omniscan®, PolyGd, and PolyGd-Dox. The $r_1$ were measured in saline at 3 and 7 T. Means and standard deviations of three independent experiments are shown. Molecular weight of Omniscan® was calculated based on its molecular formula.

FIG. 50 shows $Gd^{3+}$ content, Dox content, molecular weight, particle size, and $r_1$ for Omniscan®, PolyGd, and PolyGd-Dox. The $r_1$ were measured in saline at 3 and 7 T. Means and standard deviations of three independent experiments are shown. Molecular weight of Omniscan® was calculated based on its molecular formula.

FIG. 51 shows feed composition of various PDEAEM-g-St batches.

EXAMPLES

Chemical and Reagents

Soluble starch (MW 2,600-4,500 Da), methacrylic acid (MAA), N,N'-Methylenebisacrylamide (MBA) sodium thiosulfate (STS), potassium persulfate (KPS), polysorbate 80 (PS 80), and sodium dodecyl sulfate (SDS) were purchased from Sigma-Aldrich Canada (Oakville, ON, Canada). MAA inhibitor was removed by vacuum distillation prior to use. All other chemicals were reagent grade and were used as received.

Cell Line and Maintenance

The murine breast carcinoma cell line EMT6/WT was initially provided by Dr. Ian Tannock (Ontario Cancer Institute, Toronto, ON, Canada) and now maintained in our laboratory. Monolayers of cells were cultured on 75 cm² polystyrene tissue culture flasks at 37° C. in 5% CO2/95% air humidified incubator. Cancer cells were maintained in α-minimal essential medium (Ontario Cancer Institute Media Laboratory, Toronto, ON, Canada), supplemented with 10% fetal bovine serum (Cansera Inc., Etobicoke, ON, Canada). Cells grown to confluence were trypsinized with 0.05% trypsin-EDTA (Invitrogen Inc., Burlington, ON, Canada), diluted (1/10) in a fresh growth medium and reseeded.

Experimental Animals and Induction of Orthotopic Breast Tumors

All animal work was approved by the animal care committee at the University Health Network, and all experiments were performed in accordance with all guidelines and regulations put forth by the Canadian Council on Animal Care. 8 week old female Balb/c mice (Jackson laboratory, Maine, USA) were used. The animals were allowed free access to food and water throughout the study. For tumor studies, 1 million murine EMT6 breast cancer cells were injected subcutaneously into the left flank. Tumors were monitored for growth and MRI studies were initiated at tumor average diameter of 5 mm.

Preparation and Characterization of Nanoparticles

Example 1. Synthesis of Polymethacrylic Acid-Grafted-Starch (PMAA-g-St) Nanoparticles Synthesis of PMAA-PS-80-g-St Nanoparticles A free radical dispersion polymerization method was used to prepare PMAA-g-St nanoparticles in one-pot using potassium persulfate/sodium thiosulfate initiation (KPS/STS) system. A series of preliminary studies were performed to identify suitable surfactants type and concentration as well as monomer concentration required to obtain stable particles.

The polymerization was conducted in a 500 ml three-necked flask fitted with nitrogen inlet, condenser, thermometer, and magnetic stirrer which was immersed in a water bath. The desired amount of starch was dissolved in distilled water by heating at 95° C. for 30 minutes, cooled down to 70° C., and purged with $N_2$ for 30 minutes to remove any dissolved oxygen. Subsequently, desired amounts of SDS, PS 80, KPS and STS were added to the starch solution while under stirring. After 15 minutes, the reaction was started by adding required amounts of nitrogen purged MAA and MBA to the solution. Opalescence appeared after 5 minutes and the reaction was continued for 8 hours at 70° C. to ensure complete conversion. The product was washed extensively with warm water twice and extracted with methanol followed by ultracentrifugation to remove any unreacted materials and homopolymers. The purified particles were freeze dried and stored in a desiccator for future use.

The grafting yield percent (GY %) was calculated using equation 1:

$$GY\ \% = \frac{W_1}{W_T} \times 100\% \quad (1)$$

where $W_1$ is the weight of purified product and $W_T$ is total weight of monomers in the feed.

In another example, the polymerization was conducted in a 500 ml three-necked flask which was immersed in a water bath and equipped with nitrogen inlet, a condenser, a thermometer, and a magnetic stirrer. First, a desired amount of starch (FIG. 1) was dissolved in 170 ml of distilled deionized water (DDIW) which was heated at 95° C. for 30 minutes. The solution was cooled down to 70° C., and purged with $N_2$ for 30 minutes to remove any dissolved oxygen. Next, 0.45 mmol of KPS and 1.36 mmol of STS dissolved in 5 ml of DDIW were added. After 10 minutes, desired amounts of SDS and PS 80 (FIG. 1) dissolved in 10 ml of DDIW were added to the reaction mixture with stirring. After 15 minutes, the reaction was started by adding known amounts of MAA and MBA (FIG. 45) in 10 ml of water purged by nitrogen, and the final solution volume was adjusted to 200 ml by adding DDIW (FIG. 45). Opalescence appeared after 5 minutes and the reaction was continued for 8 hours at 70° C. to ensure complete conversion. The product was washed extensively with warm water and methanol followed by ultracentrifugation (96,000 g) to remove any unreacted materials and homo-polymers. The purified particles were freeze-dried and stored in a desiccator for future use.

The reaction yield percent (RY %) was calculated using the following equation:

$$RY\ \% = \frac{W_1}{W_T} \times 100\%$$

where $W_1$ is the weight of purified product and $W_T$ is total weight of MAA, starch, and PS 80 in the feed.

Confirmation of Grafting with Fourier Transform Infrared Spectroscopy (FTIR)

FTIR spectra were recorded on a Perkin Elmer Spectrum 1000 series spectrometer (MA, USA). Spectra were taken with a resolution of 4 cm$^{-1}$ and averaged over 32 scans. Samples were thoroughly ground with exhaustively dried KBr and pellets were prepared by compression under vacuum.

Proton Nuclear Magnetic Resonance Spectroscopy ($^1$H NMR)

$^1$H NMR measurements were obtained using a Varian Mercury 400 MHz (CA, USA). The PMAA-g-St (with no cross-linking) samples were dissolved in 0.01 M NaOD to obtain a solution concentration of 15 mg/ml. The spectra were obtained with a pulse angle of 25°, a delay time of 10 s, and an acquisition time of 2 s. All chemical shifts are reported in parts per million (ppm) with water peak as the reference.

Examination of the Nanoparticles with Transmission Electron Microscopy (TEM)

Transmission electron microscopy (TEM) was used to examine the shapes and morphologies of the nanoparticles. Nanoparticle suspensions in PBS (pH=7.4) were stained with ammonium molybdate and placed on carbon-coated grids. The samples were blotted with filter paper and left to dry. Transmission electron micrographs were acquired on a Hitachi H7000 electron microscope (Hitachi Canada, Ltd., Mississauga, ON, Canada) with accelerating voltage of 100 kV.

Determination of Particle Size by Dynamic Light Scattering

In one example, particle size was measured by dynamic light scattering (DLS), using a NICOMP™ 380ZLS (PSS-NICOMP, Santa Barbara, Calif., USA) apparatus. The particle size was measured at 37° C. with a HeNe laser beam at a detection angle of 90°. The purified latexes were dispersed in distilled water to prepare a stock latex suspension of 5 mg/ml with the aid of Hielscher UP100H probe ultrasonicator (Hielscher USA, Inc., Ringwood N.J., USA) at 80% peak amplitude and 5 mm probe depth in solution for 5 minutes. The stock suspension was diluted 10 times with the aqueous buffer solutions of various pH and constant ionic strength of 0.15M. The pH in the resultant dilute latex suspension was confirmed with a pH meter. The particle size for each sample was measured three times and the average of the triplicate was reported. The intensity-weighted mean diameter was used as the hydrodynamic size since it is calculated directly from the original data and more reproducible than volume-weighted and number-weighted mean diameter. The particle size distribution was evaluated using polydispersity index (PdI). Generally, particles with PdI values smaller than 0.12 are considered monodisperse.

Zeta Potential Measurement

To study the effect of particle composition and pH on surface charge, particles zeta potential was measured using electrophoretic mobility. The stock latex suspension was diluted with buffer solutions of different pH and constant ionic strength of 10 mM. The zeta potential was then measured using a Malvern zeta sizer Nano-ZS (Malvern, Worcestershire, UK).

To measure electrophoretic mobility values of the nanoparticles, the stock latex suspension was diluted with buffer solutions of different pH and constant ionic strength of 10 mM. The measured electrophoretic mobility (μ) is related to the zeta potential (ξ) using the following equation [25]:

$$\xi = \frac{3}{2}\left(\frac{\mu\eta}{\varepsilon_0\varepsilon_r f(\kappa R)}\right)$$

where R is the particle radius, η is the solution viscosity, κ is the inverse Debye length, $\varepsilon_0$ is where R is the particle radius, η is the solution viscosity, κ is the inverse Debye length, $\varepsilon_0$, is the permittivity of a vacuum, $\varepsilon_r$ is the medium dielectric constant, and $f(\kappa R)$ is Henry's function for a 1:1 electrolyte.

Titration Studies

Potentiometric titrations were carried out with a Fisher Scientific Accumet AB15 pH meter (Fisher Scientific, Toronto, ON, Canada). Samples were prepared by suspending 0.050 g of purified particles in 50 mL of 0.05M NaCl. Titrations were run in a thoroughly cleaned, temperature-controlled (25° C.) 100 mL beaker fitted with a pH electrode (Fisher Scientific), and a nitrogen line. The polymer suspension was stirred continuously using a magnetic stirrer. 0.1 M volumetric standard solutions of HCl and NaOH (Fisher Scientific, Toronto, ON, Canada) were used as titrants. The pH of the latex was lowered to 3.0, and nitrogen was bubbled through the latex for 20 minutes prior to titration to remove dissolved carbon dioxide from the system. Nitrogen was blown gently on the sample during the titration to maintain an inert atmosphere. Unless otherwise noted, all data were acquired using a forward (base-into-acid) titration. The suspension was allowed to stabilize for 5 minutes between each titrant addition to ensure equilibrium. The original titration data was corrected by taking into the account the contribution of free H$^+$ and OH$^-$, making the end point clearer. The correction is performed according to equation [26, 27]:

$$[V]_{pH} = [V_{NaOH}]_{pH} + [V_{H^+}^0]_{pH} - [V_{OH^-}^0]_{pH}$$

where [$V_{NaOH}$] is the volume of NaOH added to the dispersion and [$V_{H^+}^0$] and [$V_{OH^-}^0$] are the volumes of HCl and NaOH added to a blank solution of the same pH as in the dispersion. With this correction, assuming the same activity coefficient for H$^+$ and OH$^-$ in the dispersion and in the blank solution, the value of [V]$_{pH}$ should be a constant at equivalence point.

PMAA-g-St Nanoparticles Synthesis

Stable PMAA-g-St latexes with solid contents of up to 7.2% were prepared using the described method. The grafting was performed using a modified aqueous dispersion polymerization method enabling the simultaneous grafting and nanoparticle formation in a one-pot synthesis procedure. The method was found not to require the use of oils and organic solvents. Initially, monomers, surfactants, and initiators are all soluble in water.

As depicted in FIG. 45, the reaction yield (RY %) increases with increasing MAA concentration in the feed. This result may be explained by greater availability of MAA molecules in the proximity of starch and PS 80 at higher MAA concentrations. The starch macroradicals are less mobile than MAA and, thus, their reaction with MAA monomer would basically depend on the availability of the monomer molecules in close vicinity.

Without being bound by any theory, it is thought that as the initiators decompose at elevated temperature, the generated free radicals, on starch, react with solute monomers to form oligomeric radicals. Growing oligomer chains associate with each other increasingly as their molecular weight and concentration rise. At a critical chain length, the formed grafted polymer becomes insoluble in low pH medium (due to protonataion of carboxylic groups, and production of sulphate ions from the initiators) and adsorbs stabilizers to form stable particle nuclei. Once particles have been formed, they absorb monomer from the continuous phase. From this stage on, polymerization mainly takes place within the monomer-swollen particles.

FIG. 45 summarizes the recipes of selected nanoparticle batches, and their respective grafting yields (GY %). Increasing the MAA concentration was accompanied by increase in the grafting yield. This could be explained in terms of greater availability of monomer molecules in the proximity of starch at higher MAA concentrations. The starch macroradicals are relatively immobile. As a result, the reaction of these macromolecules with monomers would essentially depend on the availability of MAA monomers on the starch vicinity.

The successful synthesis of the terpolymer nanoparticles by the new dispersion polymerization method may be explained as follows. Initially, all the reactants are soluble in water. As the polymerization proceeds, the formed terpolymer, at a critical chain length, becomes insoluble in the polymerization medium of low pH due to protonation of carboxylic groups and presence of PS 80 hydrophobic side chains. Moreover, PMAA is known to exhibit lower critical solution temperature (LCST) of 50° C., which means that it can precipitate from aqueous solutions at the polymerization temperature of 70° C. [28-30]. The LCST properties of PMAA may also contribute to the nanoparticle formation. The polymer "nano-precipitates" can adsorb stabilizers to form particle nuclei. Then they can absorb monomers or low molecular weight radicals from the continuous phase and grow larger. With the assistance of the surfactants, the larger nanoparticles are stabilized. Based on the phase transition properties of the formed terpolymer under the polymerization condition, we have developed this new aqueous dispersion polymerization method which enables the simultaneous grafting and nanoparticle formation in a one-pot synthesis process. This method does not require use of oils and organic solvents and thus is advantageous over reverse microemulsion polymerization method.

Mechanism of Grafting and Polymer Composition

Figure 2:
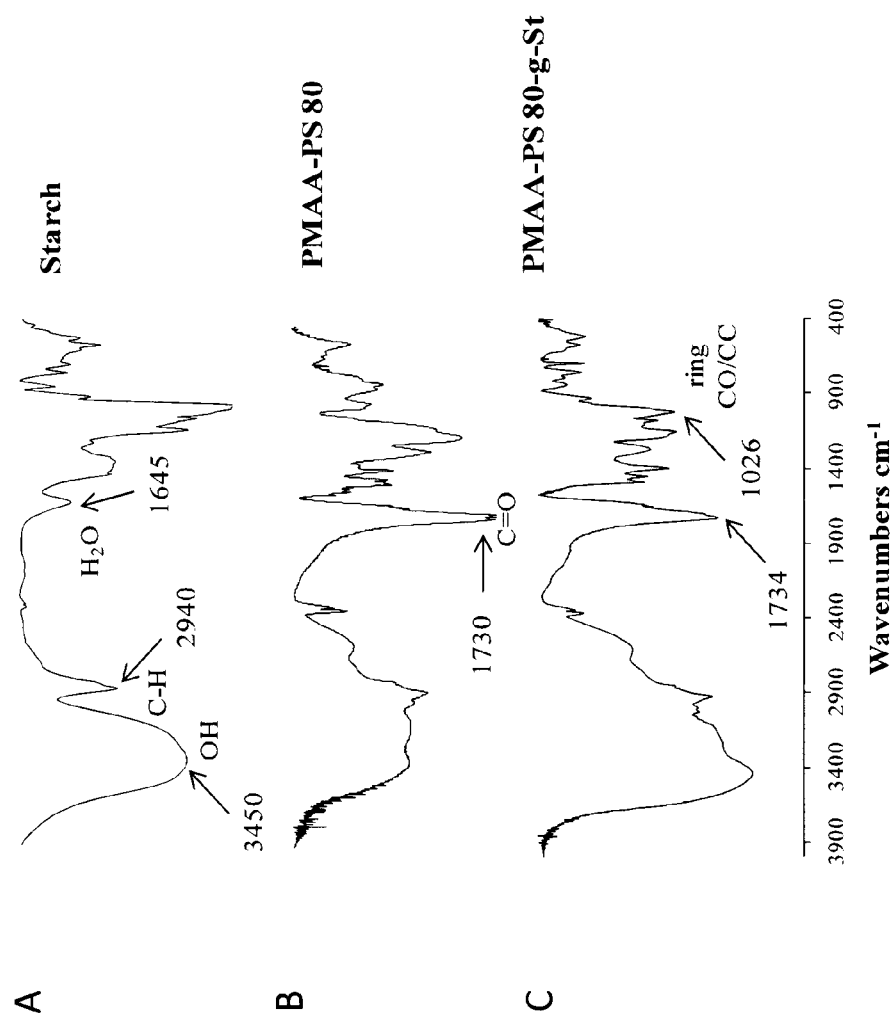
FIG. 2 shows FTIR spectra of (A) Starch, (B) PMAA-PS 80, and (C) PMAA-PS 80-g-St. Major peaks are assigned and explained in the text.

FTIR and NMR studies were used to confirm grafting and study the polymer composition and mechanism of grafting. The FTIR spectra of starch, PMAA and grafted starch are shown in FIG. 2. In comparison with the spectrum of the native starch, the major change is the presence of a carbonyl C=O absorption frequency at 1738 cm$^{-1}$. The peaks at 1166 cm$^{-1}$, 1090 cm$^{-1}$, 1020 cm$^{-1}$, and 954 cm$^{-1}$ in native starch are due to the CO bond stretching. The peaks at 1090 cm$^{-1}$ and 1020 cm$^{-1}$ are characteristic of the anhydroglucose ring CO/CC stretching. A characteristic peak at 1645 cm$^{-1}$ is due to the presence of bound water in starch. A broadband due to hydrogen bonded hydroxyl group (O—H) appears at 3450 cm$^{-1}$ and is attributed to the complex vibrational stretching, associated with free, inter and intra molecular bound hydroxyl groups. The band at 2940 cm$^{-1}$ is characteristic of C—H stretching. The strong OH stretching band at 3450 cm$^{-1}$ in the native starch decreases in intensity following the grafting reaction implying the reaction of starch with MAA through starch OH groups. Also, the grafted polymer exhibits characteristics peaks of pyranose ring vibrations at 520-920 cm$^{-1}$ and also CO/CC ring stretching at 1032 cm$^{-1}$ which is absent in MAA homopolymer confirming the grafting of PMAA onto starch.

Figure 3:
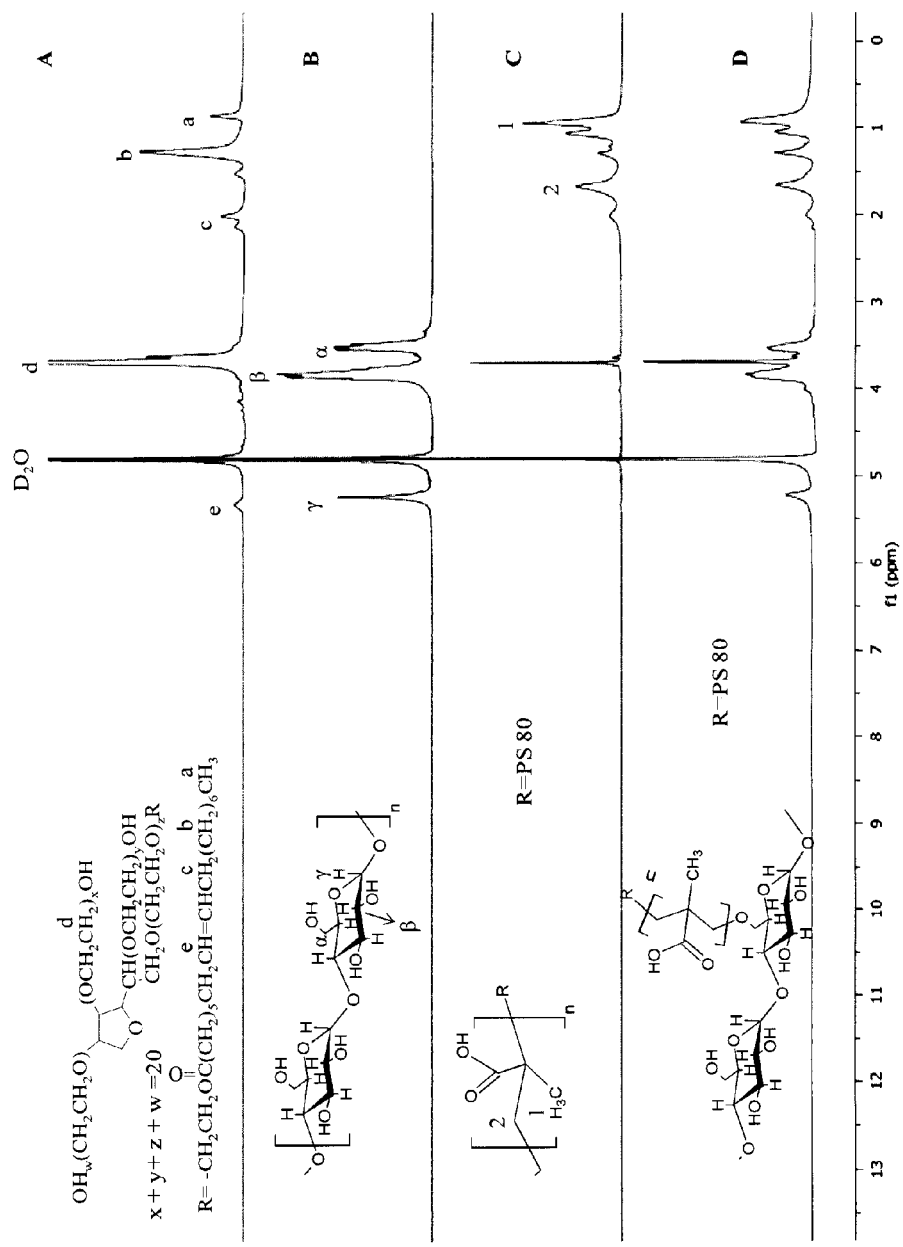
FIG. 3 shows $^1$H NMR spectra of A) PS 80, B) starch, C) PMAA-PS80, D) PMAA-PS80-g-St-2, E) PS80, F) starch, G) DTPA, H) St-DTPA, I) PMAA-PS 80-g-St, and J)
Figure 3:
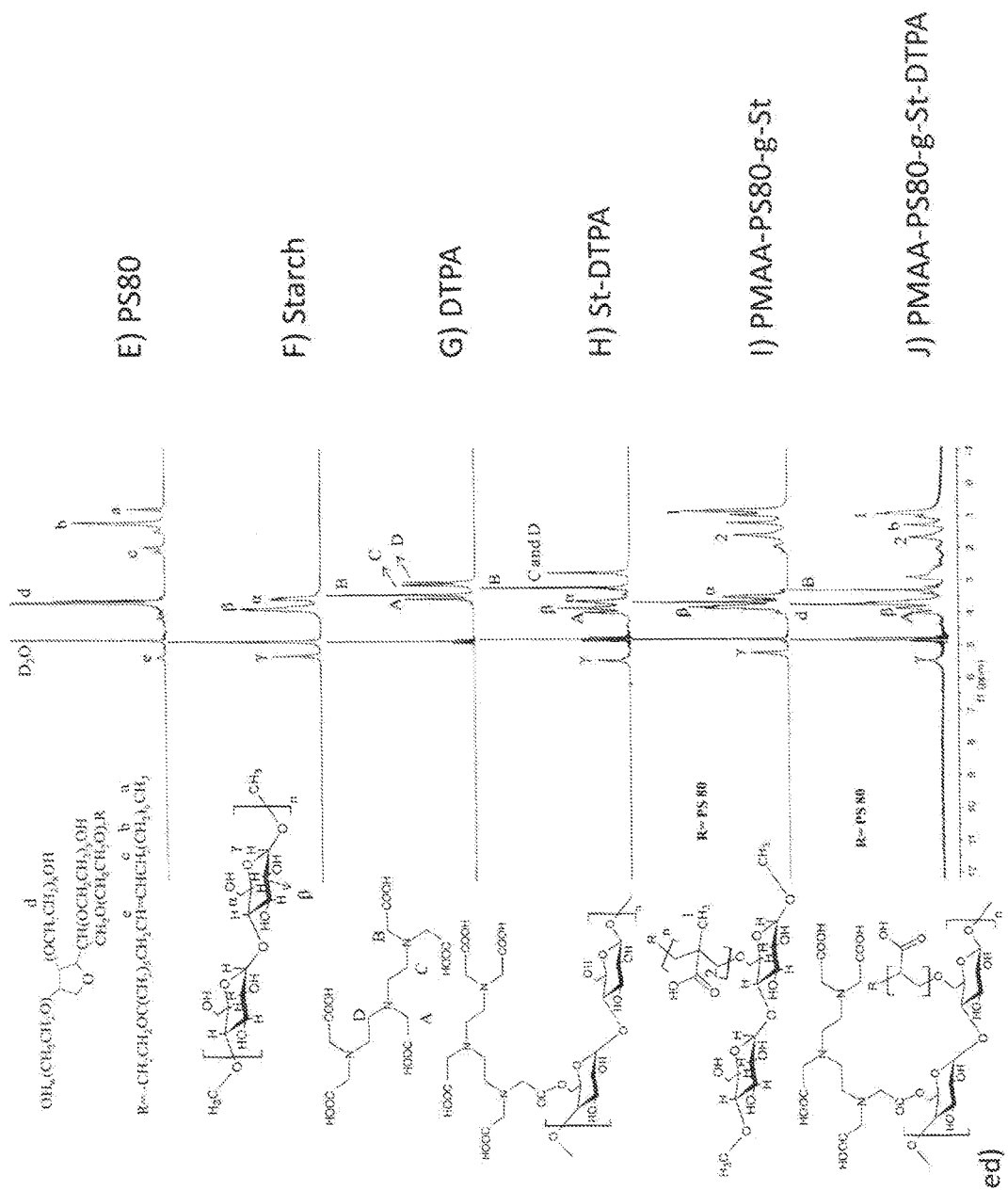

FIG. 3 shows the $^1$H-NMR spectra of a) PS 80, b) soluble starch, c) PMAA and d) PMAA-g-St. The peak at 0.86 ppm corresponds to aliphatic CH$_3$ protons of the PS 80. The peak at 1.27 comes from the aliphatic CH$_2$ region of the surfactant. The large peak at 3.62 ppm is from the CH$_2$ protons of polyethylene oxide regions of the PS 80. The small peak at 5.33 is from CH groups in fatty acid chain (double bond). The smaller peaks in the aliphatic regions belong to the various moieties of fatty acid tails. The starch spectrum exhibits characteristic peaks at 3.5 ppm, which was attributed to CH$_2$ of starch units linked to C6 carbons. The peak at 3.8 ppm is attributed to the hydrogens linked to the CH units joined to C1-C5 carbons. The peak at 5.1 ppm is attributed to the hydrogens of the R—OH hydroxyl groups. Interestingly, the spectrum of homopolymer PMAA exhibits peaks characteristics of both PMAA and PS 80. The peaks at 0.94 ppm and 1.66 ppm are from CH$_3$ and CH$_2$ of the PMAA respectively. The CH peak at 5.33 ppm is absent in the PS 80-PMAA copolymer indicating that PS 80 reacts with the MAA monomers through its double bond. PS 80 contains mono-, di-, and tri-unsaturated fatty acid esters as the primary hydrophobic substituent, which raises the possibility of polymerization pathway for this surfactant. Moreover, the ability of PS 80 to participate in oxidative reactions has been well documented in the literature [31-33]. In fact, PS 80 has been used as an oxidizing reagent for the assessment of drug stability [34]. In the presence of initiators, an alkyl free radical on the surfactant can be formed by hydrogen abstraction. This may occur by various processes, including thermal or photochemical homolytic cleavage of an RH bond. Subsequently, the free radical can participate in graft polymerization reactions by attacking monomer double bond.

The $^1$H NMR spectrum of PMAA-g-St polymer shows peaks characteristics of starch, MAA, and PS 80. There is a small shift in peaks at 0.94, 1.29, 1.66, 3.5 as well as slight change of shape in peak at 3.5 ppm due to alteration of chemical environment brought on by grafting. Also, there is reduction in relative intensity of the peak at 5.1 indicating that the starch hydroxyl groups are participating in the grafting reaction. This peak depends linearly on the amount of anhydroglucose units present in the sample. The areas under the peaks at 3.52, 3.70, and 1.66 were used to calculate the molar ratio of starch, MMA, and PS 80 in the final product and presented in FIG. 45. In addition, using the equivalent point data from the titration studies, we determined the MAA contents in the nanoparticles prepared with different feed monomer ratios. These data are also presented in FIG. 46. There is a relatively good relation between MAA and starch molar ratio in the feed and product. However, only a small fraction of the PS 80 in the feed is incorporated into the final product. The relative molar ratio of the surfactant in the final product decreases as the amount of MAA in the feed is reduced perhaps implying that PS 80 is mainly incorporated into the graft polymer through copolymerization with MAA monomers.

Additional FTIR and H$^1$ NMR spectra are presented in FIG. 4.

The initiation process and free radical formation for grafting of PMAA onto starch can be described by the following reaction schemes [35, 36]:

$$S_2O_8^{2-} \rightarrow 2SO_4^{.-} \quad (1)$$

$$2SO_4^{.-} \rightarrow \text{end products} \quad (2)$$

$$SO_4^{.-} + S_2O_3^{-2} \rightarrow SO_4^{2-} + S_2O_3^{.-} \quad (3)$$

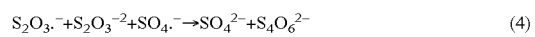

$$S_2O_3^{.-} + S_2O_3^{-2} + SO_4^{.-} \rightarrow SO_4^{2-} + S_4O_6^{2-} \quad (4)$$

$$SO_4^{.-} + H_2O \rightarrow HSO_4^- + HO. \quad (5)$$

$$S_2O_3^{.-} + H_2O \rightarrow HS_2O_3^- + HO. \quad (6)$$

$$St\text{-}H + HO. \rightarrow St. + H_2O \quad (7)$$

$$St\text{-}H + S_2O_3^{.-} \rightarrow St. + HS_2O_3 \quad (8)$$

$$St\text{-}H + SO_4^{.-} \rightarrow St. + HSO_4^- \quad (9)$$

Reaction (3), (5), and (6) favor the continuous formation of various free radical species while reaction (2) and (4) lead to free radical disappearance. It is believed that in presence of thiosulfate there are different free radicals: the sulfate, the thiosulfate, and the hydroxyl radicals which can attack the starch resulting in hydrogen abstraction and the formation of free radicals on the starch molecules. The hydroxyl radicals or starch radicals can attack the MAA double bond and induce the grafting of MAA onto the starch. Thus, subsequent addition of MAA molecules to the initiated chain propagates the grafting chain according to FIG. 5. Finally, the growing grafted chain is terminated by combination or disproportion (FIG. 5). It has to be noted that concurrent homopolymerization of MAA still occurs to some degree due to initiating action of free radicals on MAA monomers.

Morphology and Particle Size of Nanoparticles

All nanoparticles analyzed presented a very homogeneous morphology with particle size around 100-200 nm and a rather spherical shape (FIG. 6A). The nanoparticles have a porous cotton ball like surface morphology. Having a porous structure might be beneficial in terms of faster phase transition in response to environmental stimuli such as pH as well as promoting higher drug loading. There is also some degree of particle aggregation and fusion present; however, this might be due to nature of TEM sample preparation. Particles that are deposited in close proximity on the TEM grid can partly fuse together due to the influence of drying and the electron beam. Such behavior is typical and has been frequently reported for other polymeric nanoparticles such poly(2-hydroxy ethyl methacrylate) particles [37].

As shown in FIG. 47, the particle sizes of the nanoparticles ranged from 70 nm to 310 nm for the terpolymer PMAA-PS 80-g-St-3 depending on the polymer composition and pH. A typical particle size distribution plot from DLS measurement is presented in FIG. 6B. In general, the particle size distribution is relatively narrow with the polydispersity index PdI around 0.09-0.14, except the PMAA nanoparticles (PdI=0.26). Particle size is a crucial parameter in determining the nanoparticles performance in pharmaceutical applications. It affects properties such as response rate (to stimuli such as pH), drug release, cellular uptake as well as particles ability to effectively kill cancer cells. In addition, particle size greatly influences in vivo pharmacokinetics and biodistribution and thus the therapeutic effects of the encapsulated drugs. The particle size of PMAA-g-St nanoparticles makes them amenable to cellular uptake mechanisms, as well as to the enhanced permeability and retention (EPR) effect that imparts passive tumor targeting properties on the nanoparticles [38]. Due to the porosity of the tumor vasculature (the effective mean pore size of most peripheral human tumors is about 300 nm) and the lack of lymphatic drainage, colloidal nanoparticles of suitable size are preferentially distributed in the tumors by the EPR.

The TEM photographs (FIG. 6) of a typical sample illustrate that the nanoparticles have particle size around 100-200 nm, a nearly spherical shape, and porous, cotton ball-like morphology. A porous structure might be beneficial in terms of faster phase transition in response to environmental stimuli such as pH as well as promoting higher drug loading than a dense structure. FIG. 7 shows TEM images of PDEAEM-g-St-2 nanoparticles.

A uniform particle size is also important for drug delivery applications because the distribution of the nanoparticles in the body and their interaction with biological cells are greatly affected by the particle size. Generally, the monodisperse particles exhibit more uniform physical and chemical properties making it easier to formulate more sophisticated intelligent drug delivery systems.

PMAA-g-St Nanoparticles Show pH-Responsive Swelling in Physiological pH Range

The results in FIGS. 8A and 47 demonstrate that the particle size increases with increasing pH from 5 to 7.4 and the pH-dependent change in particle size is a function of MAA/St molar ratio. FIG. 8 demonstrates that the particle size increases with increasing pH from 4 to 7.4 and the magnitude of the increase is determined by the MAA content. For example, the average diameter of PMAA nanoparticles increases 2.2 times from 70.5 nm at pH 4 to 152 nm at pH 7.4, while that PMAA-g-St-4 only increases 1.2 fold, translating to a volume ratio ($V_{7.4}/V_4$) of 10.1 for PMAA and 1.5 for PMAA-g-St-4. In general, the increase in starch content resulted in reduction in pH sensitivity. This can be ascribed to the fact that lower MAA content results in smaller electrostatic repulsion attributed to the lower content of ionized carboxylic groups and thus lower swelling. Different pH sensitivity means a different amount of ionizable and/or ionized carboxylic groups. A lower MAA content results in smaller electrostatic repulsion and lower swelling at pH 7.4, leading to a smaller $V_{7.4}/V_4$ value.

FIG. 8A also shows that a dramatic increase in particle diameter occurs between pH 5 and pH 6, indicating ionization transition in this region, consistent with the volume phase transition pH of PMAA-containing nanoparticles [39]. At pH values lower than the pKa of PMAA, the protonated carboxylic acid groups form extensive hydrogen bonding leading to a collapsed structure. At higher pH values, increased ionization of the carboxylic acid groups results in high electrostatic repulsive forces between polymer chains and thus enlarged the particles.

Effect of pH and PMAA Content on Particles Surface Charge

The zeta potentials of the nanoparticles are summarized in FIGS. 8B and 48. The data show that all nanoparticles have negative surface charges which increase with increment of the pH of the medium from 2 to 7 due to the ionization of the carboxylic acid groups associated with the nanoparticles. Zeta potential is the charge at the electrical double layer, created by ions of the liquid, which exists around each particle. Nanoparticles dispersed in aqueous solutions can be stabilized either by electrostatic stabilization (surface charge) or by steric stabilization (surfactants or other molecules at the particle surface), or by a combination of both. Generally, zeta potential values beyond +/−20 mV are considered characteristics of a stable colloidal dispersion. According to the DLVO theory, aggregation occurs when attractive van der Waals forces between the particles dominate the electrostatic repulsive forces. As shown in FIGS. 8B and 48, most nanoparticle products have zeta potential close or beyond −20 mV at various studied pH values and thus are expected to be colloidally stable. When the PMAA content in the nanoparticles decreases, the zeta potential also decreases. At pH 4, PMAA-g-St-4 nanoparticles have a zeta potential of −2.7 mV, which means that they will have some colloidal stability problem. These data, together with the more negative charges at high pH, suggest that PMAA contributes largely to the surface charge of the nanoparticles.

Characterization of Carboxylic Acid Groups in Starch-Based Nanoparticles

FIG. 9 shows an example of the potentiometric titration of the PMAA-g-St-2 latex dispersion at $C_s$=0.05 N NaCl. Unless otherwise specified, a stabilization time of 5 minutes were allowed between each titrant addition. This is a common procedure in titration of polyelectrolyte latex particles as the relaxation time required to attain equilibrium is normally very long compared to corresponding low molecular weight weak acids. The original titration data was corrected by taking into the account the contribution of free H+ and OH−, making the end point clearer. The correction is performed according to equation 2 [26, 27]:

$$[V]_{pH} = [V_{NaOH}]_{pH} + [V_{H^+}^0]_{pH} - [V_{OH^-}^0]_{pH} \quad (2)$$

Where [$V_{NaOH}$] is the volume of NaOH added to the dispersion and [$V_{H^+}^0$] and [$V_{OH^-}^0$] are the volumes of HCl and NaOH added to a blank solution of the same pH as in the dispersion. With this correction, assuming the same activity coefficient for H+ and OH− in the dispersion and in the blank solution, the value of [$V$]$_{pH}$ should be a constant at an equivalent. We determined an equivalent point of 2.39 ml using the above procedure, shown with an arrow. This value is in good agreement with one determined from the inflection point of the titration curve using simple spreadsheet programming.

Using the equivalent point data from titration studies, we determined the MAA contents for various PMAA-g-St batches with different feed monomer ratio. These data along with their corresponding equivalent point data are presented in FIG. 48.

$pK_a$ values of the nanoparticles of various compositions were plotted against α. The $pK_0$ values were then determined by extrapolating the $pK_a$ values to α=0. The $pK_0$ value was found to depend on starch content in the nanoparticles. It increased almost by 1 unit from 4.9 for PMAA- PS 80 nanoparticles to 5.8 for PMAA-PS 80-g-St-4 nanoparticles. The intrinsic ionization constants of PMAA-PS 80-g-St-1, PMAA-PS 80-g-St-2, and PMAA-PS 80-g-St-3 particles were 5.0, 5.1, and 5.5 respectively (FIG. 9). The increase in $pK_0$ with increasing starch content may be explained in terms of higher degree of hydrogen bonding between the starch hydroxyl groups and the terpolymer acid groups. The change in the ionization behavior of the terpolymer (evidenced by change in $pK_a$ trend) is possibly due to lower charge density of the particles, hydrophilic nature of the starch which could promote higher affinity to water, and more rigid chain structure of starch that would result in more expanded conformation and a higher spatial separation of ionizable groups.

Potentiometric titration was also used to investigate the distribution of the carboxylic acid functional groups within the PMAA-g-St nanoparticles. The gel phase of the hydrogel nanoparticles is permeable to ions. Hence, titrant ions are not restricted to aqueous bulk phase, and can diffuse into the gel phase to neutralize the functional groups which reside within the gel phase. The stabilization time between the bulk and gel phase depends greatly on the distribution of the functional groups to be titrated. Surface accessible groups require shorter equilibrium time while titratable functional groups which are buried beneath the surface require longer time to reach equilibrium.

Forward (base-into-acid) followed by fast backward (acid-into-base) titration studies, allowing a stabilization time of only 30 s between each addition, were used to gain insight into the distribution of acidic groups within the nanoparticles. If the aqueous and gel phases fully equilibrate before the addition of the next volume of the titrant, the forward and the backward titration should fully overlap; however, if equilibrium is not achieved some sort of lag time between the two titrations must be observed. FIG. 10 shows the forward and backward titration curves for PMAA and two different batches of PMAA-g-St with various feed ratio of MAA:St. Both PMAA (FIG. 10A), and PMAA-g-St particles with high MAA contents (FIG. 10B) show good overlap between forward and backward titrations, the PMAA-g-St nanoparticles with high starch content, on the other hand, exhibited good overlap only near the beginning and the end of the titration (FIG. 10C). There was a significant lag at the pH region where the titration of the acidic groups occurred. The fast stabilization time for PMAA and PMAA-g-St particles with lower starch content suggests that the diffusion of $H^+$ ions is not hindered by the gel structure. This is possibly due to existence of carboxylic acid groups near the particle surface. In contrast, the rate of $H^+$ addition in the PMAA-g-St gels with high starch content appears to be faster than the rate of $H^+$ diffusion towards the titratable groups in the gel suggesting that the mass transfer process is partly hindered by gel structure. Based on these results, it is reasonable to conclude that the carboxylic acid groups in PMAA-g-St nanoparticles with high level of starch contents are less accessible to the particle surface than those in PMAA and PMAA-g-St particles of lower starch content.

The acid strength or ease of ionization of a polyacid differs from that of a simple acid in that each successive charge becomes more difficult to remove as the Coulombic field builds up around the polymer coil. The acid strength of a polyacid is represented by "apparent" $pK_a$ values, and is related to degree of ionization ($\alpha$) according to equation 3 [40, 41]:

$$pK_a = pH - \log\left(\frac{\alpha}{1-\alpha}\right) = pK_0 + 0.4343\frac{\Delta G_{el}}{RT} \quad (3)$$

where $pK_0$ is negative logarithm of intrinsic dissociation constant, R is the gas constant, T is the Kelvin temperature, and $\Delta G_{el}$ is an electrostatic interaction term.

The degree of ionization ($\alpha$) is calculated by $$\alpha = \frac{[V]_{pH}}{[V_{eq}]} \quad (4)$$

where $[V_{eq}]$ is the equivalent point volume.

Equation 3 describes $pK_a$ in terms of the sum of a non-electrostatic term ($pK_0$) and an electrostatic interaction term ($\Delta G_{el}$). In FIG. 11 the $pK_a$ values of nanoparticles of various compositions are plotted against $\alpha$. The $pK_0$ values are determined by extrapolating the $pK_a$ values to $\alpha=0$. The $pK_0$ of PMAA nanoparticles was found to be 4.9. This value increased almost by 1 unit by increasing the starch contents. In fact, $pK_0$ of 5.8 was calculated for PMAA-g-St-4 nanoparticles. The intrinsic ionization constant of PMAA-g-St-1, PMAA-g-St-2, and PMAA-g-St-3 particles was 5.0, 5.1, and 5.5 respectively. The experimental value of the $pK_0$ for PMAA is in good agreement with that of linear PMAA and also isobutylic acid perhaps indicating that the majority of carboxylic acid groups at the latex surface have the same environment as in bulk water. As described above, the nanoparticles with lower PMAA content have some of their COOH groups buried beneath the surface. This may decrease the dielectric constant in the vicinity of those carboxylic acid groups and increase the $pK_0$ values.

The increase in the starch content changed the ionization behavior of nanoparticles (FIG. 11). The $pK_a$ values of PMAA and PMAA-g-St with high MAA contents increased sharply initially with increase in degree of ionization. The $pK_a$ values plateau around 25% ionization and start to increase after 40% ionization. This behavior has been documented by other researchers as well, and is attributed to compact/extended coil transformation of the PMAA. Generally, high charge density of the PMAA particles coupled with their compact structure at low ionization degrees lead to rapid initial increase in $pK_a$ values with extent of ionization. To minimize the strong electrostatic repulsive forces the polymer undergoes a conformational change to more extended coil arrangement. The PMAA-g-St particles with higher starch content showed different $pK_a$ profile. The $pK_a$ is significantly higher at low ionization degrees; however, there is almost no increase in the apparent dissociation constant up to 50% ionization. The acid groups appear to behave as isolated units in this ionization region, producing $pK_a$ curves with little slopes. This maybe explained in terms of lower charge density of the particles as well as hydrophilic nature of the starch promoting higher degree of compatibility with the solvent (water) that would result in more extensible conformation and a higher spatial separation of ionizable groups. However, the $pK_a$ values start to increase above 50% ionization due to higher electrostatic repulsive forces.

Effect of Processing Parameters on Particle Size and pH Sensitivity

FIG. 12A shows the effect of SDS concentration on particle size and phase transition. The diameter of the PMAA-g-St particles decreased as the surfactant content increased. The amphiphilic structure of the SDS surfactant helps to stabilize the polymer particles in aqueous solutions and thus making it possible for polymer chains to form smaller particles. The effect of the surfactant amount on the particle size was significant. For example, as SDS changed from 0.17 to 0.69 mmol, the particle size changed from 591 to 298 nm. The SDS levels of below 0.17 mmol (0.05 g) resulted in particle aggregation (annotated by an arrow). Because the PMAA-g-St copolymer is negatively charged on account of ionization of COOH groups and SDS is an anionic surfactant, the absorbed SDS onto the particle surface helps to disperse the particles in water preventing particle aggregation. The ratio of the particle diameter at pH=7.4 to the particle diameter at pH=4 ($D_{7.4}/D_4$) was used to measure the pH responsiveness. The ratio decreased at low SDS levels; however, this is due to poor stability of particles with reduced amount of SDS at low pH values which leads to particle aggregation and misleadingly higher readings by DLS.

The effect of increase in PS 80 concentration on particle size and pH responsiveness is presented in FIG. 12B. The increase in PS 80 amount increased the particle size slightly. The mean particle size increases from 238 nm at 0.13 mmol of PS 80 to 300 nm at 0.27 mmol PS 80. Further increase in PS 80 levels did not affect the particle size. Increasing PS 80 concentration also resulted in reduction in pH sensitivity of particles. As discussed previously, PS 80 can participate in the polymerization reaction by free radical formation as well as through its double bonds; hence it can potentially promote the cross-linking of the polymer chains. Possibly, by increasing the PS 80 concentrations, the intra and inter cross-linking of the particles are increased leading to reduction in pH sensitivity of the nanoparticles.

As the total monomer concentration was increased from 0.156 mol/l to 0.41 mol/l, the average particle diameter increased from 298 to 788 nm (FIG. 12C). When the monomer concentration was further increased to 0.61 mol/L, a dispersion of broad particle size distribution was obtained (data not shown). Further increase in monomer concentration resulted in massive particle aggregation. An increase in monomer concentration generally causes an increase in final particle size as it affects the nucleation process in many ways. First, the grafted polymer chains can stay longer in the continuous phase due to increased solvency of this phase. As a result, the oligomers grow to a longer chain length before precipitation. Second, the propagation rate of the oligomer chains increases. Also the adsorption rate of the stabilizers decreases because of the change in solvency of the medium. All of these effects contribute to an increase in the average size of particle nuclei. Interestingly, the pH sensitivity was not significantly affected as a result of change in monomer concentration in the feed.

FIG. 12D shows the effect of cross-linker molar ratio, X, on particle size and pH sensitivity. The cross-linker molar ratio was calculated using the following equation:

$$X = \frac{\text{mol of cross-linker}}{\text{mol of total monomer}} \quad (5)$$

The particle size increased as a result of increase in cross-linker molar ratio (X). It can be postulated, that at higher cross-linking levels more polymer chains can be cross-linked resulting in larger particles. Also, there is a higher probability of cross-linking and particle diffusion among individual smaller particles to form larger ones. The magnitude of volume phase transition was reduced by increasing the cross-linking levels. The content of cross-linker has a direct effect on the cross-linking density and the mesh size of the hydrogels [4], thus the cross-linker content has a great effect on the swelling behavior of the hydrogels. With increase in cross-linker level, the polymer chain length between the cross-links decreased; as a result, the elastically retractile force which restricts the gel swelling increased dramatically. This explains the reduction in particles pH responsiveness at higher cross-linking levels.

A one-pot aqueous dispersion polymerization method to synthesize PMAA-g-St nanoparticles has thus been exemplified. Dependence of particle size and pH responsive swelling of the nanoparticles on synthesis parameters e.g., MAA/St ratio, surfactant concentration, cross-linker concentration, and total monomer concentration. Adjustment of these parameters shows production of PMAA-g-St nanoparticles with varying particle sizes and pH responsiveness. PS 80 was found to participate in the polymerization making the product a terpolymer. The polysorbate also plays a role in the formation of stable nanoparticles. Presence of starch in the polymerization also appears to impart more uniform particle size distribution. Depending on the MAA/St ratio, the nanoparticle can undergo up to ten-fold change in volume when medium pH changes between 7.4 and 4.0.

The foregoing examples illustrate embodiments of the invention, particularly directed to the synthesis and characterization of nanoparticles.

Production of a nanoparticle includes solubilising a polymer backbone. In the examples, the backbone is provided by starch having a molecular weight in the range of from about 2,600 to about 4,500 Da. As mentioned above, starch is a biocompatible, biodegradable, non-toxic polymer that exists in nature. Starch is composed of glucose units linked by glycosidic bonds. The main components of natural starch are amylose and amylopectin. In preferred embodiments, monomeric units making up the polymer backbone bear hydroxyl groups with a degree of substitution of between 0.5 and 3. This means that on average the monomeric units in the backbone have on average 0.5 to 3 hydroxyl groups, as they occur in the polymer. Amylose, for example, which is a linear glucose polymer thus has a degree of substitution of about 3. The degree of substitution can be in the range from about 1 to about 3, or from 2 to about 3, or it can be about 1, about 2, or about 3. The polymer backbone thus has multiple hydroxyl groups, so is said to be polyhydroxylated. A monomeric unit can be, for example, one or more of a pentose or hexose (e.g., glucose), so it can have 5 or 6 carbons per monomeric unit of the backbone. Preferably, the backbone has 3, 4, 5, 6 or 7 carbons per monomer, more preferably, 5 or 6, most preferably, 6. Examples of relatively high molecular weight polysaccharides (as opposed to e.g., di- or trisaccharides) include callose, laminarin, chrysolaminarin, xylan, arabinoxylan, mannan, fucoidan and galactomannan. Polysaccharides that can be readily broken down in the body, such as amylose can be used for to take advantage of their in vivo behavior, but less digestible polysaccharides such as cellulose can also form nanoparticles of the invention. Naturally occurring starches include maize starch, potato starch, sweet potato starch, wheat starch, sago palm starch, tapioca starch, rice starch, soybean starch, arrow root starch, amioca starch, bracken starch, lotus starch, waxy maize starch, and high amylose corn starch.

Production of a nanoparticle of the invention includes graft polymerizing a monomer to the polymer. In the examples, methacrylic acid was grafted onto starch. Methacrylic acid is an α,β-unsaturated carboxylic acid, and the polymerization production process of the examples is known as free radical graft polymerizing. Such polymerization processes are typically conducted in the presence of a free radical initiator. As the graft polymerizing process proceeds the monomer molecules grow into chains in which the C—C bonds form into carbon based chains and the carboxyl groups from side groups of the chains. The carboxyl group is a Bronsted acid which, depending upon its environment can lose a proton ($H^+$) so exist as a carboxylate group ($CO_2^-$). So when the number of carboxyl groups on a chain is referred to, the form of the carboxyl group, be it $CO_2H$ or $CO_2^-$, is not taken into account. The acid behaviour of the carboxyl groups in the nanoparticle contributes to the properties of a nanoparticle, particularly its behavior at different pHs, and this is discussed elsewhere. When the monomer is an α,β-unsaturated carboxylic acid, the chain formed as part of the nanoparticle contains a carbon based chain having a carboxyl group on alternating carbons.

In the preferred "one-pot" synthesis of the invention, the polymerizing reaction is conducted in the presence of ethoxylated molecules that participate in the polymerizing reaction i.e., form covalent bonds with the forming side chains. In the examples, the ethoxylated molecules are polysorbate 80, commercially available as Tween® 80. The word polysorbate describes a group of compounds having the structure:

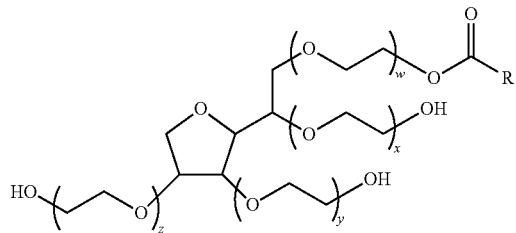

For a given polysorbate, w+x+y+z equals a given number "n" and "R" is one or more of a fatty hydrocarbyl group. The group —O(O)C—R typically corresponds to a naturally occurring fatty acid. In the case of polysorbate 80, n=20 and the R-group is the same as the R-group in oleic acid:

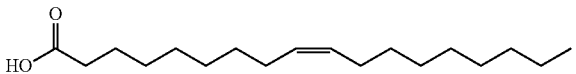 [SMILES: CCCCCCCC/C=C\CCCCCCCC(=O)O]

In fact, another name for polysorbate 80 is polyoxyethylene (20) sorbitan monooleate reflecting the presence of the sorbitan core, oxyethylene groups (—$CH_2$—$CH_2$—O—) and the oleic acid linked to the sorbitan via an ester linkage, and indicating the value of n.

As described in the Examples, the oleic acid R-group of the polysorbate 80 becomes covalently linked to the growing side chain during graft polymerization of the monomer, and the polyethoxylated portions come to reside at the exterior surface of a nanoparticle. The invention includes ethoxylated molecules that display this behaviour during synthesis of the nanoparticle: the polymerizing step is conducted in the presence of the ethoxylated molecules to covalently link the ethoxylated molecules to the polymeric chains. Preferably, the polymerizing step is conducted in the presence of polyethoxylated molecules to covalently link the polyethoxylated molecules to the forming chains and the polymerized product forms into a nanoparticle with polyethoxylated moieties on the exterior of the nanoparticle.

As indicated elsewhere, polyethoxylate portions impart useful practical characteristics to nanoparticles of the invention. The number of oxyethylene units or groups in an ethoxylated molecule incorporated into a nanoparticle can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. It is to be noted that a given polysorbate is often a mixture of molecules, so these numbers refer to averages. Preferably, the polyethoxylated molecule is a sorbitan-based molecule. More preferably, it is a polysorbate.

As characterized for nanoparticles of the invention, the C=C (unsaturation) of the R-group of the polysorbate participates in the polymerization of the nanoparticle synthesis. The polyethoxylated moieties thus become covalently bound to the polymer chain that forms during the synthesis and are covalently bound to the chains of the nanoparticle formed. Polyethoxylated sorbitan having a R(C9-C31)-C(O)O-group wherein the sorbitan is linked to the second polymer through a C—C covalent bond of the R(C9-C31)-C(O)O-group during the graft polymerization is thus an embodiment of the invention. Preferably, the sorbitan is a polysorbate in which the total number of oxyethylene units is at least 10. It is also preferable that the R(C9-C31)-C(O)O-group contains at least one C—C unsaturation which reacts to form the C—C covalent bond in the step of polymerizing. The R(C9-C31)-C(O)O-group can be any of C9, C10, C11, C12, C13, C14, C15, C16, C17, C18, C19, C20, C21, C22, C23, C24, C25, C26, C27, C28, C29, C30, C31. Fatty acids (R—$CO_2H$) having a total number of carbons that is an even number are more common meaning that R-groups in this situation having an odd number are more common which can result in those being preferred.

There are fatty acids other than the oleic acid component of polysorbate 80 that contain unsaturations, such as linoleic acid, arachidonic acid, myristoleic acid, palmitoleic acid, sapienic acid, elaidic acid, vaccenic acid, linoelaidic acid, α-linolenic acid, eicosapentaenoic, erucic acid, etc. It may be found advantageous under various circumstances for a nanoparticle to have incorporated thereinto one or more polysorbates based on one or more of these fatty acids.

As described in the Examples, the relative amounts of polymer and monomer of the graft polymerizing step can vary to obtain nanoparticles having different polymer/monomer ratios. In the context of the nanoparticle, monomer molecules are part of a chain formed during polymerization, and so can also be referred to as monomeric units. The examples show nanoparticles in which the molar ratio of monomeric units of the polymerizing monomer to monomeric units of polymer backbone (i.e., MMA/St) is 0.6 to 4.7. It is possible to obtain other ratios between about 0.1 and about 10, or 0.2 and 9.0, or 0.2 and 8, or 0.2 and 8.0, or 0.2 and 7.0, or 0.3 and 7.0, or 0.3 and 6.0, or 0.4 and 6.0, or 0.4 and 5.0, or 0.4 and 4.0, or 0.4 and 3.0, or 0.5 and 6.0, or 0.6 and 6.0, or 0.7 and 6.0, or 0.8 and 6.0, or between 1 and 5.0, or to obtain a ratio of e.g., about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5 or about 10.

Also described in the Examples, are nanoparticles in which relative amounts of the polyethoxylate molecules and monomeric units of the polymerized monomer are varied, again by varying the amounts of polysorbate 80 and MAA during nanoparticle synthesis. For those particle components, molar ratios of ethoxylated molecules to monomeric units of the polymerized chain from about 0.003 to about 0.01 were indicated. It is possible to obtain other ratios i.e., between about 0.0005 and 1, between about 0.0006 and 0.1, between about 0.001 and 0.1, between about 0.001 and 0.05, between about 0.001 and 0.04, between about 0.002 and 0.04 between about 0.002 and 0.03, between about 0.002 and 0.02 or between about 0.003 and 0.01 or to obtain a ratio of e.g., about 0.0005, about 0.0007, about 0.0009, about 1, about 0.9 about 0.8, about 0.7, about 0.6, about 0.5, about 0.4, about 0.3, about 0.2, about 0.1, about 0.005, about 0.006, about 0.007, about 0.008, or about 0.009.

The graft polymerization of the examples utilized N,N'-Methylenebisacrylamide was used. In the examples, the molar ratio of the polymerizing monomer, MAA and the cross-linker, MBA, ranged from about 3:1 to about 7:1. The amount of the monomer used in the polymerizing step can be between 1 and 20 times the amount of the cross-linking agent, on a molar basis, or it can be between 1 and 15, or between 1 and 10, or between 2 and 10, or between 2 and 9 or between 2 and 8, or between 2 and 7, or between 2 and 6, or the amount of the monomer can be between 3 and 6 times the amount of the cross-linking agent, on a molar basis.

Applications and Uses of Nanoparticles

Various modifications of nanoparticles of the invention have been created demonstrating their useful in a number of applications, particularly related to the medical arts. Modified version of the nanoparticles are possible to obtain, both during synthesis of the nanoparticles, or subsequent to their formulation.

In one application, described in greater detail below, usefulness of nanoparticles of the invention as a drug delivery agent is demonstrated utilizing the drug doxorubicin. Doxorubicin, a member of the anthracycline ring antibiotic family, is a well-known anticancer drug having broad spectrum antitumor activity in a variety of human and animal solid tumours [42, 43]. The drug, however, has a very narrow therapeutic index and its clinical use is hampered by several undesirable side effects such as cardiotoxicity and myelosuppression [44-46]. Another limitation is that the drug is a known p-glycoprotein (P-gp) substrate. P-gp prevents intracellular accumulation of many anticancer agents and, hence, causes a reduction in their cytotoxic activity principally by preventing active uptake and increasing cellular efflux of positively charged amphipathic drugs in an ATP-dependent manner. Overexpression of P-gp is thought to be one of the main mechanisms of multi-drug resistance in cancer cells [47-50].

Association of doxorubicin with a suitable nanoparticulate system might address some of the limitations associated with doxorubicin chemotherapy [51-55]. Targeted delivery of drugs by incorporating them into appropriate nano-carrier system modifies the biodistribution and pharmacokinetics of the drug in vivo [56]. In principle, accumulation of drug-loaded nanoparticles in tumours can be achieved by a nonspecific targeting process known as enhanced permeability and retention (EPR) effect [38, 57]. A leaky vasculature and limited lymphatic drainage, typical of tumour and missing in normal tissue, result in the accumulation of macromolecular drug carrier systems in the interstitial space of a large variety of tumours. The association of doxorubicin with a colloidal carrier such as a nanoparticle could potentially overcome multidrug resistance (MDR). It has been hypothesized that P-gp recognizes the drug to be effluxed out of the tumor cell only when it is present in the plasma membrane and not in cases where it is located in the cytoplasm or lysosomes after its endocytosis [53, 54, 58, 59].

Due to the presence of epithelia-like tight junctions lining the brain capillary endothelium, referred to as the blood-brain barrier (BBB), more than 98% of all new potential brain drugs are ineffective as they are unable to cross the BBB. In the areas of brain delivery of drugs, there have been a number of approaches to overcome the BBB, such as the osmotic opening of tight junctions, usage of prodrugs, and carrier systems like targeted antibodies, liposomes, and nanoparticles [60-63]. For almost a decade, surfactant-coated nanoparticles have been reported to successfully transport drugs across the BBB. Nanoparticle-mediated drug transport depends in part on the coating of the particles, notably with polysorbates, especially polysorbate 80 (Tween 80) [63-67]. Overcoating with these materials leads to the adsorption of apolipoprotein E (ApoE) from blood plasma onto the nanoparticle surface. The particles then seem to mimic low density lipoprotein (LDL) particles and interact with the LDL receptor, leading to their phagocytosis by the endothelial cells lining the BBB. The drug or imaging probes encapsulated in the nanoparticles may then be transported into these cells through receptor-mediated transcytosis [63, 68, 69]. In addition, it has been suspected that processes such as modulation of tight junctions or inhibition of the P-glycoprotein efflux system also occurs, resulting in brain uptake of nanoparticles. To date, many different surfactants have been evaluated. Only polysorbate 80 overcoat has been demonstrated to produce a brain targeting effect following intravenous administration, suggesting a specific role for polysorbate 80 in brain targeting [63]. Efficacy of overcoating with polysorbate 80 is limited due to the fact that the absorbed surfactant on the surface of the nanoparticles can be desorbed in vivo due to replacement by the blood components with high affinity to the particles surface.

In another application, usefulness of nanoparticles of the invention is demonstrated in the area of medical diagnostics, examples described below, showing use in the areas of magnetic resonance imaging (MRI), and fluorescent probes.

Magnetic resonance imaging is a known powerful diagnostic and analytical modality which provides non-invasive 3D visualization of anatomy within an arbitrary plane with superb soft tissue contrast, and enables investigation of vascular and tissue physiology and pathology using quantitative biomarkers [70, 71]. Soft tissue contrast in MR images is multi-factorial, depending on the imaging method, protocol and the relaxation time constants of tissues (e.g. $T_1$, $T_2$). Exogenous paramagnetic contrast agents e.g., $Gd^{3+}$, $Fe^{3+}$, and $Mn^{2+}$ complexes are commonly used which alter the relaxation rates of the surrounding water protons to accentuate vascular and soft tissue contrast in certain applications [72].

Gadolinium ($Gd^{3+}$) is the primary paramagnetic molecule used for MRI due to high relaxation efficiency and magnetic moments [73-75]. However, gadolinium in its free form is highly toxic to the biological systems, hence $Gd^{+3}$ contrast agents are formulated as stable, water-soluble chelates to improve their clinical safety profile [76-78]. The contrast enhancing capacity, termed 'relaxivity', of a $Gd^{3+}$ based contrast agent is directly proportional to the number of exchangeable water molecules in the inner coordination sphere of the $Gd^{3+}$ ion [72-74]. Unfortunately, the complexation of $Gd^{3+}$ by organic chelators reduces the number of inner sphere water molecules. Hence, one of the major challenges in the design of $Gd^{3+}$ based MRI contrast agents is how to increase their relaxivity while minimizing their toxic side effects.

Clinically used $Gd^{3+}$ contrast agents such as diethylenetriaminepentaacetic acid gadolinium (Magnevist®) and diethylenetriamine pentaacetic acid bismethylamide gadolinium (Omniscan®) are non-toxic yet exhibit relatively low $T_1$ relaxivities, rapid vascular extravasation into the extracellular space, non-specific distribution to the whole body, and fast renal clearance. As a result, in clinical practice, multiple injections or infusion of $Gd^{3+}$ contrast agents are required for a single diagnosis [79]. In contrast, non-toxic macromolecular MRI contrast agents such as PEG, poly(L-lysine), poly(glutamic acid), dendrimers, dextran, and supramolecular systems including liposomes, micelles, and other such systems exhibit higher $T_1$ relaxivities and longer residential periods in the bloodstream [80-90]. These macromolecular and supramolecular systems also enable passive targeting of tumors owing to leaky vasculature and under-development of surrounding lymph vessels known as the enhanced permeability and retention (EPR) effect [57, 91].

Starch-based derivatives such as carboxymethyl starch are already used in humans as a plasma expander; it is generally well tolerated in comparison with dextran, due to its lower immunologic potential. Unlike albumin, carboxymethyl starch contains no peptide components that may be immunologically active and may induce antibody production. [92]

As exemplified herein, starch-based nanoparticles, containing polymethacrylic acid-grafted-starch-DTPA (PMAA-g-St-DTPA) can be synthesized in a simple one-pot synthesis process in water. The polymer can bind to gadolinium with high affinity. The synthesis process can be tailored to obtain polymers of suitable molecular weight which is soluble in physiological pH.

Due to abundance of hydroxyl and carboxylic acid groups owing to starch and methacrylic acid components of the system, a wide range of drugs, targeting moieties, and fluorescence probes can be conjugated to the polymer.

Example 2. St-g-PMAA-P80 Nanoparticles for Delivery of Anticancer Drug Doxorubicin The ability of the nanoparticles to load doxorubicin (cationic, Mw=579.98 g/mol) has evaluated using drug uptake studies. Fifty mg of lyophilized nanoparticles is suspended in 10 ml of distilled deionized water (DDIW). The drug is added at a concentration of 0.1-5 mg/ml to the suspension and allowed to adsorb onto the nanoparticle for 24 hrs. The particles are then ultracentrifuged at 30000 rpm for 30 minutes, and the amount of drug in the supernatant assayed using a UV spectrophotometer. Subsequently, the amount of drug loaded into the particles is calculated by subtracting the final drug concentration from the initial drug concentration in the loading solution. The drug loading content and entrapment efficiency are then calculated using the following equations:

$$\text{Drug loading content \%} = \frac{\text{Wt of drug loaded}}{\text{Wt of drug + Wt of nanoparicles}} \times 100\%$$

$$\text{Drug loading efficiency \%} = \frac{\text{Wt of drug loaded}}{\text{Initial Wt of drug in the loading solution}} \times 100\%$$

The particle size and surface charge of PolyGd-Dox nanoparticles were determined by DLS and electrophoretic mobility measurements. The nanoparticles dispersion was diluted to 0.5 mg/ml using PBS with pH=7.4 and ionic strength of 150 mM (size measurements) or 10 mM (ζ-potential measurements). All size and ζ-potential measurements were performed using Malvern Zetasizer Nano ZS (Worcestershire, UK). Each measurement was performed in triplicate and the averages±standard deviations are reported (FIGS. 49A and 49B).

The present data indicate that PMAA-PS 80-g-St nanoparticles are able to load substantial amounts of Dox with no loss of their colloidal stability (FIG. 13). Indicated in FIG. 14 is XRD spectrum of A) doxorubicin in native form, B) PMAA-PS 80-g-St nanoparticles, C) Doxorubicin loaded nanoparticles (LC-50%), D) doxorubicin-loaded nanoparticles (LC=50%) after 6 months storage at room temperature. For doxorubicin clear peaks are visible in the diffractogram indicating the presence of crystalline phase in the native form whereas nanoparticles show a typical amorphous pattern. Absence of peaks in the diffractograms of doxorubicin loaded nanoparticles indicates the phase transformation of crystalline doxorubicin to amorphous doxorubicin.

A frequent limitation of nanoparticulate drug delivery systems is the amount of drug that can be carried. For example, polyalkylcyanoacrylate (PACA) nanoparticles exhibited 3.7% loading content for doxorubicin with the loading efficiency of 74% [93]. Doxorubicin loading content and loading efficiency were 5% and 47% respectively in poly(lactic-co-glycolic acid) (PLGA) nanoparticles [94]. FIG. 46 demonstrates the loading efficiency, size and zeta potential for particles of various loading contents. St-g-PMAA-P80 nanoparticles of the present invention have a high loading capacity, and the loading efficiency remains virtually unchanged and close to 100% even at the highest loading content. Hence, nanoparticles with various drug loads can be prepared readily by varying the nanoparticle-to-drug ratio without noticeable compromise of loading efficiency and particle size and stability. The high loading efficiency reduces waste of expensive drugs. Having a delivery system with high loading content makes it possible to use a smaller quantity of carrier material, which is desirable for repeated injections. Moreover, having particles with high loading content may potentially improve the treatment efficacy as desirable drug levels in target organ and tissues can be achieved provided small amounts of the drug-loaded particles reach their site of action.

Figure 1:
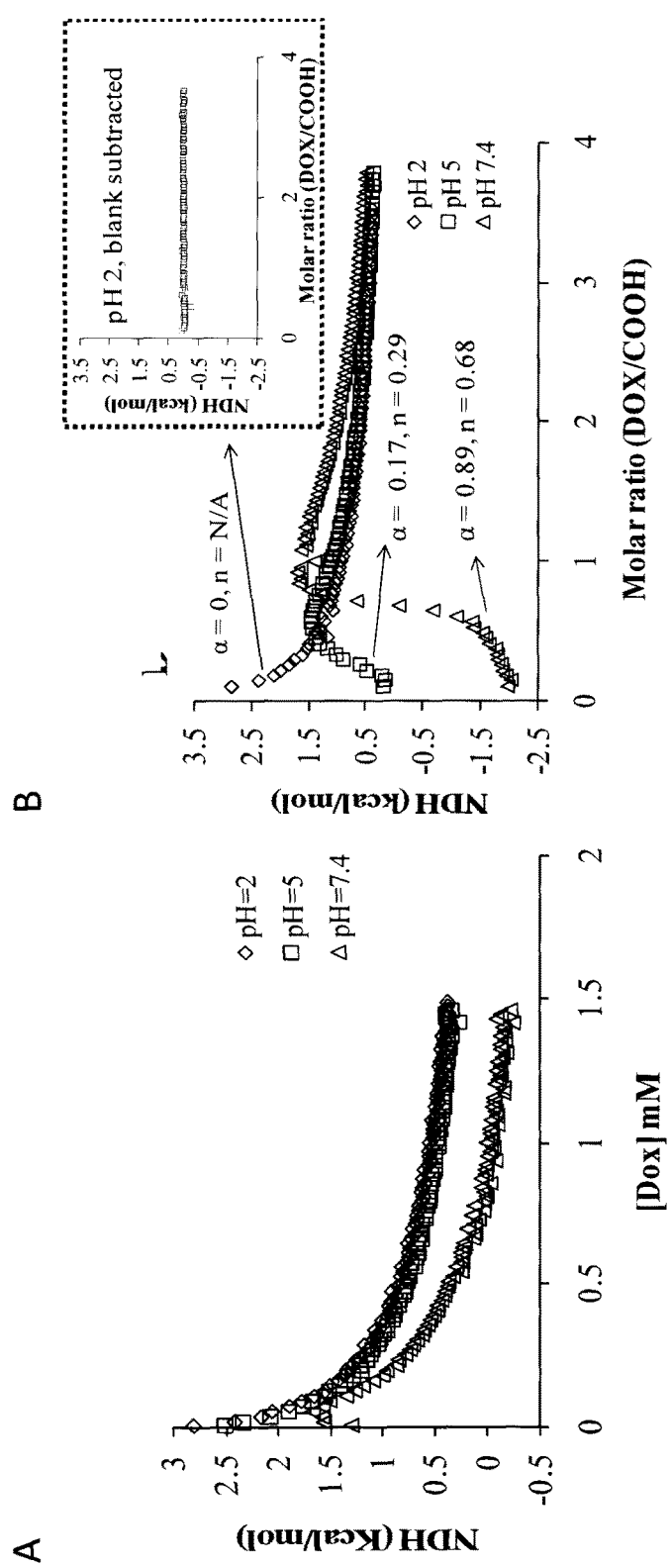
FIG. 1 shows graphical data for the interaction between doxorubicin and carboxylic acid groups of nanoparticles having maximum stoichiometry of 1. (A) The blank differential enthalpy curves of titrating 8.5 mM doxorubicin in buffers of various pH. (B) Differential enthalpy curves of titrating 8.5 mM doxorubicin into 0.1 mg/ml PMAA-g-St-PS80 nanoparticles in buffers of various pH. The ionic strength was kept constant at 0.15 M by addition NaCl.

ITC and FTIR were used to gain insight into the interaction of doxorubicin with the nanoparticles. FTIR data provided evidence for strong electrostatic interactions between carboxylic groups of nanoparticles and amine groups of Dox. Also, there is some evidence for possible hydrogen bonding between the OH groups of starch and the OH and $NH_2$ groups of Dox. The ITC results showed that there is a very strong interaction between Dox and the carboxylic acid groups of the nanoparticles with the maximum stoichiometry of 1. The magnitude of the interaction is strongly dependent on the pH and ionic strength of the medium (FIGS. 1 and 15).

The effect of pH on in vitro release of dox from the particles was investigated using the dialysis method (FIG. 16). The particles exhibited pH-dependent sustained release of dox. The nanoparticles exhibit significantly slower drug release at pH 7.4 and 6 compared to pH 5. There is little or no burst release at pH 7.4 with less than 20% of the drug being released after 90 hrs. The release rate gradually increases at pH 6 with close to 35% of the loaded drug being released after 90 hrs. As the pH drops to 5, there is a significant increase in the drug release rate. This is characterized by initial burst of 20% in the first 8 hours, followed by relatively slower release rates leading to more than 90% of drug being released after 90 hrs. The pH-dependent drug release from the St-g-PMAA-P80 nanoparticles can be explained in terms of the extent of the drug-polymer interaction as well as the pH dependent volume change of the particles. Having a nanoparticulate drug delivery system which exhibits significantly faster drug release in acidic environments will serve as a tool to minimize the drug exposure to healthy tissues while increasing the drug levels in tumor site. It has been shown that human tumors exhibit acidic pH states that range from 5.7 to 7. Rapidly growing tumor cells have elevated rates of glucose uptake but reduced rates of oxidative phosphorylation leading to lactic acid accumulation and subsequent acidity of tumour microenvironment. This persistence of high lactate production by tumors in the presence of oxygen, termed Warburg's effect, provides a growth advantage for tumour cells in vivo. In addition, insufficient blood supply and poor lymphatic drainage, characteristics of most tumours, also contribute to the acidity of tumor microenvironment. The St-g-PMAA-P80 nanoparticles can potentially exploit this pH gradient to achieve high local drug concentrations and to minimize overall systemic exposure.

Example 3. PMAA-PS 80-g-St Nanoparticles for Delivery of Caspase Inhibitor Peptides Caspase inhibitor peptides such as N-benzyloxycarbonyl-Asp(OMe)-Glu(OMe)-Val-Asp(OMe)-fluoromethyl ketone (Z-DEVD-FMK) have been demonstrated to reduce neuronal cell death [95-97], but are unable to cross the blood-brain barrier (BBB).

For effectively loading poorly water-soluble drugs, such as caspase inhibitor peptides, a lipid chain was introduced to the polymer. In a typical reaction, myristic acid (10 mg, 0.043 mmol) was incubated with EDC (34 mg, 0.175 mmol) and NHS (40 mg, 0.350 mmol) in 5 ml of DMSO for 1 h at room temperature, and PMAA-PS80-g-St (200 mg) dissolved in 5 ml of DMSO/H$_2$O mixture was added. The mixture was stirred at room temperature for 24 h and then purified by dialysis against DDIW (2 L, MWCO=12000 kDa) for 48 h, changing the dialysate every 12 h. The solid lipid-polymer was obtained by freeze drying. Z-DEVD-FMK was used as a model caspase inhibitor peptide. To prepare the self-assembled nanoparticles, 10 mg of lipid-polymer was dissolved in 2.0 ml of DDI water. The lipid polymer solution was then placed in an ice bath, and while under ultrasonication, using a Hielscher UP100H probe ultrasonicator (Hielscher USA, Inc., Ringwood N.J., USA), 200 μL (5×40 μL) of peptide solution (1 mg/ml in CH$_3$CN/H$_2$O (2/8, v/v) mixture) was added in small increments to the lipid polymer solution every 10 seconds. The particle size of peptide-loaded NPs was measured by using a Zetasizer nano system to be 37 nm. The loading efficiency was found higher than 91%.

Example 4. Particle Uptake by MDA-MB435/LCC6 Human Breast Cancer Cells

The uptake of the fluorescamine labeled nanoparticles by MDA-MB435/LCC6 cells was investigated using fluorescence microscopy and flow cytometry. Fluoresceinamine (FA) was covalently linked to the NPs. Briefly, 200 mg of the NPs were dispersed in 20 ml of DDIW, followed by addition of 50 mg of NHS and EDC. After 45 minutes, the reaction was started by adding 10 mg of FA. The mixture was protected from light and stirred for 24 hrs at room temperature. The pH was then adjusted to 7.4 and the particles were then washed three times followed by centrifugation to remove any unreacted dye.

The fluorescamine was covalently bound to the particles and therefore there was no leakage of the dye from the particles. After incubation the cells were washed exhaustively with cold PBS to ensure that the loosely bound particles to the cell surface are washed off Serial z-sections of the cells, each 1 μm in thickness, demonstrated fluorescence activity in all the sections between 3 and 15 μm from the surface of the cells, indicating that the nanoparticles were both bound to the cell surface as well as internalized by the cells (data not shown). Staining of the nuclei (DAPI) and cell membrane (Vybrant™DiI) prior to incubation of the cells with nanoparticles allowed for the discrimination of particle uptake by membrane-bound vesicle pathways (i.e. endocytosis), or through penetration of the cell membrane. If the particles enter the cell by passive diffusion, there would be expected to be no membrane bound vesicles surrounding them, and as a result the fluorescence signal from the nanoparticles would not be expected to co-localize with the signal from intracellular vesicles (Vybrant™ DiI). However, if nanoparticles were taken up into the cell via endocytosis-like mechanisms, a membrane-bound vesicle would surround the particles, and the signal co-localization from the labelled nanoparticles and stained membrane vesicles would be expected. FIG. 17A demonstrates particle uptake by the wild-type (MDA MB435-WT) and multidrug resistant (MDA MBA435-MDR1) cells. In the absence of nanoparticle incubation with the cells, there was no signal using the FITC filter, and there were limited numbers of small, intracellular fluorescent foci of internalized Vybrant™ DiI-stained cell membrane representing membrane-bound vesicles (Control for both wild type and MDR cells). However, following incubation with nanoparticles for 4 hours, a greater number of larger fluorescent foci were observed in both cell lines. These red fluorescent foci, which may represent membrane-bound vesicles formed from stained cell membrane (Vybrant™DiI), aligned with the fluorescent green foci observed from the nanoparticles signal (FITC). As shown in FIG. 17B, the nanoparticles loaded with Gd$^{3+}$ appear as electron-dense deposits. This suggests that St-g-PMAA-P80 nanoparticles are taken up by the cells via membrane-bound vesicles, and shuttled to the perinuclear region of the cytosol in both wild type and resistant human breast tumor cells.

Flow cytometry was used to measure the cellular uptake of the St-g-PMAA-P80 nanoparticles in MDA 435 cell line (both WT and MDR1). As shown in FIG. 18, the cellular level of the nanoparticles progressively increased in both WT (A,B) and MDR1 (C,D) cells with incubation time at 37° C., and did not reach saturation up to 24 hrs of incubation. Interestingly, the resistance cell line showed faster and higher extent of particle uptake compared to the wild type. The mean fluorescence intensity for WT and MDR1 cells were 896 and 1897 respectively after one hour. These values increased to 11510 and 18574 after 24 hours. The data show that nanoparticle uptake is relatively rapid at 37° C. as we were able to see significant uptake within an hour. Alternatively, when the cells were incubated at 4° C., there was a significant reduction in the cellular uptake of the particles. The cells incubated at 4° C. showed only slightly higher fluorescence intensity values compared to the background, which may be representing the cell surface bound particles without being internalized. The significant reduction in the cellular uptake of particles at low temperature, a general metabolic inhibitor, indicates that the cellular uptake of the nanoparticles is an energy dependent process. Because endocytosis is an active process, uptake by this mechanism slows at low temperature; pronounced reductions in nanoparticle uptake, as observed here, are consistent with internalization via endocytosis, rather than diffusion across the plasma membrane.

Example 5. In Vitro Assessment of NPs Anticancer Efficacy Against Wild Type and Multidrug Resistant Human Breast Cancer Cell Lines The efficacy of free Dox and Dox-loaded nanoparticles against MDA-MB435/LCC6 breast cancer cell lines were evaluated in both wild type and resistance cells (FIG. 19). The cells were treated with increasing concentrations of doxorubicin or doxorubicin-loaded nanoparticles for 24 hrs and 48 hrs, and the cell viability was determined using MTT assay. Both free Dox and Dox-loaded nanoparticles were equally effective against the wild-type cell line (FIG. 19A, B). All treatments elicited cytotoxicity on wild-type cells in a dose-dependent manner. The IC50 values for 24 hrs treatments were 0.34 µg/ml and 0.32 µg/ml for free Dox and the drug-loaded nanoparticles respectively. These values decreased to 0.07 µg/ml (free Dox) and 0.06 µg/ml (nanoparticles) by increasing the treatment length to 48 hrs. The data indicate that loading of the doxorubicin into the nanoparticles does not result in loss of drug activity.

The cytotoxicity of the free drug and the drug-loaded nanoparticles were also evaluated in the MDR1 cell lines. Increasing Dox concentrations for MDR cells did not decrease the cell viability at the same magnitude as it did for the wild type. The IC50 of the free Dox in the resistance cells were 57.01 µg/ml and 7.69 µg/ml for the 24 hrs and 48 hrs treatments respectively (FIG. 19C,D). The Dox-loaded nanoparticles performed significantly better compared to the free drug with the IC50 values of 2.99 µg/ml and 0.62 µg/ml for 24 hrs and 48 hrs incubation times. It appears that increasing the treatment time results in higher killing. More importantly, the loading of the doxorubicin into the nanoparticles results in up to 19-fold reduction in IC50 values in the resistance cells.

Example 6. Synthesis of Novel DTPA-Containing St-g-PMAA-P80 Polymers and Nanoparticles Preparation of Dual Mode Nanoparticles The schematic structure of PF-NPs and SA-NPs and their preparation procedures are illustrated in FIG. 20 and prepared as indicated below.

Preparation of the $Gd^{3+}$ Loaded PMAA-g-St-DTPA Polymer (PF-NPs)

The PMAA-g-St-DTPA was synthesized by first conjugating diethylenetriaminepenta acetic acid bisanhydride (DTPA-bis-anhydride) to the starch followed by grating polymerization of MAA.

Synthesis of DTPA-bis-anhydride:

DTPA-bis-anhydride was synthesized according to the method described by Andersen et al. [98]. DTPA (5 g, 0.0125 mole), acetic anhydride (3.62 ml), and pyridine (4.61 ml) were combined in a 50 ml 3-necked flat-bottomed reactor fitted with a thermometer, a mechanical stirrer, and reflux condenser cooled with cold water. The mixture was heated with stirring to 60° C. in an oil bath over night. The flask was rinsed with isopropyl alcohol (IPA), and the content was filtered on a Büchner funnel, washed with acetonitrile twice and dried over night under vacuum.

Synthesis of St-DTPA:

Soluble starch (3 g) was dissolved in 50 ml of dry DMSO followed by addition of 1.5 g of DTPA-bis-anhydride. The solution was stirred at room temperature for 24 hrs, dialysed against DMSO for 24 hrs, and subsequently against water for another 24 hrs. The product (St-DTPA) was then dried in an oven at 50° C. overnight.

Synthesis of PMAA-g-St-DTPA Polymer:

The PMAA-g-St-DTPA polymer was synthesized using a modification of a one-pot dispersion polymerization method developed previously in our lab [99]. Briefly, 1.55 g of St-DTPA was dissolved in 150 ml of distilled water by heating at 70° C. for 30 minutes. The solution was purged with $N_2$ for 30 minutes to remove any dissolved oxygen. Subsequently, 0.25 g of SDS, 1.5 g of PS 80, 0.18 g KPS and 0.25 g STS were added to the St-DTPA solution while under stirring. After 10 minutes, the reaction was started by addition of 2 g of nitrogen purged MAA. Opalescence appeared after 5 minutes and the reaction was continued for 8 hours at 70° C. to ensure complete grafting. The product was washed extensively with warm water twice and extracted with methanol followed by dialysis to remove any unreacted materials and homopolymers. The purified particles were then dried in a vacuum oven for 24 hours, and stored in a desiccator for future use.

Loading of $Gd^{3+}$ onto PMAA-g-St-DTPA Polymer:

The PMAA-g-St-DTPA polymer (0.5 g) was dispersed in 10 mL of DDIW water. The pH was adjusted to 6.5 using 0.1N NaOH. 10 ml of aqueous solution of gadolinium chloride hexahydrate (10 mg/ml) was then added drop wise while stirring, and the pH of the reaction was kept at 6.5 with the NaOH solution throughout the experiments. Stirring was then continued for 1 hr, and the product was dialysed exhaustively against 0.9% NaCl until no free $Gd^{+3}$ was detected in the wash medium using the xylenol orange test [100]. The product was then freeze-dried and stored for future use. The $Gd^{+3}$ content in the product was measured using inductively coupled plasma atomic emission spectrography (ICP-AES, Optima 7300, PerkinElmer, Shelton, USA).

DTPA bisanhydride (DTPA-A) was added to a suspension of swollen St-g-PMAA-P80 in dry DMSO at ambient temperature. The suspension is agitated at ambient temperature for 24 hrs, and then cooled with ice-water bath. Distilled water (100 ml) is added and the suspension is agitated at room temperature for 1 hr. The polymer is dialyzed against water for 48 hrs, and collected by ultracentrifugation at 30000 rpm for 30 minutes. Alternatively, the DTPA can be covalently linked to the starch first according to the procedure outlined above, and the resultant Starch-DTPA can be used to synthesize the St-g-PMAA-P80 using the method described previously. The resultant DTPA containing St-g-PMAA-P80 can then effectively load $Gd^{+3}$. Briefly; 0.5 gram of the polymer is dispersed in 10 mL of DDIW water. The pH is adjusted to 6.5 using 0.1N NaOH. 12.5 ml of aqueous solution of gadolinium chloride hexahydrate (10 mg/ml) is then added drop wise while stirring, and the pH of the reaction is kept at 6.5 with the sodium hydroxide solution throughout the experiments. Stirring is then continued for 24 hrs, and the resulting product is purified by dialysis against 0.9% NaCl until no free $Gd^{+3}$ is detected in the wash medium using the xylenol orange test. The product is then freeze-dried and stored for future use. The gadolinium content is then measured using inductively coupled plasma atomic emission spectrography (ICP-AES).

The stability of the resultant lanthanide complexes within the biological environments is an important consideration, as free $Gd^{3+}$ is highly toxic. DTPA is a strong chelator of gadolinium. The DTPA-gadolinium complex is known to be stable in biological systems. The size of the nanoparticles can be adjusted by modifying the reaction parameters such as monomers concentrations, surfactant levels, etc. Alternatively, DTPA can be incorporated into the preformed St-g-PMAA-P80 nanoparticles through reaction with starch hydroxyl groups. Our data show that DTPA containing nanoparticles can form a stable complex with gadolinium (log $K_d$=17.5).

In order to obtain quantitative information about the efficiency of $Gd^{+3}$-loaded nanoparticles as MRI contrast agents, we determined the relaxivity at 3.0 and 7.0 T. The T1 values of various concentrations of nanoparticles were determined in vitro, and a linear fit between 1/T1 and concentration was performed to obtain the relaxivity. The relativity values are listed in FIGS. 49A and 49B. The relaxivity for Omniscan, which is a clinically available MRI contrast agent, has been included for comparison. The Gd loaded St-g-PMAA-P80 showed significantly higher relaxivity values compared to the Omniscan. The relaxivity is found to be dependent on the magnetic field strength which is expected for the macromolecular contrast agents.

In one example, the nanoparticles were loaded with Dox. Briefly, 50 mg of lyophilized nanoparticles were suspended in 10 ml of DDIW. Dox was added in concentration of 2.5 mg/ml to the suspension and incubated with the nanoparticle for 48 hrs. The particles were then ultra-centrifuged at 96,000 g for 30 minutes, and washed trice with DDIW. The PF-NPs were then freeze-dried and store at 4° C. for future use.

Preparation of Self-Assembled Nanoparticles (SA-NPs)

The PMAA-PS 80-g-St soluble polymer was synthesized using the method described above with slight modifications. There was no cross-linker (MBA) and the amount of PS 80 was increased to 1 gram.

Next, Hilyte Fluor™ 750 was covalently linked to the polymer using the method described above. Finally, to prepare the self-assembled nanoparticles (SA-NPs), 8 mg of the polymer was dissolved in 1.8 ml of sterile 5% dextrose. The polymer solution was then placed in an ice bath, and while under ultrasonication, using a Hielscher UP100H probe ultrasonicator (Hielscher USA, Inc., Ringwood N.J., USA), 170 µl (5×34 µl) of doxorubicin solution (12 mg/ml in 5% dextrose) was added in small increments to the polymer solution every 30 seconds. The ultrasonication continued for another 10 minutes. Addition of the Dox resulted in spontaneous formation of nanoparticles. The SA-NPs were then passed through ion exchange resins, Sephadex G50 fine (GE Healthcare, Piscataway, N.J., USA) to remove unbound Dox.

As illustrated in the schematic in FIG. 20, in the case of PF-NPs, the NIR fluorescent probe was covalently bound and the drug was loaded into the preformed cross-linked PMAA-Ps 80-g-St nanoparticles. The SA-NPs were spontaneously formed in aqueous medium with covalent linkage of the dye followed by addition of the Dox to the soluble PMAA-PS 80-g-St polymer. The linkage of HiLyte Fluor™ 750, and ionic complexation of the doxorubicin to the carboxylic acid groups of the PMAA-PS 80-g-St polymer are believed to increase the overall hydrophobicity, resulting in the formation of dense nano-structures which is stabilized by the presence of PS 80 and ionic repulsive forces on the particle surface due to presence of negatively charged carboxylic acid groups.

SA-NPs and PF-NPs exhibit particle sizes of 62±5 nm (PdI=0.12) and 137±3 nm (PdI=0.07) respectively (FIGS. 23D-E). TEM photographs illustrate that the particle size are in good agreement with the DLS data, and suggest different morphology between SA-NPs and PF-NPs. PF-NPs are nearly spherical with a porous cotton ball structure while the SA-NPs are less spherical and exhibit a more compact overall morphology. The surface charge of the nanoparticles was found to be negative, with 4-potential values of −38±1 (SA-NPs) and −35±5 (PF-NPs).

Example 7. Cytotoxicity of St-DTPA-g-PMAA-P80 Chelated $Gd^{+3}$ vs. Free $Gd^{+3}$ Cell Viability As a preliminary assessment of the safety of the nanoparticles for in vivo use, their toxicity was assessed against free gadolinium solution using isolated rat hepatocytes. This model has been used for rapid toxicity screening and has demonstrated in vitro-in vivo toxicity extrapolation. Hepatocyte viability was assessed microscopically by trypan blue (0.1% w/v) exclusion test which determines plasma membrane disruption. Hepatocyte viability was determined every 30 min during the 3 h incubation, and the cells were at least 80% viable before use. 800 µl of each sample was added to the hepatocytes. There was no statistically significant difference between control blank, and $Gd^{+3}$-loaded polymer and nanoparticles. The free $Gd^{+3}$ showed significant hepatocyte toxicity, resulting in less than 15% hepatocyte survival upon exposure to 1.5 mg/ml of gadolinium solution respectively after 240 minutes (FIG. 24). Exposure of hepatocytes to the same dose of $Gd^{+3}$ loaded in the polymer and nanoparticles for 240 min resulted in the survival of 65% and 68% for polymers and nanoparticles respectively. The data indicate loading $Gd^{+3}$ to St-DTPA-PMAA-P80 polymer/nanoparticles significantly reduces the toxicity of the gadolinium.

Cell Viability

As a preliminary assessment of the safety of the nanoparticles for in vivo use, their toxicity was assessed against free gadolinium solution using isolated rat hepatocytes. This model has been used for rapid toxicity screening and has demonstrated in vitro-in vivo toxicity extrapolation. Hepatocyte viability was assessed microscopically by trypan blue (0.1% w/v) exclusion test which determines plasma membrane disruption. Hepatocyte viability was determined every 30 min during the 3 h incubation, and the cells were at least 80% viable before use. 800 µl of each sample was added to the hepatocytes. There was no statistically significant difference between control blank, and $Gd^{+3}$-loaded polymer. The free $Gd^{+3}$ showed significant hepatocyte toxicity, resulting in less than 15% hepatocyte survival upon exposure to 1.5 mg/ml of gadolinium solution respectively after 240 minutes (FIG. 25). Exposure of hepatocytes to the same dose of $Gd^{+3}$ loaded in the polymer and nanoparticles for 240 min resulted in the survival of 65% and 68% for polymers and nanoparticles respectively. The data indicate loading $Gd^{+3}$ to PMAA-PS 80-g-St-DTPA polymer significantly reduces the toxicity of the gadolinium.

Example 8. Conjugation of Near Infrared Dye (HiLyte Fluor 750) to the St-g-PMAA-P80 Polymer and Nanoparticles The near infrared dye (HiLyte Fluor 750) is covalently linked to the St-g-PMAA-P80 using carbodiimide chemistry (FIG. 43A). Briefly, 20 mg of the polymer/nanoparticle is dispersed in DDIW water followed by addition of EDC (48 mg) and NHS (45 mg) and stirring for 90 minutes to activate the carboxylic groups on the St-g-PMAA-P80. FIG. 43B shows the visual effects of NIR conjugation with the nanoparticle. Subsequently, 200 µl of the Hilyte Fluor 750 hydrazide (1 mg/ml) is added and the mixture was stirred overnight in the dark. The product is then purified by dialysis against water followed by freeze drying and storage at −20° C. for future use. The St-g-PMAA-P80 labelled with a NIR dye shows fluorescence emission at 820 nm (FIG. 43C).

Example 9. Biodistribution and Targeting Ability of the St-g-PMAA-P80 In Vivo Whole Body Fluorescence Imaging Nanoparticles co-loaded with a NIR dye, HiLyte Fluor 750, and doxorubicin were prepared. St-g-PMAA nanoparticles, synthesized as described above and which had been freeze dried and stored in a desiccator, were used. 100 mg of the nanoparticles were dispersed in 2 ml DDIW, and 30 mg of EDC/NHS were added. After 30 minutes 0.2 ml of Hilyte Fluor 750 hydrazide (1.25 mg/ml) were added while under stirring. The mixture was protected from light and stirred at room temperature for 24 hrs. Finally, the product was neutralized to pH 7.4 and purified by successive washing with water and centrifugation. The nanoparticles were then loaded with Dox using the method described above.

The nanoparticle size found to be 137±3 nm with a polydispersity index of 0.12. The diameter of these nanoparticles is thus below the pore size of the permeable vasculature found in many solid tumours, suggesting that nanoparticles should be able to selectively accumulate in solid tumors by means of the enhanced permeability and retention effect (EPR). The particles were spherical and showed a porous cotton ball structure The overall surface charge of the nanoparticles was found to be negative with zeta potential values of −35±5. The negative surface charge can be attributed to the presence of the carboxylic acid groups and a small amount of remnant anionic surfactant, SDS, on the surface of the particles. The net surface charge of the nanoparticles have a pronounced effect on their stability as well as the adsorption of different physiological lipoproteins in systemic circulation and could play a critical role in the clearance of the nanoparticles in vivo. HiLyte Fluor 750 content was 3.9±0.02%.

FIG. 26 shows the in vivo fluorescence images of a mouse lying on its back. Due to very high fluorescence signal intensity of the formulations, and the near infrared emission wavelength, good tissue depth penetration with low background interference is possible. High level of fluorescence was detected 1 hr post-injection throughout the body with the highest signal level coming from bladder indicating the excretion of the polymer by the renal route. The detection of signal throughout the body at early time points is possibly due to combination of the particles being in the blood and particle deposition in skin and subcutaneous fatty compartments. High fluorescence recorded from the highly perfused organs, such as liver and heart could be accounted for as the combined activity of the circulating blood passing through organs, as well as that due to particle uptake by cells of the reticuloendothelial system (RES) recruited by the liver. The enhanced uptake in the liver is largely attributed to the macrophages residing in these tissues, which are responsible for capturing polymers circulating in the blood That being said compared to majority of the formulations discussed in the literature, the liver uptake appears to be relatively low.

The formulation appears to be cleared from the body over time as the fluorescence levels are almost back to the baseline after 9 days. There is only small signal detected in the liver after 9 days, and the polymer appears to be completely eliminated from the body after 14 days.

Non-invasive real-time fluorescence imaging was utilized to track the biodistribution and tumor accumulation of nanoparticles in Balb/c mice bearing orthotopic murine EMT6 breast tumors. Owing to the near NIR emission of HiLyte Fluor™ 750 ($\lambda_{ex}$=754 nm, $\lambda_{em}$=778 nm) and the high fluorescence intensity of these nanoparticles, it is possible to set detection limits such that background levels of autofluorescence can be reliably excluded (FIG. 26A).

FIG. 26A presents whole body images of mice at time zero (baseline) and following injection of each formulation into the lateral tail vein at various times. At one hour post injection a clear fluorescence signal is detectable throughout the body, due to distribution of nanoparticles within the blood, skin, organs and subcutaneous fat. As depicted in FIG. 26A, SA-NPs and PF-NPs exhibited distinct biodistribution profiles. One hour following injection of SA-NPs, strong fluorescence signal was observed in the urinary bladder (FIG. 26A, upper panels), indicating excretion by the renal route. The bladder signal reduced significantly 6 hours post injection; however, strong fluorescence could still be detected throughout the body suggesting both a fast and slow component to the elimination of the SA-NPs. Importantly, mice receiving SA-NPs exhibited a strong fluorescence signal within tumor tissue, while other perfused tissues such as the liver showed substantially lower levels of nanoparticle accumulation. Consistent with this, inoculated tumors could be delineated from the surrounding histologically normal tissue, suggesting a relatively great accumulation of SA-NPs within tumors. Importantly, such fluorescence signatures persisted beyond 1 week.

A different pattern of biodistribution was observed for PF-NPs. Substantial accumulation was noted in liver and spleen at one hour post injection, as revealed by the strong fluorescence observed in these organs. Moreover, these particles were not excreted efficiently via the renal route as no significant fluorescence accumulation was detected during the first 6 hours in the bladder. Although not studied systematically here, it is worth mentioning that higher levels of fluorescence in fecal matter were observed in those mice injected with the PF-NPs (personal observation), suggesting clearance of these particles through a hepatobiliary route largely. At one hour post injection the tumor could be differentiated from the surrounding tissue, but the extent of PF-NP accumulation in the tumor appeared to be substantially lower than SA-NPs.

The time-dependent excretion profiles of SA-NPs and PF-NPs were further quantified using the Xenogen IVIS system and plotted in FIG. 26B. SA-NPs initially showed a rapid clearance phase, possibly due to clearance through urinary excretion, followed by a slower clearance at later time points. The average whole body NIR fluorescence intensity of SA-NPs at 15 minutes post injection was 1.5±0.2×10$^8$ (p/s/cm$^2$/sr)/(µW/cm$^2$). It rapidly decreased to 0.87±0.05×10$^8$ (p/s/cm$^2$/sr)/(µW/cm$^2$) by 6 hrs. The body fluorescence was measured to be 0.63±0.09×10$^8$ (p/s/cm$^2$/sr)/(µW/cm$^2$) and 0.50±0.05×10$^8$ (p/s/cm$^2$/sr)/(µW/cm$^2$) for 24 hrs and 72 hrs time points respectively. These values returned to baseline 14 days (336 hr) post-injection. However, the whole body fluorescence intensity of PF-NPs decreased at much slower rate in the whole body. The body fluorescence was measured at 1.28±0.26×10$^8$ (p/s/cm$^2$/sr)/(µW/cm$^2$) 15 minutes post particles administration, and slowly decreased to $0.63\pm0.09\times10^8$ (p/s/cm$^2$/sr)/($\mu$W/cm$^2$) and $0.50\pm0.05\times10^8$ (p/s/cm$^2$/sr)/($\mu$W/cm$^2$) at 24 hrs and 72 hrs respectively.

The results indicate that SA-NPs undergo a fast initial elimination by excretion through the renal route followed by a slower elimination phase where the particles are cleared from the body within a time span of 14 days. Due to larger size and their highly cross-linked nature, the PF-NPs are not cleared by the renal route and are eliminated at substantially slower rate possibly via the hepatobiliary transport mechanism.

Real Time Pharmacokinetics of Nanoparticles in Tumor Tissue

The pharmacokinetic parameters for the nanoparticles in tumor were extracted from the data in FIG. 26B and summarized in FIG. 50. These parameters pertaining to the accumulation, retention, and elimination of nanoparticles in tumors are generally predictive of the therapeutic efficacy of nanoscale drug delivery systems. In general, the SA-NPs accumulated to a higher degree within tumors but cleared at a faster rate compared to that observed for PF-NPs. The peak fluorescence intensities in the tumor were measured to be $6.15\pm1.04\times10^8$ (p/s/cm$^2$/sr)/($\mu$W/cm$^2$) for SA-NPs and $0.15\pm0.25\times10^8$ (p/s/cm$^2$/sr)/($\mu$W/cm$^2$) for PF-NPs. The tumor AUC for SA-NPs was 3.5 fold larger than PF-NPs reflecting the more extensive accumulation of SA-NPs than PF-NPs in the tumor. The greater tumor accumulation of the SA-NPs is supported by their longer blood circulation and smaller size compared to the PF-NPs. However, PF-NPs exhibited a slower tumor clearance rate reflected by the large $t_{1/2}$ value of $277\pm33$ hrs and the smaller $k_{el}$ of $0.0025\pm0.0003$ hrs$^{-1}$, while the $t_{1/2}$ and $k_{el}$ for the SA-NPs were $92\pm12$ hrs and $0.0075\pm0.0006$ hrs$^{-1}$.

Blood Circulation and Organ Distribution of the Nanoparticles Determined by Ex Vivo Imaging Whole animal imaging was performed to determine tissue distribution of the nanoparticles (FIG. 27A). Tissue distribution and tumor accumulation were also evaluated from ex vivo NIR fluorescence analysis of collected blood and dissected tumors and organs, including liver, lung, kidney, spleen, skin, intestine and heart at various time points. The data are presented as the ratio of fluorescent intensity normalized to tissue average baseline values (FIG. 27B,C). SA-NPs were detected at higher concentrations and for longer time in the blood compared to the PF-NPs. Close to 30 minutes post injection, the blood fluorescent intensity ratio was measured to be $150.0\pm12.5$ and $70.0\pm6.0$ for SA-NPs and PF-NPs respectively. By 4 hours post-injection, these values reduced to $47\pm8$ and $4.1\pm0.5$ respectively. Based on these data, the blood circulation half-life of 63 minutes and 230 minutes for PF-NPs and SA-NPs were calculated. The PF-NPs exhibited substantially higher levels of accumulation in liver, spleen, lungs, heart, and intestine while significantly higher levels of SA-NPs could be detected in kidney and tumor. The high level of fluorescence in the intestines of mice treated with PF-NPs suggests that particles accumulating in the liver are excreted through feces. This elimination mode is generally slower than the elimination by urine. For this reason, fluorescence from the liver remains very strong over an extended period of time. These results are in good agreement with the whole body live animal imaging.

Microscopic Imaging of Tumor Tissue Demonstrated Extravasation of the Nanoparticles in the Tumor Tumor distribution of SA-NPs and PF-NPs at the microscopic level was examined using fluorescence microscopy. Tissue sections of vehicle-only (5% dextrose) infused tumors were imaged over FITC (excitation: 460-490 nm, emission 500-535 nm) emission window to determine the relative level of auto-fluorescence. As shown in FIG. 28, low levels of auto-fluorescence were observed in some regions of vehicle-treated tissues. Closer examination of the nature of this spectral emission demonstrated a broad wavelength distribution, in contrast to the more sharply defined emission peak of FITC-labeled nanoparticles. Such auto-fluorescence arises in tissues containing lipofucin, collagen, and extended pi orbital systems such as heme. Therefore in order to definitively distinguish auto-versus nanoparticle-mediated fluorescence within the FITC emission window, tissue sections were imaged over both FITC and TRITC (excitation 540-565 nm, emission 575-620 nm) emission windows. Merging of these results allowed clear delineation of auto-fluorescent (yellow green) versus nanoparticle (green) mediated fluorescence as shown in FIG. 28. As indicated in the figure, at 4 hours post-administration the SA-NPs accumulated to a greater extent in the mouse tumor tissue compared to that seen in PF-NPs and extravasated to a much greater extent from the tumor microvasculature into tumor-bearing tissues. In contrast, PF-NPs showed a more limited distribution within bulk tumor parenchyma. PF-NPs were predominantly confined to larger elements of the tumor vascular and associated perivascular regions.

Example 10. In Vivo MRI Studies

The ability of the Gd$^{+3}$-loaded PMAA-g-St-PS80 (PolyGd) and dox-loaded Gd$^{+3}$-loaded PMAA-g-St-PS80 (PolyGd-Dox) to produce positive contrast enhancement in different organs in vivo was compared to Omniscan® which is commercially available (FIG. 21). Major organs such as liver, spleen, heart, intestine, and bladder are represented in slice A, while slice B provides more details on the brain, aorta, and kidneys. At the clinical dose of 0.05 mmol/Kg Gd$^{+3}$, Omniscan® showed minimal contrast enhancement in the liver and cardiovascular system. It was rapidly extravasated from the vasculature and the contrast enhancement was poor even at 5 minutes post-injection. The formulation is cleared fast from the body through the renal route as evident by strong bladder signal. At half the Omniscan® dose (0.025 mmol/Kg Gd$^{+3}$), PMAA-g-St-P80 formulation produced significantly higher contrast in the liver, and cardiovascular system. There is a strong blood pool effect which lasts even after 60 minutes providing evidence for the longer blood circulation half-life of this formulation. The contrast agent appears to be eliminated by the renal route as evident by strong contrast enhancement observed in kidneys and then the urinary bladder. The bladder signal keeps increasing rapidly overtime providing evidence for the excretion of the polymer through the renal route. Having a formulation which would clear through the renal route is clinically preferable since this route of clearance is much faster than the hepatobiliary route.

Due to longer blood circulation of the PMAA-g-St-PS80 formulation, its superior contrast enhancement and blood pool effect, they could be used in a lower total amount of Gd$^{+3}$ and single dose instead of up to three injections to provide cardiac and whole body MRI scans for diagnosis and characterization of myocardial viability and atherosclerosis. In addition, with the high resolution and low dose needed to detect vasculature in detail, it is likely to provide early detection of pathogenic conditions in highly perfused organs such as the lung, liver, kidney and microhemorrhage in the brain.

$T_1$-weighted images provide only a qualitative reflection of contrast agent distribution, primarily because of the sensitivity profiles of the RF transmit and receiver coils. In contrast, $R_1$ maps provide a better quantitative measure of the contrast agent distribution in the whole body.

The temporal behaviour of the whole-body distribution of contrast agents was quantified by constructing $R_1$ maps at multiple time-points following injection without moving the animal (FIG. 27A). Organ-specific concentration profiles were then quantified directly from $R_1$ measurements in manually segmented regions-of-interest according to Equation 1 (described previously), (FIG. 27B,C).

The liver $R_1$ values increased from its baseline value of $1.0\pm0.1$ s$^{-1}$ to $2.1\pm0.3$ s$^{-1}$ ($\Delta R_1 \sim 1.1$ s$^{-1}$) by 60 minutes post-injection, and the kidneys $R_1$ increased from $0.6\pm0.1$ s$^{-1}$ to $1.4\pm0.3$ s$^{-1}$ ($\Delta R_1 \sim 0.8$ s$^{-1}$) by 5 minutes post injection. The bladder $R_1$ was measured at $0.4\pm0.1$ s$^{-1}$ at baseline, and increased sharply post contrast administration measuring at $1.1\pm0.1$ s$^{-1}$ ($\Delta R_1 \sim 0.7$ s$^{-1}$) and $2.3\pm0.4$ s$^{-1}$ ($\Delta R_1 \sim 1.9$) by 5 minutes and 60 minutes post injection respectively. By 300 minutes, there was a significant drop in the heart and kidney $R_1$ values while the liver and bladder $R_1$ values remained high. Similar trends were observed for PolyGd-Dox. The data were further validated by measuring the organ Gd$^{3+}$ content using inductively coupled plasma atomic emission spectrography (ICP-AES) (FIG. 29), and good agreement between the $R_1$ values and organ Gd$^{3+}$ contents were observed.

The $R_1$ of the left ventricular (LV) blood provides a useful indicator of vascular contrast agent enhancement in whole-body images. For Omniscan®, LV $R_1$ increased slightly from the baseline value of $0.7\pm0.2$ s$^{-1}$ to $0.8\pm0.1$ s$^{-1}$ ($\Delta R_1 \sim 0.1$ s$^{-1}$) by 2 minutes post injection. This increase was not statistically significant, and the LV $R_1$ values remained close to the baseline ($\sim 0.7$ s$^{-1}$) at all later time points. Following PolyGd injection, LV $R_1$ increased from its baseline value of $0.62\pm0.04$ s$^{-1}$ to $1.5\pm0.2$ s$^{-1}$ ($\Delta R_1 \sim 0.9$ s$^{-1}$) by 5 minutes post-injection and remained elevated at $1.0\pm0.1$ s$^{-1}$ even after 180 minutes.

Example 11. Brain Targeting Ability of the PMAA-g-St-PS80

It has been suggested that PS80 coating of certain nanoparticles leads to the enhanced adsorption of Apo-E from the blood to the particle surface (FIG. 30). Subsequently, the presence of Apo-E on the nanoparticle surface promotes internalization of these nanoparticles in the brain capillary endothelial cells via the LDL receptors expressed by these cells. A schematic of the uptake of St-g-PMAA-P80 into the microvessels via LDL receptors is shown in FIG. 30. TOF-SIMS is a highly sensitive, surface-specific technique enabling analysis of surface composition and chemistry. Sensitivity is on the order of ppm, whilst the surface-specificity is such that sampling is performed within the top 1-2 nm of the specimen i.e. only the top few atomic layers are sampled. TOF-SIMS clearly shows the presence of PS 80 on the surface of the nanoparticles as evidenced by the characteristic peaks at 255, 265, and 283 m/z in the negative ion mode. These peaks represent the series of oleic and stearic fatty acids and are side chains of the sorbitan molecule, and were absent in the control sample (no PS 80). Tof-sims data indicating polysorbate 80 expression on the surface of the St-g-PMAA-P80 nanoparticles are shown in FIG. 31.

To investigate the ability of the PMAA-g-St-PS80 to cross the blood-brain barrier, the MRI slices of the brain were taken. FIG. 32 shows the $R_1$ map of the different brain slices at baseline and 20 minutes after the polymer injection. Significant enhancement in brain blood vessels was observed. Also, there was significant increase in $r_1$ values in certain areas of the brain such as sagittal sinus, ventricles, cortex and Corpus Callosum. The major enhancement in the brain ventricles provides evidence for the presence of the polymer in the Cerebrospinal Fluid (CSF). Examination of the $R_1$ map of the different brain slices at pre- and post-injection of nanoparticles revealed enhancement in certain brain areas such as sagittal sinus, ventricles, and to a lesser extent in cortex and sub-cortical areas. At 30 minutes post injection the $R_1$ values were measured at $1.1\pm0.1$ s$^{-1}$, $1.1\pm0.1$ s$^{-1}$, $1.6\pm0.2$ s$^{-1}$, and $1.7\pm0.1$ s$^{-1}$ for cortex, sub-cortex, ventricles, and sagittal sinus respectively. These values decreased to $1\pm0.1$ s$^{-1}$, $0.9\pm0.1$ s$^{-1}$, $1.5\pm0.3$ s$^{-1}$, and $1.1\pm0.1$ s$^{-1}$ at 180 minutes post injection (FIG. 32C).

Example 12. Ex Vivo Studies

Ex vivo studies were conducted to further confirm the brain targeting ability of PMAA-g-St-PS80. The formulation was injected through tail vein and at certain time points the animals were sacrificed and the brain was taken out, washed, and assayed for the polymer content using a fluorescence technique, the blood content of the formulation was also measured (FIG. 22). The presence of the fluorescence in the brain at 24 hours when the blood fluorescence has returned to baseline indicates the brain deposition of the formulations at the organ level. Moreover, fluorescence microscopy in perfused brain slices post PMAA-g-St-PS80 administration was used to investigate the polymer deposition into the brain in the cellular level (FIG. 4). Our data confirm that the PMAA-g-St-PS80 nanoparticles extravasate from the brain capillary (passing through the endothelial tight junctions) and are deposited in the perivascular regions of the brain.

Fluorescence microscopic investigations of perfused brain tissues for formulation containing PS 80 and formulation with no PS80 were conducted. As shown in FIG. 4B, there was no polymer-related fluorescence detected in perfused brain samples receiving the PMAA-g-St (no PS 80) formulation (middle panel). The PMAA-PS 80-g-St samples on the other hand provide clear evidence of the localization of particle-associated fluorescence within microvessel endothelial cells as well as in the perivascular regions of the brain capillaries (far right panel). There was no evidence of uptake by the neurons at the time point studied here (45 minutes post-injection).

Example 13. The Tumor-Targeting Potential of PMAA-g-St-PS80

The tumor targeting ability of the linear polymer was investigated using a murine breast cancer tumor model (Balb/c mice bearing orthotopic murine EMT6 breast tumors). The tumor accumulation was investigated using both in vivo fluorescence imaging and MRI (FIG. 44). The polymer exhibited excellent tumor accumulation. Tumor volume was assessed at various time points post treatment.

Qualitative analysis of the MIP angiograms suggested a prolonged and constant visualization of arteries and veins after contrast medium administration (FIG. 36A). Quantitative analysis of individual $T_1$-weighted images verified a significant (P<0.05) rise in signal to noise ratio (SNR), defined as the ratio of the inferior vena cava signal intensity divided by the standard deviation of the signal intensity and contrast to noise ratio (CNR), defined as the difference between the inferior vena cava signal intensity and the signal intensity of the background soft tissue divided by the standard deviation of the signal intensity of noise, after the administration of the polymeric contrast agent, which remained elevated even 2 hrs post-injection (FIG. 36B).

FIG. 34A shows the $T_1$-weighted MR images and the corresponding $R_1$ maps of the Balb/c mice bearing EMT6WT breast carcinoma xenografts before and at multiple time points following injection of PolyGd and PolyGd-Dox at a dose of 0.025 mmol/kg $Gd^{3+}$. FIG. 34B displays temporal quantitative $R_1$ changes relative to baseline ($\Delta R_1$). A slow tumoral accumulation of the macromolecular contrast agent was observed, which was reflected by a gradual increase in $\Delta R_1$ to a peak of $0.66\pm0.13$ $s^{-1}$ (PolyGd) at 2 hours and $0.31\pm0.06$ $s^{-1}$ (PolyGd-Dox) at 3 hours and then sustained AR, elevation at $0.34\pm0.04$ $s^{-1}$ (PolyGd) and $0.13\pm0.02$ $s^{-1}$ (PolyGd-Dox) at 48 hours post injection in the tumor periphery. There was a statistically significant difference between the peak $\Delta R_1$ of PolyGd and PolyGd-Dox (p<0.05). The ability of the macromolecular contrast agents to accumulate in the tumor is consistent with the enhanced permeation and retention effect (EPR), reflecting the prolonged blood circulation of the PolyGd and PolyGd-Dox coupled with the leaky nature of the tumor vasculature, and poor tumor associated lymphatic drainage.

FIG. 35 shows anti-tumor activity of starch-based nanoparticles in EMT6/WT tumor-bearing mice. Tumor cells were implanted orthotopically on day zero and mice were then treated with (A) 5% dextrose (n=2×4), (B) free Dox (n=8), PF-NPs (n=2×4), (C) PF-NPs, or (D) SA-NPs (n=2×3) at a dose of 2×10 mg/kg equivalent to Dox on day 8 and 15. Tumor volume was measured up to day 62. Kaplan Meier survival curves for 5% dextrose, free Dox, PF-NPs, and SA-NPs were also prepared (FIG. 35E). The trend in survival curves was significantly different (p=0.0033, Mantel Cox) across the various treatments. Longitudinal recording of animal body weight was used as a general measure of animal viability, with losses of 20% of total initial body weight determined as a toxic limit requiring euthanasia. FIG. 35F shows the profiles of the body weight for mice before and after receipt of treatment administered in FIG. 2. In no instance did mice die or lose 20% of their body weight before tumors reached the cut-off size of 600 $mm^3$. All Dox groups showed some evidence of body weight loss over the first twenty days after the start of treatment. In general, treatment with free Dox, SA-NPs, and PF-NPs resulted in over 1 g (approximately 5%) body weight loss in only a few mice after 30 days of the start of treatment. No changes in eating, drinking, grooming, exploratory behavior, activity, or other physical features were noted in any of the treatment groups, suggesting a lack of general toxicity due to nanoparticles at the doses administered.

The tumor fluorescence signal remained relatively strong even after 4 days post injection (FIG. 44). Due to the high sensitivity of the fluorescence imaging, the tumor can be monitored for several days. The MRI is less sensitive but provides more details on the tumor morphology, structure, and polymer distribution within the tumor. Due to the PMAA-g-St-PS80 platform to accommodate both a near infrared fluorescence probe and a MRI contrast agent; the two techniques can be potentially combined to obtain more detail information on the tumor size (e.g., response to treatment), morphology, and polymer accumulation and distribution in tumor overtime.

Use of doxorubicin as part of the invention is disclosed in the foregoing examples. Other drugs or therapeutics can be loaded as cargo of nanoparticles of the invention. These include, for example, amifostine, apomine, arsenic trioxide, betulinic acid, bleomycin, bortezomib, bosentan, carmustine, celecoxib, cisplatin, cyclophosphamide, cytarabine, 4-S-cysteaminyl catechol, 4-S-cysteaminyl phenol, dacarbazine, docetaxel, everolimus, lenalidomide, paclitaxel, carboplatin, dacarbazine, fluorouracil, flutamide, imatinib mesylate, mercaptopurine, methotrexate, mitomycin, oxaliplatin, paclitaxel, prednisone, rituximab, sorafenib, tamoxifen, temozolomide, thalidomide, thioguanine, trastuzumab, valproic acid, vinblastine, vinblastine, etc.

The effectiveness of nanoparticles of the invention in crossing the blood brain barrier having been demonstrated, the invention includes use of nanoparticles of the invention to deliver therapeutics as loaded cargo of the nanoparticles for treatment of any of the following: a neurodegenerative disorder; a neuropsychiatric disorder; a CNS disorder selected from the group consisting of a brain tumor, epilepsy, migraine, narcolepsy, insomnia, chronic fatigue syndrome, mountain sickness, encephalitis, meningitis, and AIDS-related dementia; an angiogenesis-related disorder; an inflammatory or autoimmune disorder; age-related macular degeneration; or a lysosomal storage disease are within the scope of this invention. This is particularly true where the average size of the nanoparticles is about 100 nm or less.

Example 14. pH-Dependent Relaxivity and MR Contrast of PMAA-g-St-DTPA with Conjugated Gd Tumours are known to cause a decrease in local pH due to large production of lactic acid from metabolism. Here we demonstrate PMAA-g-St-DTPA-Gd nanoparticle could provide different relaxivity at different pH values suggesting their potential use in detection of pH deviations from normal physiological pH 7.4 in tumour tissue or infectious lesions by MR imaging (FIG. 50).

Example 15. Synthesis and Characterization of Poly(Diethylaminoethyl Methacrylate)-Grafted Starch (PDEAEM-g-St) and PDEAEM-g-St-DTPA Nanoparticles A free-radical dispersion polymerization method was used to prepare the particles. The polymerizations was conducted under nitrogen using α,α'-azodiisobutyramidine dihydro-chloride (V-50) as the initiator, ethylene glycol dimethacrylate (EGDM) as the cross-linker for preformed nanoparticles, and polyvinylprolidone (PVP) as the non-ionic stabilizer. The polymerization was carried out for 6 hours at 70° C. using a water-ethanol mixture (9:1). The resulting particles were washed and purified using water and ethanol. The linear polymers of PDEAEM-g-St were also prepared using the same synthesis method without the use of a cross-linker.

The grafting of PDEAEM onto starch is confirmed with FTIR and $^1$H NMR spectroscopy. TEM is used to investigate the morphology of the particles. DLS is used to study the effect of pH and particle composition on size. Titration studies will be used to gain insight into the DEAEM contents, and also the $pK_a$ of the grafted copolymer.

To synthesize PDEAEM-g-St-DTPA nanoparticles, 2 g of dried starch-DTPA was added to 40 mL of deionized water in a cleaned two-mouthed reaction flask and was left to stir until homogenous. The pH of the solution was adjusted to approximately 8 using 0.1N NaOH solution, and was filled with water to make up a total volume of 95 mL. The solution was placed in a heated water jacket on a stir plate, and was left to heat and stir at 70° C. while purging with nitrogen gas for 15 minutes. The initiator, V-50, was then added to the reaction flask. In a separate scintillation vial, 0.2 g PVP and water were mixed with or without 0.3-0.5 g of Tween 80 and placed on a vortex apparatus until homogenous, and were then added to the reaction flask. In another scintillation vial, 2.0 g of the monomer, DEAEM; 754 of the crosslinker, EGDM; 5 mL ethanol and 5 mL deionized water were added together and placed on a vortex apparatus until homogenous. They were then added into the reaction flask. The reaction system was then sealed with film with loose venting, and was left under 70° C. for 8 hours thereafter, where it was also left stirring overnight. Nitrogen purge was removed from the dispersion and instead aerated the vessel. The dispersion was then transferred to a 12,000-14,000 MWCO Spectra/Pore Dialysis Membrane and was left to dialyze in filtered water for 24 hours, with the media being refreshed every 2 hours, minimum 3 times. The washed sample was then dried in light heat for another 24 hours or until crystals had formed. PDEAEM-g-St-DTPA nanoparticles and linear polymers can also be prepared by conjugating DTPA onto PDEAEM-g-St.

Stable PDEAEM-g-St latexes with solid contents of up to 4.5% were successfully prepared using the described method. The dispersion polymerization method used is fairly straight forward and does not require the use of oils and organic solvents making this method advantageous over reverse microemulsion polymerization methods. Initially, all the monomers are soluble in water, and as the polymerization progresses the formed grafted polymer becomes insoluble at high pH and precipitate outs in form of particles, subsequently, these particles are stabilized with the aid of surfactants. FIG. 51 summarizes the feed composition of four different batches. The grafting yield was dependent on the DEAEM concentration. Increasing the DEAEM concentration was accompanied by increase in the grafting yield. This could be explained in terms of greater availability of monomer molecules in the proximity of starch at higher DEAEM concentrations. The starch macroradicals are relatively immobile. As a result, the reaction of these macromolecules with monomers would essentially depend on the availability of DEAEM monomers on the starch vicinity.

All nanoparticles analyzed presented a very homogeneous morphology with relatively uniform particle size distribution and a rather spherical shape. The nanoparticles have a smooth surface morphology. There is slight degree of particle aggregation and fusion present; however, this might be due to nature of TEM sample preparation.

Conformation of Grafting by FTIR and $^1$H NMR

The FTIR spectra of starch, PDEAEM and PDEAEM-g-St are shown in FIG. 37. In comparison with the spectrum of the native starch, the major change is the presence of a carbonyl C=O absorption frequency at 1724 cm$^{-1}$ and stretch vibration of tertiary amine groups at 2962-2964 cm$^{-1}$. The peaks at 1166, 1090, 1020, and 954 cm$^{-1}$ in native starch are due to the CO bond stretching. The peaks at 1090 and 1020 cm$^{-1}$ are characteristic of the anhydroglucose ring CO/CC stretching. A characteristic peak occurred at 1645 cm$^{-1}$ is due to the presence of bound water in starch. A broadband due to hydrogen bonded hydroxyl group (O—H) appeared at 3450 cm$^{-1}$ and is attributed to the complex vibrational stretching, associated with free, inter and intra molecular bound hydroxyl groups. The OH stretching band at 3450 cm$^{-1}$ is absent in the PDEAEM homopolymer. The band at 2,916-2920 cm$^{-1}$ is characteristic of C—H stretching. The strong OH stretching band at 3450 cm$^{-1}$ in the native starch decreased in intensity following the grafting reaction implying the reaction of starch with DEAEM through starch OH groups. Also, the grafted polymer exhibited characteristics peaks of pyranose ring vibrations at 520-920 cm$^{-1}$ which was absent in PDEAEM homopolymer proving the grafting of PDEAEM onto starch.

FIG. 38 shows the $^1$H-NMR spectra of a) soluble starch, c) PDEAEM, and d) PDEAEM-g-St. The starch spectrum exhibits characteristic peaks at 3.51 ppm, which was attributed to CH$_2$ of starch units liked to C6 carbons. The peak at 3.82 ppm is attributed to the hydrogens linked to the CH units joined to C1-C5 carbons. The peak at 5.24 ppm is attributed to the hydrogens of the R—OH hydroxyl groups. The NMR spectrum of PDEAEM-g-St polymer shows peaks characteristics of both starch and PDEAEM. There is a small shift in peaks at 3.34, 3.59, and 5.24 as well as a slight change of shape in peak at 3.82 ppm due to alteration of chemical environment brought on by grafting. Also, there is reduction in relative intensity of the peak at 5.43 indicating that the starch hydroxyl groups are participating in the grafting reaction.

Effect of pH and Starch Content on Particle Size

Dynamic light scattering was used to determine the size of the nanoparticles with various starch:DEAEM ratios in buffers of different pH and constant ionic strength. Typical dynamic laser light scattering data showing the intensity weight distribution of PDEAEM-g-St particles in PBS of pH 4 and 7.4 are shown in FIGS. 39 and 40. The particles were monodispersed and followed a Gaussian distribution. The results in FIG. 41 demonstrate that the particle size changes as the function of pH and starch content. The PDEAEM nanoparticles had an average mean diameter of 521 nm at pH 4. The size decreased to 221.8 nm at pH 7.4 due to the deprotonation of the tertiary amine groups associated with the nanoparticles. This change in average diameter translates into 913-fold change in volume with pH. It was observed that grafting actually decreased the particle size by more than two folds in some cases. The nanoparticles with 1:1.4 molar ratio of DEAEM and starch had an average diameter of 250 nm at low pH, and shrank to 129 nm at pH of 7.4. In general, the increase in starch content resulted in reduction in pH sensitivity. However, particles containing starch appeared to have a sharper phase transition compared near the physiological pH range compared to PDEAEM nanoparticles.

pH-Dependent Particle Size of PDEAEM-g-St-DTPA with Loaded Gd

In a typical polymerization, the following recipe was used and Gd$^{3+}$ was conjugated on to the PMAA-g-St-DTPA-PS80 nanoparticles using the methods described above. The particle size in buffer solutions of various pH was measured by DLS. The result in the FIG. 42 shows particle diameter increasing as pH decreases. When the particle volume increases, the particle hydration increases, which may generate higher relaxivity under MR and thus has the potential to image pH difference between the tumor or infectious lesion and healthy tissue. Recipe: maltodextrin-DTPA (1.4 g); water (163.5 mL); NaOH added (to adjust pH, (23.5 mL to pH 8.0)); ethanol (5 mL); V-50 (0.2 g); PVP (0.2 g); Tween 80 (0.5 g); DEAEM (1.8 g); and EGDM (65 µL).

Example 16. Delivery of Doxorubicin to Brain Tumor

A majority of therapeutic agents, including chemotherapeutic drugs (e.g. doxorubicin) and monoclonal antibodies, cannot cross the BBB and thus fail to provide effective therapy of brain tumors. As one of examples of delivery of therapeutic agents to brain tumors, brain metastasis of breast cancer was used. Ten thousand of MDA-MB231-luc 3N2 cells were injected intracranially.

FIG. 33A presents representative images of brain tumor acquired by bioluminescence imaging (left) and distribution of FH750-labeled nanoparticles (right) injected one week post-intracranial inoculation of the tumor. The results strongly suggest the accumulation of the nanoparticles in the brain tumor. The images were acquired 6 hours after tail vein injection of the nanoparticles. The fixed and sliced brain tumor tissue was examined by fluorescence microscopy using an AMG EVOSfl fluorescence microscope (Advanced Microscopy Group, Bothell, Wash.) and the images were acquired using a DAPI and RFP filter set to visualize the Hoescht33342 and NIR HF 750-labeled nanoparticles. FIG. 33B shows clearly the nanoparticles and Dox released from the nanoparticles.

Use of doxorubicin as part of the invention is disclosed in the foregoing examples. Other drugs or therapeutics can be loaded as cargo of nanoparticles of the invention. These include, for example, amifostine, apomine, arsenic trioxide, betulinic acid, bleomycin, bortezomib, bosentan, carmustine, celecoxib, cisplatin, cyclophosphamide, cytarabine, 4-S-cysteaminyl catechol, 4-S-cysteaminyl phenol, dacarbazine, docetaxel, everolimus, lenalidomide, paclitaxel, carboplatin, dacarbazine, fluorouracil, flutamide, imatinib mesylate, mercaptopurine, methotrexate, mitomycin, oxaliplatin, paclitaxel, prednisone, rituximab, sorafenib, tamoxifen, temozolomide, thalidomide, thioguanine, trastuzumab, valproic acid, vinblastine, vinblastine, etc.

The effectiveness of nanoparticles of the invention in crossing the blood-brain barrier having been demonstrated, the invention includes use of nanoparticles of the invention to deliver therapeutics as loaded cargo of the nanoparticles for treatment of any of the following: a neurodegenerative disorder; a neuropsychiatric disorder; a CNS disorder selected from the group consisting of a brain tumor, epilepsy, migraine, narcolepsy, insomnia, chronic fatigue syndrome, mountain sickness, encephalitis, meningitis, and AIDS-related dementia; an angiogenesis-related disorder; an inflammatory or autoimmune disorder; age-related macular degeneration; or a lysosomal storage disease are within the scope of this invention. This is particularly true where the average size of the nanoparticles is about 100 nm or less.

It will be understood that recitations of numerical ranges by endpoints include all numbers subsumed within that range. Also, a recited range having an endpoint within a different recited range is a disclosure of any other range having endpoints of those recited ranges. For example, recitation of the ranges 20 to 350 and 10 to 300 is a disclosure of the ranges 20 to 300 and 10 to 350.

The contents of all documents referred to herein, and also the contents of U.S. Provisional Patent Application No. 61/605,995 to which this application claims priority, are incorporated herein by reference.

REFERENCES

1. Kerr, R. W., *Chemistry and industry of starch*. Chemistry and industry of starch, 1950 (Ed. 2).
2. Ellis, H. and S. Ring, *A study of some factors influencing amylose gelation*. Carbohydr. Polym., 1985. 5(3): p. 201-213.
3. Cui, S. W., *Food carbohydrates: chemistry, physical properties, and applications*. 2005, New York: Taylor & Francis.
4. Shalviri, A., Q. Liu, M. J. Abdekhodaie, and X. Y. Wu, *Novel modified starch-xanthan gum hydrogels for controlled drug delivery: Synthesis and characterization*. Carbohydr. Polym., 2010. 79(4): p. 898-907.
5. Celik, M. and M. Sacak, *Synthesis and characterization of starch poly (methyl methacrylate) graft copolymers*. J. Appl. Polym. Sci., 2002. 86(1): p. 53-57.
6. Beliakova, M. K., A. A. Aly, and F. A. Abdel Mohdy, *Grafting of poly (methacrylic acid) on starch and poly (vinyl alcohol)*. Starch Stärke, 2004. 56(9): p. 407-412.
7. Hebeish, A., M. Beliakova, and A. Bayazeed, *Improved synthesis of poly (MAA)-starch graft copolymers*. J. Appl. Polym. Sci., 1998. 68(10): p. 1709-1715.
8. Liu, M., R. Cheng, J. Wu, and C. Ma, *Graft copolymerization of methyl acrylate onto potato starch initiated by ceric ammonium nitrate*. J. Polym. Sci., Part A: Polym. Chem., 1993. 31(13): p. 3181-3186.
9. Mino, G. and S. Kaizerman, *A new method for the preparation of graft copolymers. Polymerization initiated by ceric ion redox systems*. J. Polym. Sci., 1958. 31(122): p. 242-243.
10. Sangramsingh, N., B. Patra, B. Singh, and C. Patra, *Graft copolymerization of methyl methacrylate onto starch using a Ce (IV)-glucose initiator system*. J. Appl. Polym. Sci., 2004. 91(2): p. 981-990.
11. Trimnell, D. and E. Stout, *Grafting acrylic acid onto starch and poly (vinyl alcohol) by photolysis*. J. Appl. Polym. Sci., 1980. 25(10): p. 2431-2434.
12. Zhang, L. M. and D. Q. Chen, *Grafting of 2 (Dimethylamino) ethyl Methacrylate onto Potato Starch Using Potassium Permanganate/Sulfuric Acid Initiation System*. Starch Stärke, 2001. 53(7): p. 311-316.
13. Chan, W. C. and C. Y. Chiang, *Flocculation of clay suspensions with water insoluble starch grafting acrylamide/sodium allylsulfonated copolymer powder*. Journal of Applied Polymer Science, 1995. 58(10): p. 1721-1726.
14. Elvira, C., J. Mano, J. San Roman, and R. Reis, *Starch-based biodegradable hydrogels with potential biomedical applications as drug delivery systems*. Biomaterials, 2002. 23(9): p. 1955-1966.
15. Khalil, M., S. Farag, and S. Fattach, *Hydrolysis of poly (acrylamide)-starch graft copolymer*. Journal of Applied Polymer Science, 1995. 57(3): p. 335-342.
16. Rath, S. and R. Singh, *Flocculation characteristics of grafted and ungrafted starch, amylose, and amylopectin*. Journal of Applied Polymer Science, 1997. 66(9): p. 1721-1729.
17. Shah, S., B. Patel, C. Patel, and H. Trivedi, *Saponification of graft copolymers of sodium salt of partially carboxymethylated amylose and its water absorbency*. Starch Stärke, 1992. 44(3): p. 108-110.
18. Singh, R. P., G. Karmakar, S. Rath, N. Karmakar, S. Pandey, T. Tripathy, J. Panda, K. Kanan, S. Jain, and N. Lan, *Biodegradable drag reducing agents and flocculants based on polysaccharides: materials and applications*. Polymer Engineering & Science, 2000. 40(1): p. 46-60.
19. Aoki, T., M. Kawashima, H. Katono, K. Sanui, N. Ogata, T. Okano, and Y. Sakurai, *Temperature-responsive interpenetrating polymer networks constructed with poly (acrylic acid) and poly (N,N-dimethylacrylamide)*. Macromolecules, 1994. 27(4): p. 947-952.
20. Bearinger, J., D. Castner, and K. Healy, *Biomolecular modification of p (AAm-co-EG/AA) IPNs supports osteoblast adhesion and phenotypic expression*. J. Biomater. Sci., Polym. Ed., 1998. 9(7): p. 629-652.
21. Vernon, B., S. W. Kim, and Y. H. Bae, *Insulin release from islets of Langerhans entrapped in a poly(N-isopro-* pylacrylamide-co-acrylic acid) polymer gel. J Biomater Sci Polym Ed, 1999. 10(2): p. 183-98.
22. Bayazeed, A., M. Elzairy, and A. Hebeish, *Synthesis and Application of New Thickerners Part 1: Preparation of Poly (Acrylic Acid) Starch Graft Copolymer*. Starch Stärke, 1989. 41(6): p. 233-236.
23. Hirose, Y., T. Amiya, Y. Hirokawa, and T. Tanaka, *Phase transition of submicron gel beads*. Macromolecules, 1987. 20(6): p. 1342-1344.
24. Saboktakin, M. R., A. Maharramov, and M. A. Ramazanov, *pH-sensitive starch hydrogels via free radical graft copolymerization, synthesis and properties*. Carbohydr. Polym., 2009. 77(3): p. 634-638.
25. Wiersema, P., A. Loeb, and J. T. G. Overbeek, *Calculation of the electrophoretic mobility of a spherical colloid particle*. J. Colloid Interface Sci., 1966. 22(1): p. 78-99.
26. Kawaguchi, S., Y. Nishikawa, T. Kitano, K. Ito, and A. Minakata, *Dissociation behavior of poly (itaconic acid) by potentiometric titration and intrinsic viscosity*. Macromolecules, 1990. 23(10): p. 2710-2714.
27. Kitano, T., S. Kawaguchi, K. Ito, and A. Minakata, *Dissociation behavior of poly (fumaric acid) and poly (maleic acid). 1. Potentiometric titration and intrinsic viscosity*. Macromolecules, 1987. 20(7): p. 1598-1606.
28. Wu, X. Y., Q. Zhang, and R. Arshady, *Stimuli sensetive hydrogels: response and release modulation, in Introduction to polymeric biomaterials*, R. Arshady, Editor. 2004, Citus Books: London.
29. Zeman, L. and D. Patterson, *Pressure effects in polymer solution phase equilibriums. II. Systems showing upper and low critical solution temperatures*. J. Phys. Chem., 1972. 76(8): p. 1214-1219.
30. Aggarwal, A., R. Saxena, B. Wang, and G. T. Caneba, *Studies of the polymerization of methacrylic acid via free-radical retrograde precipitation polymerization process*. J. Appl. Polym. Sci., 1996. 62(12): p. 2039-2051.
31. Donbrow, M., E. Azaz, and A. Pillersdorf, *Autoxidation of polysorbates*. J. Pharm. Sci., 1978. 67(12): p. 1676-1681.
32. Ha, E., W. Wang, and Y. J. Wang, *Peroxide formation in polysorbate 80 and protein stability*. J. Pharm. Sci., 2002. 91(10): p. 2252-2264.
33. Donbrow, M., *Nonionic surfactants: physical chemistry*. 1987, New York: Marcel Dekker.
34. Nema, S., R. Washkuhn, and R. Brendel, *Excipients and their use in injectable products*. J. Pharm. Sci. Technol., 1997. 51(4): p. 166.
35. Ghosh, P., S. C. Chadha, A. R. Mukherjee, and S. R. Palit, *Endgroup studies in persulfate initiated vinyl polymer by dye techniques. Part I. Initiation by persulfate alone*. Journal of Polymer Science Part A: General Papers, 1964. 2(10): p. 4433-4440.
36. Hohenstein, W. and H. Mark, *Polymerization of olefins and diolefins in suspension and emulsion. Part II*. Journal of Polymer Science, 1946. 1(6): p. 549-580.
37. Tauer, K., A. M. I. Ali, and M. Sedlak, *On the preparation of stable poly (2-hydroxyethyl methacrylate) nanoparticles*. Colloid Polym. Sci., 2005. 283(4): p. 351-358.
38. Maeda, H., J. Wu, T. Sawa, Y. Matsumura, and K. Hori, *Tumor vascular permeability and the EPR effect in macromolecular therapeutics: a review*. J Controlled Release, 2000. 65(1-2): p. 271-284.
39. Wu, X. Y. and P. I. Lee, *Preparation and characterization of thermal-and pH-sensitive nanospheres*. Pharm. Res., 1993. 10(10): p. 1544-1547.
40. Hoare, T. and R. Pelton, *Functional group distributions in carboxylic acid containing poly (N-isopropylacrylamide) microgels*. Langmuir, 2004. 20(6): p. 2123-2133.
41. Kawaguchi, S., A. Yekta, and M. A. Winnik, *Surface characterization and dissociation properties of carboxylic acid core-shell latex particle by potentiometric and conductometric titration*. J Colloid Interface Sci, 1995. 176(2): p. 362-369.
42. Bouma, J., J. H. Beijnen, A. Bult, and W. J. M. Underberg, *Anthracycline antitumour agents*. Pharm. World Sci., 1986. 8(2): p. 109-133.
43. *Adriamycin monograph, in Compendium of pharmaceuticals and specialities*, L. Welbanks, Editor. 2000, Canadian pharmacists association: Ottawa, ON. p. 31-32.
44. Álvarez, R. H., *Present and future evolution of advanced breast cancer therapy*. Breast Cancer Res, 2010. 12(Suppl 2): p. 51.
45. Teraoka, K., M. Hirano, K. Yamaguchi, and A. Yamashina, *Progressive cardiac dysfunction in adriamycin-induced cardiomyopathy rats*. Eur. J. Heart Failure, 2000. 2(4): p. 373-378.
46. Yeh, E. T. H., A. T. Tong, D. J. Lenihan, S. W. Yusuf, J. Swafford, C. Champion, J.-B. Durand, H. Gibbs, A. A. Zafarmand, and M. S. Ewer, *Cardiovascular Complications of Cancer Therapy*. Circulation, 2004. 109(25): p. 3122-3131.
47. Arceci, R. J., *Can multidrug resistance mechanisms be modified?* Br J Haematol., 2000. 110(2): p. 285-291.
48. Higgins, C. F., *Multiple molecular mechanisms for multidrug resistance transporters*. Nature, 2007. 446 (7137): p. 749-757.
49. Wong, H. L., X. Y. Wu, and R. Bendayan, *Multidrug resistance in solid tumors and its reversal., in Pharmaceutical perspectives of cancer therapeutics*, Y. LU and R. I. Mahato, Editors. 2007, Springer: New York, N.Y. p. 121-148.
50. Glavinas, H., P. Krajcsi, J. Cserepes, and B. Sarkadi, *The role of ABC transporters in drug resistance, metabolism and toxicity*. Curr. Drug Delivery, 2004. 1(1): p. 27-42.
51. Bennis, S., C. Chapey, J. Robert, and P. Couvreur, *Enhanced cytotoxicity of doxorubicin encapsulated in polyisohexylcyanoacrylate nanospheres against multidrug-resistant tumour cells in culture*. Eur. J. Cancer, 1994. 30(1): p. 89-93.
52. Couvreur, P., L. Grislain, V. Lenaerts, F. Brasseur, P. Guiot, and A. Biernacki, *Biodegradable polymeric nanoparticles as drug carrier for antitumor agents, in Polymeric Nanoparticles and Microspheres*, P. Guiot and P. Couvreur, Editors. 1986, CRC Press: Boca Raton, Fla. p. 27-93.
53. Shuhendler, A. J., R. Y. Cheung, J. Manias, A. Connor, A. M. Rauth, and X. Y. Wu, *A novel doxorubicin-mitomycin C co-encapsulated nanoparticle formulation exhibits anti-cancer synergy in multidrug resistant human breast cancer cells*. Breast Cancer Res Treat., 2010. 119(2): p. 255-269.
54. Prasad, P., J. Cheng, A. Shuhendler, A. M. Rauth, and X. Y. Wu, *A novel nanoparticle formulation overcomes multiple types of membrane efflux pumps in human breast cancer cells*. Drug Delivery Transl Res., 2012. 2(2): p. 1-11.
55. Wong, H. L., A. M. Rauth, R. Bendayan, J. L. Manias, M. Ramaswamy, Z. Liu, S. Z. Erhan, and X. Y. Wu, *A new polymer-lipid hybrid nanoparticle system increases cytotoxicity of doxorubicin against multidrug-resistant human breast cancer cells*. Pharm. Res., 2006. 23(7): p. 1574-1585.

56. Torchilin, V. P., *Passive and active drug targeting: drug delivery to tumors as an example*, in *Handb Exp Pharmacol.*, M. schafer-korting, Editor. 2010, Springer: New York, N.Y. p. 3-53.
57. Maeda, H., *The enhanced permeability and retention (EPR) effect in tumor vasculature: the key role of tumor-selective macromolecular drug targeting*. Adv Enzyme Regul, 2001. 41(1): p. 189-207.
58. Brigger, I., C. Dubernet, and P. Couvreur, *Nanoparticles in cancer therapy and diagnosis*. Adv Drug Delivery Rev, 2002. 54(5): p. 631-651.
59. Panyam, J. and V. Labhasetwar, *Biodegradable nanoparticles for drug and gene delivery to cells and tissue*. Adv Drug Delivery Rev, 2003. 55(3): p. 329-347.
60. Abbott, N. J. and I. A. Romero, *Transporting therapeutics across the blood-brain barrier*. Mol. Med. Today, 1996. 2(3): p. 106-113.
61. Chauhan, N. B., *Trafficking of intracerebroventricularly injected antisense oligonucleotides in the mouse brain*. Antisense Nucleic Acid Drug Dev., 2002. 12(5): p. 353-357.
62. Neuwelt, E., K. Maravilla, E. Frenkel, S. Rapaport, S. Hill, and P. Barnett, *Osmotic blood-brain barrier disruption. Computerized tomographic monitoring of chemotherapeutic agent delivery*. J. Clin. Invest., 1979. 64(2): p. 684-688.
63. Wohlfart, S., S. Gelperina, and J. Kreuter, *Transport of drugs across the blood-brain barrier by nanoparticles*. J. Controlled Release, 2011. 161(2): p. 264-273.
64. Alyautdin, R. N., V. E. Petrov, K. Langer, A. Berthold, D. A. Kharkevich, and J. Kreuter, *Delivery of loperamide across the blood-brain barrier with polysorbate 80-coated polybutylcyanoacrylate nanoparticles*. Pharm. Res., 1997. 14(3): p. 325-328.
65. Kreuter, J., T. Hekmatara, S. Dreis, T. Vogel, S. Gelperina, and K. Langer, *Covalent attachment of apolipoprotein AI and apolipoprotein 8-100 to albumin nanoparticles enables drug transport into the brain*. J. Controlled Release, 2007. 118(1): p. 54-58.
66. Tosi, G., L. Costantino, F. Rivasi, B. Ruozi, E. Leo, A. Vergoni, R. Tacchi, A. Bertolini, M. Vandelli, and F. Forni, *Targeting the central nervous system: in vivo experiments with peptide-derivatized nanoparticles loaded with Loperamide and Rhodamine-123*. J. Controlled Release, 2007. 122(1): p. 1-9.
67. Kurakhmaeva, K. B., I. A. Djindjikhashvili, V. E. Petrov, V. U. Balabanyan, T. A. Voronina, S. S. Trofimov, J. Kreuter, S. Gelperina, D. Begley, and R. N. Alyautdin, *Brain targeting of nerve growth factor using poly (butyl cyanoacrylate) nanoparticles*. J. Drug Targeting, 2009. 17(8): p. 564-574.
68. Zensi, A., D. Begley, C. Pontikis, C. Legros, L. Mihoreanu, S. Wagner, C. Büchel, H. von Briesen, and J. Kreuter, *Albumin nanoparticles targeted with Apo E enter the CNS by transcytosis and are delivered to neurones*. J. of Controlled Release, 2009. 137(1): p. 78-86.
69. Michaelis, K., M. M. Hoffmann, S. Dreis, E. Herbert, R. N. Alyautdin, M. Michaelis, J. Kreuter, and K. Langer, *Covalent linkage of apolipoprotein E to albumin nanoparticles strongly enhances drug transport into the brain*. J. Pharmacol. Exp. Ther., 2006. 317(3): p. 1246-1253.
70. Lauterbur, P. C., *Image formation by induced local interactions: examples employing nuclear magnetic resonance*. Nature, 1973. 242(5394): p. 190-191.
71. Yan, G. P., L. Robinson, and P. Hogg, *Magnetic resonance imaging contrast agents: overview and perspectives*. Radiography, 2007. 13(suppl 1): p. e5-e19.
72. Lauffer, R. B., *Paramagnetic metal complexes as water proton relaxation agents for NMR imaging: theory and design*. Chem. Rev., 1987. 87(5): p. 901-927.
73. Aime, S., M. Fasano, and E. Terreno, *Lanthanide (III) chelates for NMR biomedical applications*. Chem. Soc. Rev., 1998. 27(1): p. 19-29.
74. Caravan, P., J. J. Ellison, T. J. McMurry, and R. B. Lauffer, *Gadolinium (III) chelates as MRI contrast agents: structure, dynamics, and applications*. Chem. Rev., 1999. 99(9): p. 2293-2352.
75. Weinmann, H. J., R. C. Brasch, W. R. Press, and G. E. Wesbey, *Characteristics of gadolinium-DTPA complex: a potential NMR contrast agent*. Am. J. Roentgenol., 1984. 142(3): p. 619-624.
76. Haley, T., K. Raymond, N. Komesu, and H. Upham, *Toxicological and pharmacological effects of gadolinium and samarium chlorides*. Br. J. Pharmacol. Chemother., 1961. 17(3): p. 526-532.
77. Spencer, A. J., S. A. Wilson, J. Batchelor, A. Reid, J. Pees, and E. Harpur, *Gadolinium chloride toxicity in the rat*. Toxicol. Pathol., 1997. 25(3): p. 245-255.
78. Graca, J., F. Davison, and J. Feavel, *Comparative toxicity of stable rare earth compounds. III. Acute toxicity of intravenous injections of chlorides and chelates in dogs*. AMA Arch. Ind. Health, 1964. 8: p. 555-564.
79. Lu, Z. R., A. M. Mohs, Y. Zong, and Y. Feng, *Polydisulfide Gd (III) chelates as biodegradable macromolecular magnetic resonance imaging contrast agents*. Int. J. Nanomed., 2006. 1(1): p. 31-40.
80. Bogdanov Jr, A., S. Wright, E. Marecos, A. Bogdanova, C. Martin, P. Petherick, and R. Weissleder, *A long-circulating co-polymer in "passive targeting" to solid tumors*. J. Drug Targeting, 1997. 4(5): p. 321-330.
81. Cai, J., E. M. Shapiro, and A. D. Hamilton, *Self-assembling DNA quadruplex conjugated to MRI contrast agents*. Bioconjugate Chem., 2009. 20(2): p. 205-208.
82. Doble, D. M. J., M. Botta, J. Wang, S. Aime, A. Barge, and K. N. Raymond, *Optimization of the relaxivity of MRI contrast agents: Effect of poly (ethylene glycol) chains on the water-exchange rates of Gd III complexes*. J. Am. Chem. Soc., 2001. 123(43): p. 10758-10759.
83. Kobayashi, H., S. Kawamoto, S. K. Jo, H. L. Bryant Jr, M. W. Brechbiel, and A. Robert, *Macromolecular MRI contrast agents with small dendrimers: pharmacokinetic differences between sizes and cores*. Bioconjugate Chem., 2003. 14(2): p. 388-394.
84. Langereis, S., Q. G. De Lussanet, M. H. P. Van Genderen, W. H. Backes, and E. Meijer, *Multivalent contrast agents based on gadolinium-diethylenetriaminepentaacetic acid-terminated poly (propylene imine) dendrimers for magnetic resonance imaging*. Macromolecules, 2004. 37(9): p. 3084-3091.
85. Mulder, W. J. M., G. J. Strijkers, A. W. Griffioen, L. van Bloois, G. Molema, G. Storm, G. A. Koning, and K. Nicolay, *A liposomal system for contrast-enhanced magnetic resonance imaging of molecular targets*. Bioconjugate Chem., 2004. 15(4): p. 799-806.
86. Rebizak, R., M. Schaefer, and E. Dellacherie, *Polymeric conjugates of $Gd^{3+}$-diethylenetriaminepentaacetic acid and dextran. 1. Synthesis, characterization, and paramagnetic properties*. Bioconjugate Chem., 1997. 8(4): p. 605-610.
87. Steve, R., M. O. Guler, R. E. Bras, T. J. Meade, and S. I. Stupp, *Self-assembled peptide amphiphile nanofibers conjugated to MRI contrast agents*. Nano Lett., 2005. 5(1): p. 1-4.

88. Vexler, V. S., O. Clément, H. Schmitt Willich, and R. C. Brasch, *Effect of varying the molecular weight of the MR contrast agent Gd-DTPA-polylysine on blood pharmacokinetics and enhancement patterns.* J Magn Reson Imaging, 1994. 4(3): p. 381-388.
89. Wen, X., E. F. Jackson, R. E. Price, E. E. Kim, Q. Wu, S. Wallace, C. Charnsangavej, J. G. Gelovani, and C. Li, *Synthesis and characterization of poly (L-glutamic acid) gadolinium chelate: a new biodegradable MRI contrast agent.* Bioconjugate Chem., 2004. 15(6): p. 1408-1415.
90. Zhang, G., R. Zhang, X. Wen, L. Li, and C. Li, *Micelles based on biodegradable poly (l-glutamic acid)-b-polylactide with paramagnetic Gd ions chelated to the shell layer as a potential nanoscale MRI-visible delivery system.* Biomacromolecules, 2007. 9(1): p. 36-42.
91. Maeda, H., J. Wu, T. Sawa, Y. Matsumura, and K. Hori, *Tumor vascular permeability and the EPR effect in macromolecular therapeutics: a review.* Journal of Controlled Release, 2000. 65(1-2): p. 271-284.
92. Peters, T., *The plasma proteins.* 1975, New York: Academic Press.
93. Alhareth, K., C. Vauthier, C. Gueutin, G. Ponchel, and F. Moussa, *Doxorubicin loading and in vitro release from poly(alkylcyanoacrylate) nanoparticles produced by redox radical emulsion polymerization.* Journal of Applied Polymer Science, 2011. 119(2): p. 816-822.
94. Park, J., P. M. Fong, J. Lu, K. S. Russell, C. J. Booth, W. M. Saltzman, and T. M. Fahmy, *PEGylated PLGA nanoparticles for the improved delivery of doxorubicin.* Nanomedicine: Nanotechnology, Biology and Medicine, 2009. 5(4): p. 410-418.
95. Hara, H., R. M. Friedlander, V. Gagliardini, C. Ayata, K. Fink, Z. Huang, M. Shimizu-Sasamata, J. Yuan, and M. A. Moskowitz, *Inhibition of interleukin 1β converting enzyme family proteases reduces ischemic and excitotoxic neuronal damage.* Proceedings of the National Academy of Sciences, 1997. 94(5): p. 2007-2012.
96. Thornberry, N. A. and Y. Lazebnik, *Caspases: enemies within.* Science, 1998. 281(5381): p. 1312-1316.
97. Robertson, G. S., S. J. Crocker, D. W. Nicholson, and J. B. Schulz, *Neuroprotection by the inhibition of apoptosis.* Brain Pathology, 2000. 10(2): p. 283-292.
98. Andersen, E. R., L. T. Holmaas, and V. Olaisen, *Process for the production of DTPA-bis anhydride.* 2008, EP Patent 1,711,479.
99. Shalviri, A., H. K. Chan, G. Raval, M. J. Abdekhodaie, Q. Liu, H. Heerklotz, and X. Y. Wu, *Design of pH-responsive Nanoparticles of Terpolymer of Poly (methacrylic acid), Polysorbate 80 and Starch for Delivery of Doxorubicin.* Colloids and Surfaces B: Biointerfaces, 2013. 101: p. 405-413.
100. Barge, A., G. Cravotto, E. Gianolio, and F. Fedeli, *How to determine free Gd and free ligand in solution of Gd chelates. A technical note.* Contrast Media Mol. Imaging, 2006. 1(5): p. 184-188.

The invention claimed is:

1. A method of producing a nanoparticle, the method comprising the steps of:
(a) solubilising a first polymer in a liquid solution;
(b) adding a polymerizable monomer comprising a carboxylic acid side group or an alkylaminoalkyl ester side group to the liquid solution containing the solubilized polymer;
(c) graft polymerizing the monomer to form polymeric chains of a second polymer on the solubilised first polymer, wherein:
step (c) is conducted in the presence of polyethoxylated sorbitan-based molecules having a functional group reactive with the forming second polymeric chains, wherein the first polymer comprises starch and the second polymer comprises poly(methacrylic) acid, to covalently link the polyethoxylated sorbitan-based molecules to the second polymeric chains.

2. The method of claim 1, wherein the liquid solution comprises a hydroxylic solvent.

3. The method of claim 1, wherein the polyethoxylated sorbitan-based molecules are a polyethoxylated sorbitan ester having a R(C9-C31)-C(O)O-group wherein the polyethoxylated sorbitan ester is linked to the second polymer through a C—C covalent bond of the R(C9-C31)-C(O)O-group during the step of polymerizing.

4. A method of producing a nanoparticle for delivery of a biological agent, comprising the method of claim 3, wherein the agent is covalently linked to the polymer of step (a).

5. A method of producing nanoparticles for delivery of a biological agent, comprising dispersing the agent and nanoparticles obtained by the method of claim 3, in a liquid medium to incorporate the agent into the nanoparticles.

6. The method of claim 1, further comprising the step of providing a crosslinker.

7. A nanoparticle comprising:
a first polymer;
a second polymer grafted to the first polymer; and
a polyethoxylated sorbitan-based moiety covalently bound to the second polymer, wherein the first polymer comprises starch and the second polymer comprises poly(methacrylic) acid.

8. The nanoparticle of claim 7, wherein the polyethoxylated sorbitan-based moiety is a sorbitan ester having a R(C9-C31)-C(O)O-group wherein the polyethoxylated sorbitan ester is linked to the second polymer through a C—C covalent bond of the R-group.

9. The nanoparticle of claim 7, wherein the second polymer is crosslinked.

10. A composition comprising a plurality of nanoparticles of claim 9, further comprising a pharmaceutically active agent.

11. A composition comprising a plurality of nanoparticles of any of claim 9, further comprising a signal molecule, a biological agent, or a pharmaceutically active agent.

12. The composition of claim 11, further comprising a pharmaceutically active agent.

13. The nanoparticle of claim 7 wherein the second polymer is crosslinked; and
the polyethoxylated sorbitan-based moiety is a polyethoxylated sorbitan ester comprising a (C9-C31)R—C(O)O— group covalently bound to the second polymer by a C—C bond between the carbon backbone of the second polymer and the R group.

14. The nanoparticle of claim 13, wherein the polyethoxylated sorbitan ester comprises the groups —O(CH$_2$CH$_2$O)$_w$—C(O)(C17)R, HO(CH$_2$CH$_2$O)$_x$—, HO(CH$_2$CH$_2$O)$_y$—, HO(CH$_2$CH$_2$O)$_z$—, wherein w+x+y+z=20.

15. The nanoparticle of claim 14, wherein the molar ratio of the monomeric unit of the starch to the monomeric methacrylate units of the poly(methacrylic acid) is between 0.2 and 8.0.

16. The nanoparticle of claim 15, wherein the molar ratio of the polysorbate and the monomeric methacrylate units of the poly(methacrylic acid) is between 0.002 and 0.03.

* * * * *

UNITED STATES PATENT AND TRADEMARK OFFICE
CERTIFICATE OF CORRECTION

PATENT NO. : 10,233,277 B2
APPLICATION NO. : 14/382495
DATED : March 19, 2019
INVENTOR(S) : Xiao Yu Wu et al.

Page 1 of 1

It is certified that error appears in the above-identified patent and that said Letters Patent is hereby corrected as shown below:

In the Claims

In Column 54, Lines 4-6, in Claim 1, after "chains," delete "wherein the first polymer comprises starch and the second polymer comprises poly(methacrylic) acid,".

In Column 54, Line 8, in Claim 1, delete "chains." and insert -- chains, wherein the first polymer comprises starch and the second polymer comprises poly(methacrylic) acid. --, therefor.

Signed and Sealed this
Twenty-fifth Day of June, 2019

Andrei Iancu
*Director of the United States Patent and Trademark Office*